US012391750B2

(12) United States Patent
Panicker et al.

(10) Patent No.: US 12,391,750 B2
(45) Date of Patent: Aug. 19, 2025

(54) ANTI-C1S ANTIBODIES AND METHODS OF USE THEREOF

(71) Applicant: Bioverativ USA Inc., Waltham, MA (US)

(72) Inventors: Sandip Panicker, South San Francisco, CA (US); Graham Parry, South San Francisco, CA (US); Nancy E. Stagliano, South San Francisco, CA (US)

(73) Assignee: Bioverativ USA Inc., Waltham, MA (US)

( * ) Notice: Subject to any disclaimer, the term of this patent is extended or adjusted under 35 U.S.C. 154(b) by 0 days.

(21) Appl. No.: 18/349,027

(22) Filed: Jul. 7, 2023

(65) Prior Publication Data

US 2024/0076363 A1 Mar. 7, 2024

Related U.S. Application Data

(63) Continuation of application No. 16/340,991, filed as application No. PCT/US2017/056349 on Oct. 12, 2017, now abandoned.

(60) Provisional application No. 62/407,390, filed on Oct. 12, 2016.

(51) Int. Cl.
| | |
|---|---|
| *A61K 39/00* | (2006.01) |
| *A61K 39/395* | (2006.01) |
| *C07K 16/18* | (2006.01) |
| *A61K 38/00* | (2006.01) |
| *A61K 45/06* | (2006.01) |

(52) U.S. Cl.
CPC .............. *C07K 16/18* (2013.01); *A61K 38/00* (2013.01); *A61K 45/06* (2013.01); *C07K 2317/24* (2013.01); *C07K 2317/52* (2013.01); *C07K 2317/76* (2013.01); *C07K 2317/92* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,945,039 A | 7/1990 | Suzuki et al. |
| 6,090,777 A | 7/2000 | Hack et al. |
| 7,049,282 B2 | 5/2006 | Frank et al. |
| 7,071,299 B2 | 7/2006 | West et al. |
| 7,563,441 B2 | 7/2009 | Graus et al. |
| 7,666,627 B2 | 2/2010 | Gal et al. |
| 7,897,561 B2 | 3/2011 | Kotwal et al. |
| 7,919,094 B2 | 4/2011 | Schwaeble et al. |
| 7,923,010 B2 | 4/2011 | Christadoss et al. |
| 8,071,532 B2 | 12/2011 | Mannesse et al. |
| 8,148,330 B2 | 4/2012 | Barres et al. |
| 8,163,881 B2 | 4/2012 | Ober |
| 8,221,756 B2 | 7/2012 | Fung et al. |
| 8,329,169 B2 | 12/2012 | Fung et al. |
| 8,415,288 B2 | 4/2013 | Mannesse et al. |
| 8,501,705 B2 | 8/2013 | Christadoss et al. |
| 8,545,850 B2 | 10/2013 | Chen et al. |
| 8,877,197 B2 | 11/2014 | van Vlasselaer et al. |
| 8,945,562 B2 | 2/2015 | van Vlasselaer et al. |
| 9,074,003 B2 | 7/2015 | van Vlasselaer et al. |
| 9,074,004 B2 | 7/2015 | van Vlasselaer et al. |
| 9,206,259 B2 | 12/2015 | van Vlasselaer et al. |
| 9,512,233 B2 | 12/2016 | van Vlasselaer et al. |
| 9,562,092 B2 | 2/2017 | van Vlasselaer et al. |
| 9,562,106 B2 | 2/2017 | van Vlasselaer et al. |
| 10,450,382 B2 | 10/2019 | van Vlasselaer et al. |
| 10,457,745 B2 | 10/2019 | van Vlasselaer et al. |
| 10,729,767 B2 | 8/2020 | Panicker et al. |
| 11,246,926 B2 | 2/2022 | Panicker et al. |
| 12,215,169 B2 | 2/2025 | Van Vlasselaer et al. |
| 2002/0010948 A1 | 1/2002 | Patience |
| 2002/0037915 A1 | 3/2002 | Illig et al. |
| 2002/0102256 A1 | 8/2002 | West et al. |
| 2003/0190311 A1 | 10/2003 | Dall'Acqua et al. |
| 2004/0115194 A1 | 6/2004 | Wang |
| 2004/0219147 A1 | 11/2004 | Bell |
| 2005/0004031 A1 | 1/2005 | Subasinghe et al. |
| 2005/0032157 A1 | 2/2005 | Gal et al. |

(Continued)

FOREIGN PATENT DOCUMENTS

| | | |
|---|---|---|
| CA | 1276103 C | 11/1990 |
| CN | 101298481 A | 11/2008 |

(Continued)

OTHER PUBLICATIONS

Querol et al. An innovative phase 2 proof-of-concept trial design to evaluate SAR445088, a monoclonal antibody targeting complement C1s in chronic inflammatory demyelinating polyneuropathy. J Peripher Nerv Syst. 2023;28:276-285. (Year: 2023).*

Chow et al. First-in-human study with SAR445088: A novel selective classical complement pathway inhibitor. Clin Transl Sci. 2023; 16:673-685. (Year: 2023).*

Partial Supplementary European Search Report in connection with Application No. EP 20156431.7 mailed Aug. 21, 2020.

Extended European Search Report in connection with Application No. EP 20156431.7 mailed Nov. 26, 2020.

International Search Report and Written Opinion in connection with Application No. PCT/US2013/066783 mailed May 5, 2014.

International Preliminary Report on Patentability in connection with Application No. PCT/US2013/066783 mailed May 7, 2015.

(Continued)

*Primary Examiner* — Maher M Haddad
(74) *Attorney, Agent, or Firm* — Wolf, Greenfield & Sacks, P.C.

(57) ABSTRACT

The present disclosure provides antibodies that specifically bind complement pathway component C1s The present disclosure provides nucleic acids comprising nucleotide sequences encoding the anti-C1s antibodies; and host cells comprising the nucleic acids. The present disclosure provides compositions comprising the anti-C1s antibodies. The present disclosure provides methods of use of the anti-C1s antibodies.

16 Claims, 18 Drawing Sheets

Specification includes a Sequence Listing.

(56) References Cited

U.S. PATENT DOCUMENTS

| | | |
|---|---|---|
| 2005/0079174 A1 | 4/2005 | Barbera-Guillem et al. |
| 2005/0136494 A1 | 6/2005 | Akita et al. |
| 2005/0177882 A1 | 8/2005 | Gavin et al. |
| 2005/0222027 A1 | 10/2005 | Chiang et al. |
| 2005/0267035 A1 | 12/2005 | West et al. |
| 2005/0271660 A1 | 12/2005 | Wang |
| 2006/0002937 A1 | 1/2006 | Schwaeble et al. |
| 2006/0008883 A1 | 1/2006 | Lazar et al. |
| 2006/0018896 A1 | 1/2006 | Schwaeble et al. |
| 2006/0148015 A1 | 7/2006 | Roos et al. |
| 2006/0173170 A1 | 8/2006 | Chamberlain et al. |
| 2007/0172483 A1 | 7/2007 | Schwaeble et al. |
| 2008/0075712 A1 | 3/2008 | Hattori et al. |
| 2008/0160015 A1 | 7/2008 | Gilles et al. |
| 2008/0167449 A1 | 7/2008 | Lazar et al. |
| 2008/0206242 A1 | 8/2008 | Lawrence et al. |
| 2008/0233113 A1 | 9/2008 | Bansal |
| 2009/0163699 A1 | 6/2009 | Chamberlain et al. |
| 2009/0259019 A1 | 10/2009 | Willis et al. |
| 2009/0269356 A1 | 10/2009 | Epstein et al. |
| 2009/0324585 A1 | 12/2009 | Robinson et al. |
| 2010/0074899 A1 | 3/2010 | Schwaeble et al. |
| 2010/0143343 A1 | 6/2010 | Halstead et al. |
| 2010/0143344 A1 | 6/2010 | Baas et al. |
| 2010/0166862 A1 | 7/2010 | Francois et al. |
| 2011/0002931 A1 | 1/2011 | Tamburini |
| 2011/0020337 A1 | 1/2011 | Schwaeble et al. |
| 2011/0081347 A1 | 4/2011 | Gorlatov |
| 2011/0091450 A1 | 4/2011 | Schwaeble et al. |
| 2011/0104156 A1 | 5/2011 | Christadoss et al. |
| 2011/0190221 A1 | 8/2011 | Francois et al. |
| 2011/0263436 A1 | 10/2011 | Tu et al. |
| 2011/0281757 A1 | 11/2011 | Tyan et al. |
| 2011/0311549 A1 | 12/2011 | Schwaeble et al. |
| 2011/0311550 A1 | 12/2011 | Law et al. |
| 2011/0312505 A1 | 12/2011 | Reddy et al. |
| 2012/0195880 A1 | 8/2012 | Barres et al. |
| 2012/0225056 A1 | 9/2012 | Rother et al. |
| 2012/0230953 A1 | 9/2012 | Goldenberg et al. |
| 2012/0244139 A1 | 9/2012 | Madison et al. |
| 2012/0251549 A1 | 10/2012 | Fung et al. |
| 2012/0258095 A1 | 10/2012 | Demopulos et al. |
| 2012/0263717 A1 | 10/2012 | Dennis et al. |
| 2012/0282263 A1 | 11/2012 | Dudler et al. |
| 2012/0308566 A1 | 12/2012 | Martin et al. |
| 2012/0309943 A1 | 12/2012 | Kumada et al. |
| 2012/0315266 A1 | 12/2012 | Olson et al. |
| 2012/0328601 A1 | 12/2012 | Barres et al. |
| 2013/0064820 A1 | 3/2013 | Magro |
| 2013/0078245 A1 | 3/2013 | Holers et al. |
| 2013/0123473 A1 | 5/2013 | Goldenberg et al. |
| 2013/0202612 A1 | 8/2013 | Lin et al. |
| 2013/0203678 A1 | 8/2013 | Francois et al. |
| 2013/0224187 A1 | 8/2013 | Rother et al. |
| 2013/0237589 A1 | 9/2013 | Benedict et al. |
| 2013/0244941 A1 | 9/2013 | Mannesse et al. |
| 2013/0259860 A1 | 10/2013 | Smith et al. |
| 2013/0261287 A1 | 10/2013 | Sabbadini et al. |
| 2013/0273052 A1 | 10/2013 | Gies et al. |
| 2013/0281677 A1 | 10/2013 | Wilson et al. |
| 2014/0127196 A1 | 5/2014 | van Vlasselaer et al. |
| 2014/0127208 A1 | 5/2014 | van Vlasselaer et al. |
| 2014/0140933 A1 | 5/2014 | van Vlasselaer et al. |
| 2014/0220014 A1 | 8/2014 | Dillon et al. |
| 2014/0294812 A1 | 10/2014 | Lazar |
| 2014/0357843 A1 | 12/2014 | Oh et al. |
| 2015/0259437 A1 | 9/2015 | van Vlasselaer et al. |
| 2015/0329645 A1 | 11/2015 | van Vlasselaer et al. |
| 2016/0090425 A1 | 3/2016 | Rosenthal et al. |
| 2016/0159890 A1 | 6/2016 | Rosenthal et al. |
| 2016/0326237 A1 | 11/2016 | Rosenthal et al. |
| 2017/0226229 A1 | 8/2017 | van Vlasselaer et al. |
| 2017/0226230 A1 | 8/2017 | van Vlasselaer et al. |
| 2018/0092974 A1 | 4/2018 | Panicker et al. |
| 2018/0169240 A1 | 6/2018 | Parry et al. |
| 2020/0048332 A1 | 2/2020 | Panicker et al. |
| 2020/0079875 A1 | 3/2020 | van Vlasselaer et al. |
| 2020/0079876 A1 | 3/2020 | van Vlasselaer et al. |
| 2020/0405852 A1 | 12/2020 | Panicker et al. |
| 2021/0115116 A1 | 4/2021 | van Vlasselaer et al. |
| 2022/0185912 A1 | 6/2022 | van Vlasselaer et al. |
| 2022/0204647 A1 | 6/2022 | van Vlasselaer et al. |
| 2022/0249664 A1 | 8/2022 | Parry et al. |
| 2023/0357433 A1 | 11/2023 | Arias et al. |
| 2024/0025978 A1 | 1/2024 | Alonso et al. |
| 2024/0052062 A1 | 2/2024 | Hobbs et al. |
| 2024/0117021 A1 | 4/2024 | Patke et al. |

FOREIGN PATENT DOCUMENTS

| | | |
|---|---|---|
| CN | 102170906 A | 8/2011 |
| CN | 102203610 A | 9/2011 |
| CN | 102459334 A | 5/2012 |
| CN | 104870475 A | 8/2015 |
| CN | 104884088 A | 9/2015 |
| CN | 105143261 A | 12/2015 |
| EP | 2 266 606 A1 | 12/2010 |
| JP | 61271455 A | 12/1986 |
| JP | 2007-535474 A | 12/2007 |
| JP | 2008-533156 A | 8/2008 |
| JP | 2012-510282 | 5/2012 |
| JP | 2013-136530 A | 7/2013 |
| JP | 2016-503400 | 2/2016 |
| JP | 2016-505240 | 2/2016 |
| JP | 2016-520313 | 7/2016 |
| JP | 6538561 B2 | 7/2019 |
| JP | 6543572 B2 | 7/2019 |
| JP | 6691183 B2 | 4/2020 |
| JP | 6889308 B1 | 5/2021 |
| WO | WO 01/57079 A2 | 8/2001 |
| WO | WO 03/009803 A2 | 2/2003 |
| WO | WO 2005/056759 A2 | 6/2005 |
| WO | WO 2006/101860 A1 | 9/2006 |
| WO | WO 2007/022416 A2 | 2/2007 |
| WO | WO 2008/060645 A2 | 5/2008 |
| WO | WO 2008/074227 A1 | 6/2008 |
| WO | WO 2009/086320 A1 | 7/2009 |
| WO | WO 2011/102342 A1 | 8/2011 |
| WO | WO 2012/028622 A2 | 3/2012 |
| WO | WO 2013/093027 A1 | 6/2013 |
| WO | WO 2014/066744 A2 | 5/2014 |
| WO | WO 2014/071206 A1 | 5/2014 |
| WO | WO 2015/084999 A1 | 6/2015 |
| WO | WO 2016/059512 A1 | 4/2016 |
| WO | WO 2016/164358 A1 | 10/2016 |
| WO | WO 2016/210172 A1 | 12/2016 |
| WO | WO 2018/071676 A1 | 4/2018 |
| WO | WO 2018/170145 A1 | 9/2018 |
| WO | WO 2018/204368 A1 | 11/2018 |
| WO | WO 2019/198807 A1 | 10/2019 |
| WO | WO 2020/081408 A1 | 4/2020 |
| WO | WO 2022/031978 A1 | 2/2022 |

OTHER PUBLICATIONS

Extended European Search Report in connection with Application No. EP 21157955.2 mailed Aug. 31, 2021.
Extended European Search Report in connection with Application No. EP 22207626.7 mailed on Jun. 15, 2023.
International Search Report and Written Opinion in connection with Application No. PCT/US2016/026038 mailed Aug. 30, 2016.
International Preliminary Report on Patentability in connection with Application No. PCT/US2016/026038 mailed Oct. 19, 2017.
Partial Supplementary European Search Report in connection with Application No. EP 16815332.8 mailed on Feb. 12, 2019.
Extended European Search Report in connection with Application No. EP 16815332.8 mailed on May 15, 2019.
International Search Report and Written Opinion in connection with Application No. PCT/US2016/039087 mailed Oct. 4, 2016.
International Preliminary Report on Patentability in connection with Application No. PCT/US2016/039087 mailed Jan. 4, 2018.

(56) References Cited

OTHER PUBLICATIONS

Extended European Search Report in connection with Application No. EP 17859451.1 mailed May 13, 2020.
International Search Report and Written Opinion in connection with Application No. PCT/US2017/056349 mailed Jan. 23, 2018.
International Preliminary Report on Patentability in connection with Application No. PCT/US2017/056349 mailed Apr. 25, 2019.
International Search Report and Written Opinion in connection with Application No. PCT/US2018/022462 mailed Jun. 12, 2018.
International Preliminary Report on Patentability in connection with Application No. PCT/US2018/022462 mailed Sep. 26, 2019.
International Search Report and Written Opinion for PCT/US2021/044761 mailed Nov. 30, 2021.
International Preliminary Report on Patentability for PCT/US2021/044761 mailed Feb. 16, 2023.
International Search Report and Written Opinion in connection with Application No. PCT/US2022/022745 mailed Jul. 1, 2022.
International Preliminary Report on Patentability in connection with Application No. PCT/US2022/022745 mailed Oct. 12, 2023.
International Search Report and Written Opinion in connection with Application No. PCT/US2023/068420 mailed Sep. 22, 2023.
International Search Report and Written Opinion in connection with Application No. PCT/US2023/069027 mailed Nov. 7, 2023.
[No Author Listed] True North Therapeutics: Study NCT02502903. Jul. 14, 2016 (v3). Retrieved from the Internet: https://clinicaltrials.gov/ct2/history/NCT02502903?V_1=View#StudyPageTop on May 23, 2018. 7 pages.
[No Author Listed], ClinicalTrials.gov Identifier: NCT03347422. A Study to Assess the Efficacy and Safety of BIVV009 (Sutimlimab) in Participants With Primary Cold Agglutinin Disease Without A Recent History of Blood Transfusion (Cadenza). Sep. 1, 2020. https://clinicaltrials.gov/ct2/history/NCT03347422?V_54=View#StudyPageTop [last accessed Jun. 22, 2022]. pp. 7-13.
Almagro et al., "Humanization of Antibodies," Frontiers in Bioscience 13:1619-1633, Frontiers In Bioscience Publications, United States (2008).
An et al., "IgG2m4, an Engineered Antibody Isotype with Reduced Fc function," Mabs 1(6):572-579, Philadelphia, PA : Taylor & Francis, United States (Nov.-Dec. 2009).
Angal et al., A single amino acid substitution abolishes the heterogeneity of chimeric mouse/human (IgG4) antibody. Mol Immunol. Jan. 1993;30(1):105-8.
Anti-Complement C1s Antibody [clone 2011], Cat# LS-C173719, Lifespan Biosciences, accessed at http://www.lsbio.com/antibodies/anti-complement-c1s-antibody-clone-2d11-mouse-anti-humanmonoclonal-for-ihc-western-blot-ls-c173719/181143, 2014.
Anti-Complement C1s Antibody [clone 2A8], Cat# LS-C173720, Lifespan Biosciences, accessed at http://www.lsbio.com/antibodies/anti-complement-c1s-anti body-clone-2a8-mouse-anti-human-monoclonal-for-ihewestern-blot-ls-c173720/181144, 2014.
Anti-Complement C1s Antibody [clone 2F5], Cat# LS-C173425, Lifespan Biosciences, accessed at http://www.lsbio.com/antibodies/anti-complement-c1s-antibody-ciane-2f5-mouse-anti-human-monoclonalfor-western-blot-ls-c173425/180849, 2014.
Anti-Complement C1s Antibody [clone 409], Cat# LS-C173424, Lifespan Biosciences, accessed at http://www.lsbio.com/antibodies/anti-complement-c1s-antibody-ciane-4d9-mouse-anti-human-monoclonal-for-western-blot-ls-c173424/180848, 2014.
Anti-Complement C1s Antibody [clone 49], Cat# LS-C6209, Lifespan Biosciences, accessed at http://www.lsbio.com/antibodies/anti-complement-c1s-antibody-ciane-49-mouse-anti-human-monoclonalls-c6209/6950, 2014.
Anti-Complement C1s Antibody [clone 5F2], Cat# LS-C173718, Lifespan Biosciences, accessed at http://www.lsbio.com/antibodies/anti-complement-c1s-antibody-clone-5f2-mouse-anti-human-monoclonal-for-ihc-western-blot-ls-c173718/181142, 2014.
Anti-Complement C1s Antibody, Cat# LS-C121168, Lifespan Biosciences, accessed at http://www.lsbio.com/antibodies/anti-complement-c1s-antibody-mouse-anti-human-monoclonal-for-ihc-western-blot-ls-c121168/124626, 2014.
Anti-Complement C1s Antibody, Cat# LS-C6208, Lifespan Biosciences, accessed at http://www.lsbio.com/antibodies/anticomplement-c1s-antibody-mouse-anti-human-monoclonal-ls-c6208/6949, 2014.
Anti-Complement C1s Antibody (aa1-688), Cat# LS-C128271, Lifespan Biosciences, accessed at http://www.lsbio.com/antibodies/anti-complement-c1s-antibody-aa1-688-mouse-anti-human-polyclonal-for-western-blot-ls-c128271 /131891, 2014.
Anti-Complement C1s Antibody (Internal) [clone EPR9066(B)], Cat# LS-C154717, Lifespan Biosciences, accessed at http://www.lsbio.com/antibodies/anti-complement-c1s-antibody-internal-clone-epr9066b-rabbit-anti-human-monoclonal-for-ihc-western-blot-ls-c154717/161392, 2014.
Anti-Complement C1s Antibody (Internal) [clone EPR9067(B)], Cat# LS-C154704, Lifespan Biosciences, accessed at http://www.lsbio.com/antibodies/anti-complement-c1s-antibody-internal-clone-epr9067b-rabbit-anti-human-monoclonal-for-western-blot-ls-c154704/161379, 2014.
Anti-Complement C1s Antibody [clone M81], Cat# LS-C140039, accessed at Lifespan Biosciences, accessed at http://www.lsbio.com/antibodies/anti-complement-c1s-antibody-clone-m81-mouse-anti-human-monoclonal-for-ihc-western-blot-ls-c140039/144752, 2014.
Anti-Complement C1s Antibody [clone 401 0], Cat# LS-C173540, Lifespan Biosciences, accessed at http://www.lsbio.com/antibodies/anti-complement-c1s-anti body-clone-4d10-mouse-anti-human-monoclonal-for-westernblot-ls-c173540/180964, 2014.
Bai, S., A guide to rational dosing of monoclonal antibodies. Clin Pharmacokinet. Feb. 1, 2012;51(2):119-35. doi: 10.2165/11596370-000000000-00000.
Baker et al., Immunogenicity of protein therapeutics: The key causes, consequences and challenges. Self Nonself. Oct. 2010;1(4):314-322. doi: 10.4161/self.1.4.13904.
Basiglio et al., "Complement Activation and Disease: Protective Effects of Hyperbilirubinaemia," Clinical Science 118(2):99-113, London : Portland Press on behalf of the Medical Research Society and the Biochemical Society, England (Oct. 2009).
Baynes et al., Role of arginine in the stabilization of proteins against aggregation. Biochemistry. Mar. 29, 2005;44(12):4919-25. doi: 10.1021/bi047528r.
Berentsen et al., Novel insights into the treatment of complement-mediated hemolytic anemias. Ther Adv Hematol. Sep. 9, 2019;10:2040620719873321. doi: 10.1177/2040620719873321.
Brahmi et al., "Synergistic Inhibition of Human Cell-Mediated Cytotoxicity by Complement Component Antisera Indicates That Target Cell Lysis May Result From an Enzymatic Cascade Involving Granzymes and Perforin," Nature Immunology 14(5-6):271-285, New York : S. Karger, Switzerland (Sep. 1995).
Brown et al., Tolerance of single, but not multiple, amino acid replacements in antibody VH CDR 2: a means of minimizing B cell wastage from somatic hypermutation? J Immunol. May 1, 1996;156(9):3285-91.
Caldas et al., "Humanization of the anti-CD18 antibody 6.7: an unexpected effect of a framework residue in binding to antigen," Mol. Immunol., 39(15):941-952 (2003) (Elsevier Pub., Cambridge, MA).
Carroll "Strategies for Generating Therapeutic Antibodies," Dissertation, The University of Texas at Austin, 170 pages (Aug. 2012).
Carroll et al., "Antibody-Mediates Inhibition of Human C1s and the Classical Complement Pathway," Immunobiology 218(8):1041-1048, Amsterdam : Elsevier, Netherlands (Aug. 2013).
Chen et al., "Enhancement and Destruction of Antibody Function by Somatic Mutation: Unequal Occurrence Is Controlled by V Gene Combinatorial Associations," The EMBO Journal 14(12):2784-2794, Wiley Blackwell, England (1995).
Chester et al., Clinical issues in antibody design. Trends Biotechnol. Aug. 1995;13(8):294-300. doi: 10.1016/S0167-7799(00)88968-4.
Collett, J. "Dosage Regimens", Jan. 1, 2001 (Jan. 1, 2001), Pharmaceutics. The Science Of Dosage Form Design Ed. 2, Churchill Livingstone, pp. 275-288, Xp003030862, ISBN: 978-0-443-05517-1.
Colman, "Effects of Amino Acid Sequence Changes on Antibody-antigen Interactions," Research in Immunology 145(1):33-36, Elsevier, France (Jan. 1994).

(56) References Cited

OTHER PUBLICATIONS

D'Angelo et al., Many Routes to an Antibody Heavy-Chain CDR3: Necessary, Yet Insufficient, for Specific Binding. Front Immunol. Mar. 8, 2018;9:395. doi: 10.3389/fimmu.2018.00395. eCollection 2018.
Datta-Mannan et al., The interplay of non-specific binding, target-mediated clearance and FcRn interactions on the pharmacokinetics of humanized antibodies. MAbs. 2015;7(6):1084-93. doi: 10.1080/19420862.2015.1075109. Epub Sep. 4, 2015.
Derhaschnig et al., Combined integrated protocol/basket trial design for a first-in-human trial. Orphanet J Rare Dis. Oct. 4, 2016;11(1):134.
Dmytrijuk et al., FDA report: eculizumab (Soliris) for the treatment of patients with paroxysmal nocturnal hemoglobinuria. Oncologist. Sep. 2008;13(9):993-1000. doi: 10.1634/theoncologist.2008-0086. Epub Sep. 10, 2008.
Doevendans et al., Immunogenicity of Innovative and Biosimilar Monoclonal Antibodies. Antibodies (Basel). Mar. 5, 2019;8(1):21. doi: 10.3390/antib8010021.
Du et al., "Molecular basis of recognition of human osteopontin by 23C3, a potential therapeutic antibody for treatment of rheumatoid arthritis," J Mol. Biol., 382(4):835-842 (2008), United Kingdom.
Dua et al., A Tutorial on Target-Mediated Drug Disposition (TMDD) Models. CPT Pharmacometrics Syst Pharmacol. Jun. 2015;4(6):324-37. doi: 10.1002/psp4.41. Epub Jun. 15, 2015. Supporting Information, 11 pages.
Dumet et al., Insights into the IgG heavy chain engineering patent landscape as applied to IgG4 antibody development. MAbs. Nov.-Dec. 2019;11(8):1341-1350. doi: 10.1080/19420862.2019.1664365. Epub Sep. 26, 2019.
Fitzpatrick et al., An open label clinical trial of complement inhibition in multifocal motor neuropathy. J Peripher Nerv Syst. Jun. 2011;16:84-91.
Foote et al., "Antibody framework residues affecting the conformation of the hypervariable loops," J. Mol. Biol. 224:487-499, Elsevier, Netherlands (1992) (Elsevier Pub., Cambridge, MA).
Frank et al., Cold agglutinins and cold-agglutinin disease. Annu Rev Med. 1977;28:291-8. doi: 10.1146/annurev.me.28.020177.001451.
Gal et al., "C1s, the Protease Messenger of C1. Structure, Function and Physiological Significance," Immunobiology 205(4-5):383-394, Amsterdam : Elsevier, Netherlands (Sep. 2002).
Gal et al., "Early Complement Proteases: C1r, C1s and MASPs. A Structural Insight into Activation and Functions," Molecular Immunology 46(14):2745-2752, Elmsford, N. Y., Pergamon Press, England (May 2009).
Hamad et al., "Complement Activation by PEGylated Single-Walled Carbon Nanotubes Is Independent of C1q and Alternative Pathway Turnover," Molecular Immunology 45(14):3797-3803, Elmsford, N. Y., Pergamon Press, England (Aug. 2008 ). Author manuscript.
Hamano et al., High Serum IgG4 Concentrations in Patients with Sclerosing Pancreatitis, 2001, New England Journal of Medicine, vol. 344, No. 10, pp. 732-738 (Year: 2001).
Heinz et al., "Monoclonal Antibodies Against Components of the Classical Pathway of Complement," Complement and Inflammation 6(3):166-174, New York : Karger, Switzerland (1989).
Hinson et al., Prediction of Neuromyelitis Optica Attack Severity by Quantitation of Complement-Mediated Injury to Aquaporin-4-Expressing Cells. Arch Neurol. Sep. 2009;66(9):1164-7.
Ishikawa et al., Influence of pH on heat-induced aggregation and degradation of therapeutic monoclonal antibodies. Biol Pharm Bull. 2010;33(8):1413-7. doi: 10.1248/bpb.33.1413.
Iwata et al., Bullous pemphigoid: role of complement and mechanisms for blister formation within the lamina lucida. Exp Derm. May 7, 2013;22:381-5.
Jaeger et al., Therapeutic Rationale and Clinical Development of TNT009, an Upstream Classical Pathway Inhibitor, for Cold Agglutinin Disease. Blood. 2015;126:3560. Retrieved from the Internet: http://www.bloodjournal.org/content/126/23/3560. 7 pages.
Jilma et al., Chronic Inhibition of Complement C1s By TNT009 Produces Sustained, Complete Remission in Patients with Severe, Transfusion-Dependent Cold Agglutinin Disease (CAD). Blood. 2016;128:2435. Retrieved from the Internet: http://www.bloodjournal.org/content/128/22/2435 on Apr. 9, 2019. 8 pages.
Kaminski et al., Multiparameter flow cytometry and bioanalytics for B cell profiling in systemic lupus erythematosus. Methods Mol Biol. 2012;900:109-34. doi: 10.1007/978-1-60761-720-4_6.
Kidmose et al., "Structural Basis for Activation of the Complement System by Component C4 Cleavage," Proceedings of the National Academy of Sciences 109(38):15425-15430, Washington, DC : National Academy of Sciences, United States (Sep. 2012).
Klechevsky et al., Cross-priming CD8+ T cells by targeting antigens to human dendritic cells through DCIR. Blood. Sep. 9, 2010;116(10):1685-97. doi: 10.1182/blood-2010-01-264960. Epub Jun. 7, 2010.
Konstantinov et al., Detection of autoantibodies in a point-of-care rheumatology setting. Auto Immun Highlights. May 18, 2013;4(2):55-61. doi: 10.1007/s13317-013-0052-9.
Kusner et al., Effect of complement and its regulation on myasthenia gravis pathogenesis. Expert Rev Clin Immunol. Jan. 2008;4(1):43-52.
Kussie et al., "A Single Engineered Amino Acid Substitution Changes Antibody Fine Specificity," Journal of Immunology 152(1):146-152, American Association of Immunologists, United States (1994).
Matsumoto et al., "Acceleration of Site-To-Site Transfer of C1—by a Monoclonal Antibody to C1-s ," Molecular Immunology 26(8):697-703, Oxford, Elmsford, N. Y., Pergamon Press, England (Aug. 1989).
Matsumoto et al., "Functional Analysis of Activated C1s, a Subcomponent of the First Component of Human Complement, by Monoclonal Antibodies," Journal of Immunology 137(9):2907-2912, Baltimore : Williams & Wilkins, United States (Nov. 1986).
Matsumoto et al., "Probing the C4-Binding Site on C1s with Monoclonal Antibodies. Evidence for a C4/C4b-Binding Site on the Gamma-Domain," Journal of Immunology 142(8):2743-2750, Baltimore : Williams & Wilkins, United States (Apr. 1989).
Monnet et al., Selection of IgG Variants with Increased FcRn Binding Using Random and Directed Mutagenesis: Impact on Effector Functions. Front Immunol. Feb. 4, 2015;6:39. doi: 10.3389/fimmu.2015.00039.
Moore et al., Engineered Fc variant antibodies with enhanced ability to recruit complement and mediate effector functions. MAbs. Mar.-Apr. 2010;2(2):181-9.
Mould et al., The pharmacokinetics and pharmacodynamics of monoclonal antibodies—mechanistic modeling applied to drug development. Curr Opin Drug Discov Devel. Jan. 2007;10(1):84-96.
Mühlbacher et al., Blockade of HLA Antibody-Triggered Classical Complement Activation in Sera From Subjects Dosed With the Anti-C1s Monoclonal Antibody TNT009—Results from a Randomized First-in-Human Phase 1 Trial. Transplantation. Oct. 2017;101(10):2410-2418. doi: 10.1097/TP.0000000000001804.
Nagaki et al., "Specific Antisera to C1s: Detection of Different Electrophoretic Species of C1s," Journal of Immunology 103(1):141-145, Baltimore : Williams & Wilkins, United States (Jul. 1969).
Nakagawa et al., "Complement C1s Activation In Degenerating Articular Cartilage of Rheumatoid Arthritis Patients: Immunohistochemical Studies With an Active Form Specific Antibody," Annals of the Rheumatic Diseases 58(3):175-181, London : BMJ, England (Mar. 1999).
Nakagawa et al., "Coordinated Change Between Complement C1s Production and Chondrocyte Differentiation In Vitro," Cell and Tissue Research 289(2):299-305, Berlin, New York, Springer-Verlag, Germany (Aug. 1997).
Panicker et al., TNT009 Prevents Erythrocyte C3 Fragment Opsonization and Rescues Reticulocytes from Destruction in Patients with Cold Agglutinin Disease. Blood. 2016;128:94. Retrieved from the Internet: http://www.bloodjournal.org/content/128/22/94 on Apr. 9, 2019. 7 pages.
Phuan et al., "C1q-targeted Monoclonal Antibody Prevents Complement-Dependent Cytotoxicity and Neuropathology In in Vitro and Mouse Models of Neuromyelitis Optica," Acta Neuropathologica 125(6):829-840, Berlin : Springer Verlag, Germany (Jun. 2013). Author manuscript.

(56) References Cited

OTHER PUBLICATIONS

Piche-Nicholas et al., Changes in complementarity-determining regions significantly alter IgG binding to the neonatal Fc receptor (FcRn) and pharmacokinetics. MAbs. Jan. 2018;10(1):81-94. doi: 10.1080/19420862.2017.1389355. Epub Nov. 3, 2017.

Reddy et al., "Elimination of Fc Receptor-Dependent Effector Functions of a Modified IgG4 Monoclonal Antibody to Human CD4," Journal of Immunology 164(4):1925-1933, American Association of Immunologists, United States (2000).

Ricklin et al., Complement in Immune and Inflammatory Disorders: Pathophysiological Mechanisms. Apr. 15, 2013;190(8):3831-8.

Rossi et al., "Baculovirus-mediated Expression of Truncated Modular Fragments from the Catalytic Region of Human Complement Serine Protease C1s. Evidence for the Involvement of Both Complement Control Protein Modules In the Recognition of the C4 Protein Substrate," Journal of Biological Chemistry 273(2):1232-1239, Baltimore, MD : American Society for Biochemistry and Molecular Biology, United States (Jan. 1998).

Röth et al., Inhibition of complement C1s with sutimlimab in patients with cold agglutinin disease (CAD): results from the phase 3 cardinal study. Blood. Nov. 21, 2019;134:LBA-2.

Röth et al., Sutimlimab in Cold Agglutinin Disease. N Engl J Med. Apr. 8, 2021;384(14):1323-1334. doi: 10.1056/NEJMoa2027760.

Rudikoff et al., "Single Amino Acid Substitution Altering Antigen-binding Specificity," Proceedings of the National Academy of Sciences of the United States of America 79(6): 1979-1983, National Academy of Sciences, Washington (Mar. 1982).

Sakiyama et al., "Biochemical Characterization and Tissue Distribution of Hamster Complement C1s," Journal of Immunology. 146(1):183-187, Bethesda, MD : American Association of Immunologists, United States (Jan. 1991).

Sakiyama et al., "Complement C1s, a Classical Enzyme with Novel Functions at the Endochondral Ossification Center: Immunohistochemical Staining of Activated C1s with a Neoantigen-Specific Antibody," Cell and Tissue Research 288(3):557-565, Berlin, New York, Springer-Verlag, Germany (Jun. 1997).

Sakiyama et al., "Site-Directed Mutagenesis of Hamster Complement C1S: Characterization with an Active Form-Specific Antibody and Possible Involvement of C1S in Tumorigenicity," International Journal of Cancer 66(6):768-771, New York, NY : Wiley-Liss, United States (Jun. 1996).

Svačina et al., Chronic Inflammatory Demyelinating Polyneuropathy (CIDP): Current Therapies and Future Approaches. Curr Pharm Des. 2022;28(11):854-862. doi: 10.2174/1381612828666220325102840.

Sethi et al., Membranoproliferative Glomerulonephritis and C3 Glomerulopathy: Resolving the Confusion. Kidney Int. Mar. 2012;81(5):434-441.

Shi et al., TNT003, an inhibitor of the serine protease C1s, prevents complement activation induced by cold agglutinins. Blood. Jun. 26, 2014;123(26):4015-22. doi: 10.1182/blood-2014-02-556027. Epub Apr. 2, 2014.

Silva et al., The S228P mutation prevents in vivo and in vitro IgG4 Fab-arm exchange as demonstrated using a combination of novel quantitative immunoassays and physiological matrix preparation. J Biol Chem. Feb. 27, 2015;290(9):5462-9. doi: 10.1074/jbc.M114.600973. Epub Jan. 7, 2015.

Strobel et al., Hemolytic Transfusion Reactions. Transfus Med Hemother. Sep. 18, 2008;35:346-353.

Susuki et al., Anti-GM1 antibodies cause complement-mediated disruption of sodium channel clusters in peripheral motor nerve fibers. J Neurosci. Apr. 11, 2007;27(15):3956-67.

Thielens et al., "Comparative Study of the Fluid-Phase Proteolytic Cleavage of Human Complement Subcomponents C4 and C2 by C1s and C1r2-C1s2," FEBS Letters 165(1):111-116, West Sussex : John Wiley & Sons Ltd, England (Jan. 1984).

Tichaczek-Goska, Deficiencies and Excessive Human Complement System Activation in Disorders of Multifarious Etiology. Adv Clin Exp Med. Jan.-Feb. 2012;21(1):105-14.

Tseng et al., "Probing the Structure of C1 with an Anti-C1s Monoclonal Antibody: The Possible Existence of Two Forms of C1 in Solution," Molecular Immunology 34(8-9):671-679, Oxford, Elmsford, N. Y., Pergamon Press, England (Jun. 1997).

Veerhuis et al., "Early Complement Components in Alzheimer's Disease Brains," Acta Neuropathologica 91(1):53-60, Berlin : Springer Verlag, Germany (1996).

Wahrmann et al., Effect of the Anti-C1s Humanized Antibody TNT009 and Its Parental Mouse Variant TNT003 on HLA Antibody-Induced Complement Activation—A Preclinical In Vitro Study. Am J Transplant. Sep. 2017;17(9):2300-2311. doi: 10.1111/ajt.14256. Epub Mar. 31, 2017.

Walpole et al., The weight of nations: an estimation of adult human biomass. BMC Public Health. Jun. 18, 2012;12:439. doi: 10.1186/1471-2458-12-439.

Weitz et al., Inflammation and fatigue in patients with cold agglutinin disease (CAD): analysis from the phase 3 CARDINAL study. Blood. Nov. 5, 2020;136:7-8.

Williams et al., Humanising antibodies by CDR grafting. Antibody Engineering. 2010;1:319-39.

Wines et al., "The IgG Fc Contains Distinct Fc Receptor (FcR) Binding Sites: The Leukocyte Receptors Fc Gamma RI and Fc Gamma RIIa Bind to a Region in the Fc Distinct from that Recognized by Neonatal FcR and Protein A," Journal of Immunology 164(10):5313-5318, Bethesda, MD : American Association of Immunologists, United States (May 2000).

Zalevsky et al., Enhanced antibody half-life improves in vivo activity. Nat Biotechnol. Feb. 2010;28(2):157-9. doi: 10.1038/nbt.1601. Epub Jan. 17, 2010.

International Preliminary Report on Patentability for PCT/US2023/068420 mailed Dec. 26, 2024.

International Preliminary Report on Patentability for PCT/US2023/069027 mailed Jan. 2, 2025.

Cooper, The classical complement pathway: activation and regulation of the first complement component. Adv Immunol. 1985;37:151-216. doi: 10.1016/s0065-2776(08)60340-5.

Dunkelberger et al., Complement and its role in innate and adaptive immune responses. Cell Res. Jan. 2010;20(1):34-50. doi: 10.1038/cr.2009.139. Epub Dec. 15, 2009.

Nesargikar et al., The complement system: history, pathways, cascade and inhibitors. Eur J Microbiol Immunol (Bp). Jun. 2012;2(2):103-11. doi: 10.1556/EuJMI.2.2012.2.2. Epub Jun. 13, 2012.

* cited by examiner

VH Variant 1

FIG. 2
VII Variant 2

FIG. 3
VH Variant 3

FIG. 4
VH Variant 4

FIG. 5
VH Variant 5

VK Variant 1

FIG. 7
VK Variant 2

FIG. 8
VK Variant 5

FIG. 9

VH Variants

VK Variants

| Amino Acid Position | TNT005 (Parental Antibody) | VK Variant 1 | VK Variant 2 | VK Variant 5 |
|---|---|---|---|---|
| 9 | A | D | D | D |
| 17 | Q | E | E | E |
| 40 | T | P | P | P |
| 46 | K | F | F | F |
| 74 | N | S | S | S |
| 76 | R | S | S | S |
| 77 | V | T | T | T |
| 78 | L | A | A | A |
| 80 | A | A | A | A |
| 83 | F | T | T | T |
| 85 | T | V | V | V |
| 104 | L | V | V | V |

FIG. 10

| antibody | Direct Binding Ab to aC1s EC50 (M) | Competition Binding w/ 50pM Biot-005 IC50 (M) | Classical Pathway Inhibition IC50 (M) |
|---|---|---|---|
| TNT025.001 | 5.96E-11 | 3.99E-11 | 1.63E-09 |
| biotin TNT025.001 | 8.19E-11 | Not Tested | Not Tested |
| humanized VH1/VK1 | 2.007E-10 | 1.23E-10 | 1.3E-09 |
| humanized VH1/VK2 | 8.797E-11 | 9.36E-11 | 1.187E-09 |
| humanized VH1/VK3 | 1.074E-10 | 1.38E-10 | 1.237E-09 |
| humanized VH2/VK1 | 1.374E-10 | 1.44E-10 | 1.234E-09 |
| humanized VH2/VK2 | 1.335E-10 | 1.57E-10 | 1.393E-09 |
| humanized VH2/VK3 | 1.299E-10 | 1.57E-10 | 1.272E-09 |
| humanized VH3/VK1 | 2.69E-10 | 1.73E-10 | 1.27E-09 |
| humanized VH3/VK2 | 1.58E-10 | 1.88E-10 | 1.26E-09 |
| humanized VH3/VK3 | 1.38E-10 | 1.58E-10 | 1.38E-09 |
| humanized VH4/VK1 | 1.52E-10 | 1.92E-10 | 1.35E-09 |
| humanized VH4/VK2 | 1.19E-10 | 1.58E-10 | 1.31E-09 |
| humanized VH4/VK3 | 2.03E-10 | 2.56E-10 | 1.94E-09 |
| humanized VH5/VK1 | 1.33E-10 | 4.49E-11 | 1.06E-09 |
| humanized VH5/VK2 | 1.64E-10 | 1.48E-10 | 1.33E-09 |
| humanized VH5/VK3 | 1.69E-10 | 1.37E-10 | 1.39E-09 |

| Humanized TNT005 Variant | $K_D$ (M) | $K_{on}$ (1/Ms) | $k_{off}$ (1/s) | $R^2$ |
|---|---|---|---|---|
| VH1/Vk1 | 2.277E-10 | 8.641E+05 | 1.967E-04 | 0.996 |
| VH1/Vk2 | 2.078E-10 | 8.177E+05 | 1.699E-04 | 0.996 |
| VH1/Vk3 | 2.169E-10 | 7.795E+05 | 1.691E-04 | 0.996 |
| VH2/Vk1 | 2.508E-10 | 8.324E+05 | 2.088E-04 | 0.994 |
| VH2/Vk2 | 2.059E-10 | 8.354E+05 | 1.720E-04 | 0.997 |
| VH2/Vk3 | 2.080E-10 | 7.979E+05 | 1.660E-04 | 0.996 |
| VH3/Vk2 | 5.850E-10 | 8.379E+05 | 4.901E-04 | 0.997 |
| VH3/Vk1 | 4.572E-10 | 1.030E+06 | 4.710E-04 | 0.996 |

FIG. 15A

ASTKGPSVFPLAPCSRSTSESTAALGCLVKDYFPEPVTVSWNSGALTSGVHTFPAVLQSSGLYSLSSVVTVPSSSLGTKT
YTCNVDHKPSNTKVDKRVESKYGPPCPAPEFEGGPSVFLFPPKDTLMISRTPEVTCVVVDVSQEDPEVQFNWYVD
GVEVHNAKTKPREEQFNSTYRVVSVLTVLHQDWLNGKEYKCKVSNKGLPSSIEKTISKAKGQPREPQVYTLPPSQEEMTK
NQVSLTCLVKGFYPSDIAVEWESNGQPENNYKTTPPVLDSDGSFFLYSRLTVDKSRWQEGNVFSCSVLHEALHSHYTQKS
LSLSLGK (SEQ ID NO: 28)

FIG. 15B

QVQLVQSGAEVKKPGASVKLSCTASGENIKDDYIHWVKQAPGQGLEWIGRIDPADGHTKYAPKFQVKVTITADTSTSTAY
LELSSLRSEDTAVYYCARYGYGREVFDYWGQGTTVTVSSASTKGPSVFPLAPCSRSTSESTAALGCLVKDYFPEPVTVSW
NSGALTSGVHTFPAVLQSSGLYSLSSVVTVPSSSLGTKTYTCNVDHKPSNTKVDKRVESKYGPPCPAPEFEGGPSVF
LFPPKPKDTLMISRTPEVTCVVVDVSQEDPEVQFNWYVDGVEVHNAKTKPREEQFNSTYRVVSVLTVLHQDWLNGKEYKC
KVSNKGLPSSIEKTISKAKGQPREPQVYTLPPSQEEMTKNQVSLTCLVKGFYPSDIAVEWESNGQPENNYKTTPPVLDSD
GSFFLYSRLTVDKSRWQEGNVFSCSVLHEALHSHYTQKSLSLSLGK (SEQ ID NO: 29)

FIG. 15C

DIVLTQSPDSLAVSLGERATISCKASQSVDYDGDSYMNWYQQKPGQPPKLLIYDASNLESGIPARFSGSGSGTDFTLTIS
SLEPEDFAIYYCQQSNEDPWTFGGGTKVEIKRTVAAPSVFIFPPSDEQLKSGTASVVCLLNNFYPREAKVQWKVDNALQS
GNSQESVTEQDSKDSTYSLSSTLTLSKADYEKHKVYACEVTHQGLSSPVTKSFNRGEC (SEQ ID NO: 30)

FIG. 16A

MGWSLILLFLVAVATRVHS QVQLVQSGAEVKKPGASVKLSCTASGFNIKDDYIHWVKQA
PGQGLEWIGRIDPADGHTKYAPKFQVKVTITADTSTSTAYLELSSLRSEDTAVYYCARY
GYGREVEDYWGQGTTVTVSSASTKGPSVFPLAPCSRSTSESTAALGCLVKDYFPEPVTV
SWNSGALTSGVHTFPAVLQSSGLYSLSSVVTVPSSSLGTKTYTCNVDHKPSNTKVDKRV
ESKYGPPCPPCPAPEFEGGPSVFLFPPKPKDTLMISRTPEVTCVVVDVSQEDPEVQFNW
YVDGVEVHNAKTKPREEQFNSTYRVVSVLTVLHQDWLNGKEYKCKVSNKGLPSSIEKTI
SKAKGQPREPQVYTLPPSQEEMTKNQVSLTCLVKGFYPSDIAVEWESNGQPENNYKTTP
PVLDSDGSFFLYSRLTVDKSRWQEGNVFSCSVLHEALHSHYTQKSLSLSLGK (SEQ ID NO:31)

FIG. 16B

MRVPAQLLGLLLLWLPGARC DIVLTQSPDSLAVSLGERATISCKASQSVDYDGDSYMNW
YQQKPGQPPKLLIYDASNLESGIPARFSGSGSGTDFTLTISSLEPEDFAIYYCQQSNED
PWTFGGGTKVEIKRTVAAPSVFIFPPSDEQLKSGTASVVCLLNNFYPREAKVQWKVDNA
LQSGNSQESVTEQDSKDSTYSLSSTLTLSKADYEKHKVYACEVTHQGLSSPVTKSFNRG
EC (SEQ ID NO:32)

ANTI-C1S ANTIBODIES AND METHODS OF USE THEREOF

CROSS-REFERENCE TO RELATED APPLICATIONS

This application is a continuation of U.S. application Ser. No. 16/340,991, filed Apr. 10, 2019, which is a national stage filing under 35 U.S.C. § 371 of International Patent Application Serial No. PCT/US2017/056349, filed Oct. 12, 2017, which claims the benefit under 35 U.S.C. § 119(e) of U.S. Provisional Application Ser. No. 62/407,390, filed Oct. 12, 2016, each of which is incorporated herein by reference in its entirety.

REFERENCE TO A SEQUENCE LISTING SUBMITTED ELECTRONICALLY

The contents of the electronic sequence listing (B155370005US02-SUBSEQ-JRV.xml; Size: 81,574 bytes; and Date of Creation: Sep. 18, 2023) is herein incorporated by reference in its entirety.

BACKGROUND

The complement system is a well-known effector mechanism of the immune response, providing not only protection against pathogens and other harmful agents but also recovery from injury. The complement pathway comprises a number of proteins that typically exist in the body in an inactive form. The classical complement pathway is triggered by activation of the first component of complement, referred to as the C1 complex, which consists of C1q, C1r, and C1s proteins. Upon binding of C1 to an immune complex or other activator, the C1s component, a diisopropyl fluorophosphate (DFP)-sensitive serine protease, cleaves complement components C4 and C2 to initiate activation of the classical complement pathway. The classical complement pathway appears to play a role in many diseases and disorders.

SUMMARY

The present disclosure provides humanized anti-C1s antibodies. The present disclosure provides nucleic acids comprising nucleotide sequences encoding the humanized anti-C1s antibodies; and host cells comprising the nucleic acids. The present disclosure provides compositions comprising the humanized anti-C1s antibodies. The present disclosure provides methods of use of the humanized anti-C1s antibodies.

Some aspects of the present disclosure are directed to an antibody, comprising a heavy chain and a light chain, wherein the heavy chain comprises a heavy chain variable (VH) region and a heavy chain constant region, and the light chain comprises a light chain variable (VL) region; wherein the VL region comprises a VL complementary determining region (CDR) 1, a VL CDR2, and a VL CDR3, and wherein the VH region comprises a VH CDR1, a VH CDR2, and a VH CDR3; wherein the VL CDR1 comprises SEQ ID NO: 1; wherein the VL CDR2 comprises SEQ ID NO: 2; wherein the VL CDR3 comprises SEQ ID NO: 3; wherein the VH CDR1 comprises SEQ ID NO: 4; wherein the VH CDR2 comprises SEQ ID NO: 5; wherein the VH CDR3 comprises SEQ ID NO: 6; wherein the heavy chain constant region comprises an IgG4 constant region, wherein amino acid residue 308 of the heavy chain constant region corresponding to SEQ ID NO: 28 is Leu, and amino acid residue 314 of the heavy chain constant region corresponding to SEQ ID NO: 28 is Ser; and wherein the antibody specifically binds activated C1s.

Certain aspects of the present disclosure are directed to an antibody, comprising a heavy chain and a light chain, wherein the heavy chain comprises a VH region and a heavy chain constant region, and the light chain comprises a VL region; wherein the VL region comprises a VL CDR1, a VL CDR2, and a VL CDR3, and wherein the VH region comprises a VH CDR1, a VH CDR2, and a VH CDR3; wherein the VL CDR1 comprises SEQ ID NO: 1; wherein the VL CDR2 comprises SEQ ID NO: 2; wherein the VL CDR3 comprises SEQ ID NO: 3; wherein the VH CDR1 comprises SEQ ID NO: 4; wherein the VH CDR2 comprises SEQ ID NO: 5; wherein the VH CDR3 comprises SEQ ID NO: 6; wherein the heavy chain constant region comprises SEQ ID NO: 28; and wherein the antibody specifically binds activated C1s.

Other aspects of the present disclosure are directed to an immunoconjugate comprising an antibody disclosed herein.

Other aspects of the present disclosure are directed to a nucleotide or a set of nucleotides encoding an antibody disclosed herein.

Other aspects of the present disclosure are directed to methods of inhibiting a complement pathway in a subject in need thereof, comprising administering to the subject a pharmaceutically effective amount of an antibody, immunoconjugate, or nucleotide disclosed herein.

Other aspects of the present disclosure are directed to methods of treating a complement-mediated disease or disorder in a subject in need thereof, comprising administering to the subject a pharmaceutically effective amount of an antibody, immunoconjugate, or nucleotide disclosed herein.

BRIEF DESCRIPTION OF THE DRAWINGS

FIG. 2 depicts an amino acid sequence of humanized VH variant 2 (SEQ ID NO:12) and a nucleotide sequence (SEQ ID NO:13) encoding same. CDR definitions and protein sequence numbering are shown according to Kabat numbering. CDR nucleotides and protein sequences are underlined.

FIG. 3 depicts an amino acid sequence of humanized VH variant 3 (SEQ ID NO:14) and a nucleotide sequence (SEQ ID NO:15) encoding same. CDR definitions and protein sequence numbering are shown according to Kabat numbering. CDR nucleotides and protein sequences are underlined.

FIG. 4 depicts an amino acid sequence of humanized VH variant 4 (SEQ ID NO:16) and a nucleotide sequence (SEQ ID NO:17) encoding same. CDR definitions and protein sequence numbering are shown according to Kabat numbering. CDR nucleotides and protein sequences are underlined.

FIG. 5 depicts an amino acid sequence of humanized VH variant 5 (SEQ ID NO:18) and a nucleotide sequence (SEQ ID NO:19) encoding same. CDR definitions and protein sequence numbering are shown according to Kabat numbering. CDR nucleotides and protein sequences are underlined.

FIG. 7 depicts an amino acid sequence of humanized Vκ variant 2 (SEQ ID NO:22) and a nucleotide sequence (SEQ ID NO:23) encoding same. CDR definitions and protein sequence numbering are shown according to Kabat numbering. CDR nucleotides and protein sequences are underlined.

FIG. 8 depicts an amino acid sequence of humanized Vκ variant 5 (SEQ ID NO:24) and a nucleotide sequence (SEQ ID NO:25) encoding same. CDR definitions and protein sequence numbering are shown according to Kabat numbering. CDR nucleotides and protein sequences are underlined.

FIG. 9 shows amino acid differences between parental murine anti-activated C1s (anti-aC1s; also known as TNT005) VH (SEQ ID NO: 8) and exemplary humanized VH variants.

FIG. 10 shows amino acid differences between parental murine anti-aC1s VL (SEQ ID NO: 7) and exemplary humanized VL variants.

FIG. 11 shows binding properties of humanized variants of murine anti-aC1s. Data for direct binding to activated C1s ("aC1s"), competition binding with 50 pM biotinylated-anti-aC1s ("Biot-005"), and inhibition of the classical complement pathway, are shown.

FIG. 12 shows binding properties of humanized variants of murine anti-aC1s. Affinity data for binding of humanized variants of murine anti-aC1s are provided.

FIGS. 15A-15C provide amino acid sequences of a VH3/VK2-Fc-sub$_4$. FIG. 15A provides the Fc-sub$_4$ amino acid sequence present in VH3/VK2-Fc-sub$_4$. Amino acid substitutions that enhance FcRn binding are underlined (FIG. 15A). FIGS. 15B and 15C provide the heavy chain (FIG. 15B) and the light chain (FIG. 15C) amino acid sequences of VH3/VK2-Fc-sub$_4$. Variable region CDRs are underlined (FIGS. 15B and 15C), and the heavy chain constant region (Fc domain) is bolded (FIG. 15B).

FIGS. 16A-16B provide amino acid sequences of the full length heavy and light chains of VH3/VK2-Fc-sub$_4$. The signal peptides are bolded and underlined (FIGS. 16A and 16B); the CDRs are underlined (FIGS. 16A and 16B1); and the heavy chain constant region (Fc) is bolded (FIG. 16A). Heavy chain constant region amino acid substitutions that enhance FcRn binding are double-underlined (FIG. 16A).

DEFINITIONS

Figure 1:
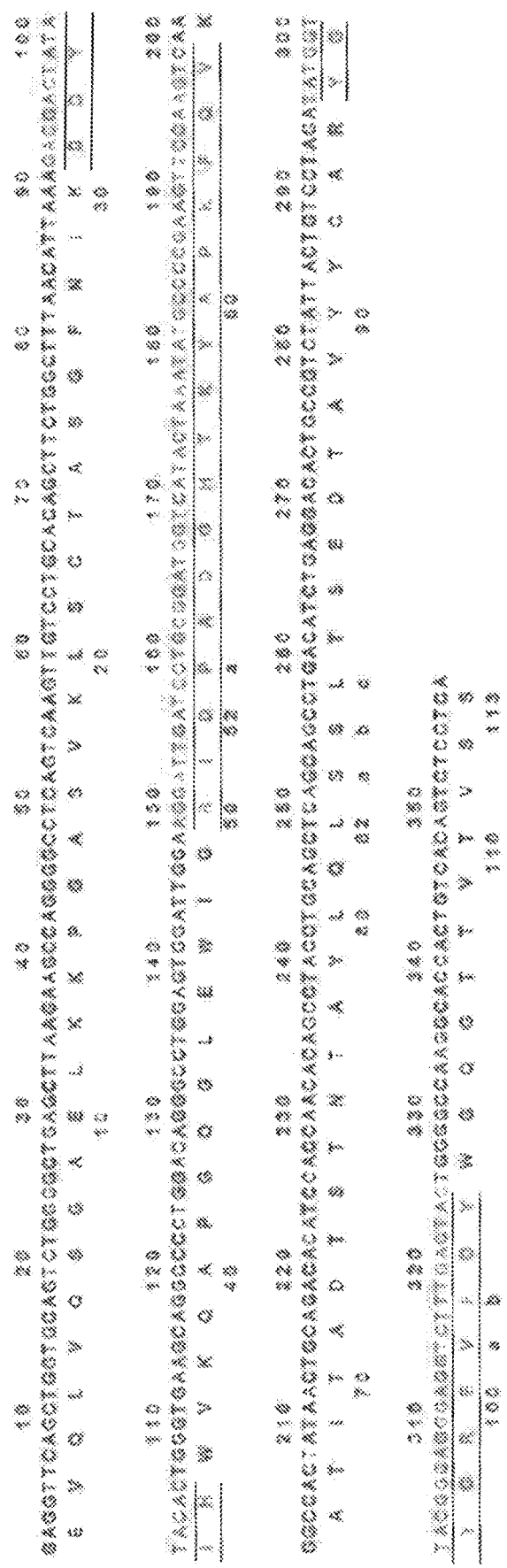
FIG. 1 depicts an amino acid sequence of humanized VH variant 1 (SEQ ID NO:10) and a nucleotide sequence (SEQ ID NO:11) encoding same. CDR definitions and protein sequence numbering are shown according to Kabat numbering. CDR nucleotides and protein sequences are underlined.

The term "complement component C1s" or "C1s," as used herein, refers to a diisopropyl fluorophosphate (DFP)-sensitive serine protease, which cleaves complement components C4 and C2 to initiate activation of the classical complement pathway. The wild-type amino acid sequence for human C1s is provided in Table 1 (SEQ ID NO: 9).

TABLE 1

Sequences

| | |
|---|---|
| Human C1s | EPTMYGEILSPNYPQAYPSEVEKSWDIEVPEGYGIHLYFTHLDIELSENCAYDSVQIISGD TEEGRLCGQRSSNNPHSPIVEEFQVPYNKLQVIFKSDFSNEERFTGFAAYYVATDINECTD FVDVPCSHFCNNFIGGYFCSCPPEYFLHDDMKNCGVNCSGDVFTALIGEIASPNYPKPYPE NSRCEYQIRLEKGFQVVVTLRREDEDVEAADSAGNCLDSLVFVAGDRQFGPYCGHGFPGPL NIETKSNALDIIFQTDLTGQKKGWKLRYHGDPMPCPKEDTPNSVWEPAKAKYVFRDVVQIT CLDGFEVVEGRVGATSFYSTCQSNGKWSNSKLKCQPVDCGIPESIENGKVEDPESTLFGSV IRYTCEEPYYYMENGGGGEYHCAGNGSWVNEVLGPELPKCVPVCGVPREPFEEKQRIIGGS DADIKNFPWQVFFDNPWAGGALINEYWVLTAAHVVEGNREPTMYVGSTSVQTSRLAKSKML TPEHVFIHPGWKLLEVPEGRTNFDNDIALVRLKDPVKMGPTVSPICLPGTSSDYNLMDGDL GLISGWGRTEKRDRAVRLKAARLPVAPLRKCKEVKVEKPTADAEAYVFTPNMICAGGEKGM DSCKGDSGGAFAVQDPNDKTKFYAAGLVSWGPQCGTYGLYTRVKNYVDWIMKTMQENSTPR ED (SEQ ID NO: 9) |
| Human IgG4 Constant Region (Fc) | ASTKGPSVFPLAPCSRSTSESTAALGCLVKDYFPEPVTVSWNSGALTSGVHTFPAVLQSSG LYSLSSVVTVPSSSLGTKTYTCNVDHKPSNTKVDKRVESKYGPPCPSCPAPEFLGGPSVFL FPPKPKDTLMISRTPEVTCVVVDVSQEDPEVQFNWYVDGVEVHNAKTKPREEQFNSTYRVV SVLTVLHQDWLNGKEYKCKVSNKGLPSSIEKTISKAKGQPREPQVYTLPPSQEEMTKNQVS LTCLVKGFYPSDIAVEWESNGQPENNYKTTPPVLDSDGSFFLYSRLTVDKSRWQEGNVFSC SVMHEALHNHYTQKSLSLSLGK (SEQ ID NO: 52) |
| Human IgG4 Constant Region (Fc) | ASTKGPSVFPLAPCSRSTSESTAALGCLVKDYFPEPVTVSWNSGALTSGVHTFPAVLQSSG LYSLSSVVTVPSSSLGTKTYTCNVDHKPSNTKVDKRVESKYGPPCPPCPAPEFEGGPSVFL FPPKPKDTLMISRTPEVTCVVVDVSQEDPEVQFNWYVDGVEVHNAKTKPREEQFNSTYRVV |

TABLE 1-continued

Sequences

| | |
|---|---|
| Variant 1<br>(S241P;<br>L248E) | SVLTVLHQDWLNGKEYKCKVSNKGLPSSIEKTISKAKGQPREPQVYTLPPSQEEMTKNQVS<br>LTCLVKGFYPSDIAVEWESNGQPENNYKTTPPVLDSDGSFFLYSRLTVDKSRWQEGNVFSC<br>SVMHEALHNHYTQKSLSLSLGK (SEQ ID NO: 53) |
| Human IgG4<br>Constant<br>Region (Fc)<br>Variant 2<br>(S241P;<br>L248E;<br>M428L;<br>N434S) | ASTKGPSVFPLAPCSRSTSESTAALGCLVKDYFPEPVTVSWNSGALTSGVHTFPAVLQSSG<br>LYSLSSVVTVPSSSLGTKTYTCNVDHKPSNTKVDKRVESKYGPPCPPCPAPEFEGGPSVEL<br>FPPKPKDTLMISRTPEVTCVVVDVSQEDPEVQFNWYVDGVEVHNAKTKPREEQFNSTYRVV<br>SVLTVLHQDWLNGKEYKCKVSNKGLPSSIEKTISKAKGQPREPQVYTLPPSQEEMTKNQVS<br>LTCLVKGFYPSDIAVEWESNGQPENNYKTTPPVLDSDGSFFLYSRLTVDKSRWQEGNVFSC<br>SVLHEALHSHYTQKSLSLSLGK (SEQ ID NO: 28) |

The terms "antibodies" and "immunoglobulin" include antibodies or immunoglobulins of any isotype, that retain specific binding to antigen. An "antibody" includes, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as VH) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, and FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody. An antigen-binding fragment of an antibody can include any portion of an antibody that retains the ability to bind the target of the antibody. In some embodiments, an antigen-binding fragment of an anti-C1s antibody retains the ability to bind C1s. In some embodiments, an antigen-binding fragment of an antibody comprises 1, 2, 3, 4, 5, or 6 CDRs of the antibody. In some embodiments, an antigen-binding fragment of an antibody comprises 1, 2, 3, 4, 5, or 6 CDRs and 1, 2, 3, 4, 5, 6, 7, or 8 framework regions of the antibody. In some embodiments, an antigen-binding fragment of an antibody comprises a VH region and/or a VL region of the antibody.

The antibodies can be detectably labeled, e.g., with a radioisotope, an enzyme that generates a detectable product, a fluorescent protein, and the like. The antibodies can be further conjugated to other moieties, such as members of specific binding pairs, e.g., biotin (member of biotin-avidin specific binding pair), and the like. The antibodies can also be bound to a solid support, including, but not limited to, polystyrene plates or beads, and the like. Also encompassed by the term are monoclonal antibodies. As used herein, a monoclonal antibody is an antibody produced by a group of identical cells, all of which were produced from a single cell by repetitive cellular replication. That is, the clone of cells only produces a single antibody species. While a monoclonal antibody can be produced using hybridoma production technology, other production methods known to those skilled in the art can also be used (e.g., antibodies derived from antibody phage display libraries). An antibody can be monovalent or bivalent. An antibody can be an Ig monomer, which is a "Y-shaped" molecule that consists of four polypeptide chains: two heavy chains and two light chains connected by disulfide bonds.

The term "monoclonal antibody" ("mAb") refers to a non-naturally occurring antibody molecule of single molecular composition, i.e., antibody molecules whose primary sequences are essentially identical, and which exhibits a single binding specificity and affinity for a particular epitope. A mAb is an example of an isolated antibody. The term "monoclonal antibody" is not limited to antibodies prepared using hybridoma techniques. Rather, monoclonal antibodies, as used herein, can be produced by hybridoma, recombinant, transgenic or other techniques known to those skilled in the art.

The term "humanized immunoglobulin" or "humanized antibody" as used herein refers to an immunoglobulin comprising portions of immunoglobulins of different origin, wherein at least one portion comprises amino acid sequences of human origin. For example, the humanized antibody can comprise portions derived from an immunoglobulin of non-human origin with the requisite specificity, such as a mouse, and from immunoglobulin sequences of human origin (e.g., chimeric immunoglobulin), joined together chemically by conventional techniques (e.g., synthetic) or prepared as a contiguous polypeptide using genetic engineering techniques (e.g., DNA encoding the protein portions of the chimeric antibody can be expressed to produce a contiguous polypeptide chain). Another example of a humanized immunoglobulin is an immunoglobulin containing one or more immunoglobulin chains comprising a CDR derived from an antibody of nonhuman origin and a framework region derived from a light and/or heavy chain of human origin (e.g., CDR-grafted antibodies with or without framework changes). In some embodiments, most or all of the amino acids outside the CDR regions of a non-human antibody are replaced with corresponding amino acids derived from human immunoglobulins. In one embodiment of a humanized form of an antibody, some, most or all of the amino acids outside the CDR regions have been replaced with amino acids from human immunoglobulins, whereas some, most or all amino acids within one or more CDR regions are unchanged. Chimeric or CDR-grafted single chain antibodies are also encompassed by the term humanized immunoglobulin. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194,276 B1; Winter, U.S. Pat. No. 5,225,539; Winter, European Patent No. 0,239,400 B1; Padlan, E. A. et al., European Patent Application No. 0,519,596 A1. See also, Ladner et al., U.S. Pat. No. 4,946,778; Huston, U.S. Pat. No. 5,476,786; and Bird, R. E. et al., Science, 242: 423-426 (1988)), regarding single chain antibodies. Small additions, deletions, insertions, substitutions or modifications of amino acids are permissible as long as they do not abrogate the ability of the antibody to bind to a particular antigen. In particular, conservative amino acid substitutions in one or more framework region of the antibody are within the scope of the present disclosure. A "humanized" antibody retains an antigenic specificity similar to that of the original antibody.

For example, humanized immunoglobulins can be produced using synthetic and/or recombinant nucleic acids to prepare genes (e.g., cDNA) encoding the desired humanized chain. For example, nucleic acid (e.g., DNA) sequences coding for humanized variable regions can be constructed using PCR mutagenesis methods to alter DNA sequences encoding a human or humanized chain, such as a DNA template from a previously humanized variable region (see e.g., Kamman, M., et al., Nucl. Acids Res., 17: 5404 (1989)); Sato, K., et al., Cancer Research, 53: 851-856 (1993); Daugherty, B. L. et al., Nucleic Acids Res., 19(9): 2471-2476 (1991); and Lewis, A. P. and J. S. Crowe, Gene, 101: 297-302 (1991)). Using these or other suitable methods, variants can also be readily produced. For example, cloned variable regions can be mutagenized, and sequences encoding variants with the desired specificity can be selected (e.g., from a phage library; see e.g., Krebber et al., U.S. Pat. No. 5,514,548; Hoogenboom et al., WO 93/06213, published Apr. 1, 1993)).

Humanization of a framework region(s) reduces the risk of the antibody eliciting a human-anti-mouse-antibody (HAMA) response in humans. Art-recognized methods of determining immune response can be performed to monitor a HAMA response in a particular patient or during clinical trials. Patients administered humanized antibodies can be given an immunogenicity assessment at the beginning and throughout the administration of the therapy. The HAMA response is measured, for example, by detecting antibodies to the humanized therapeutic reagent, in serum samples from the patient using a method known to one in the art, including surface plasmon resonance technology (BIA-CORE) and/or solid-phase enzyme-linked immunosorbent assay (ELISA) analysis. In many cases, a humanized anti-C1s antibody disclosed herein does not substantially elicit a HAMA response in a human subject.

Certain amino acids from the human variable region framework residues are selected for substitution based on their possible influence on CDR conformation and/or binding antigen. The unnatural juxtaposition of murine CDR regions with human variable framework region can result in unnatural conformational restraints, which, unless corrected by substitution of certain amino acid residues, lead to loss of binding affinity.

A "chimeric antibody" refers to an antibody in which the variable regions are derived from one species and the constant regions are derived from another species, such as an antibody in which the variable regions are derived from a mouse antibody and the constant regions are derived from a human antibody.

The "light chains" of antibodies (immunoglobulins) from any vertebrate species can be assigned to one of two clearly distinct types, called kappa and lambda, based on the amino acid sequences of their constant domains. Depending on the amino acid sequence of the constant domain of their heavy chains, immunoglobulins can be assigned to different classes.

There are five major classes of immunoglobulins: IgA, IgD, IgE, IgG, and IgM, and several of these classes can be further divided into subclasses (isotypes), e.g., IgG1, IgG2, IgG3, IgG4, IgA, and IgA2. The subclasses can be further divided into types, e.g., IgG2a and IgG2b. "Isotype" refers to the antibody class or subclass (e.g., IgM or IgG1) that is encoded by the heavy chain constant region genes.

An "anti-antigen" antibody refers to an antibody that binds specifically to the antigen. For example, an anti-C1s antibody binds specifically to C1s.

An "antigen-binding portion" of an antibody (also called an "antigen-binding fragment") refers to one or more fragments of an antibody that retain the ability to bind specifically to the antigen bound by the whole antibody.

As used herein, the term "affinity" refers to the equilibrium constant for the reversible binding of two agents (e.g., an antibody and an antigen) and is expressed as a dissociation constant ($K_D$). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1,000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. A humanized anti-C1s antibody of the present disclosure binds specifically to an epitope within a complement C1s protein. "Specific binding" refers to binding with an affinity of at least about $10^{-7}$ M or greater, e.g., $5 \times 10^{-7}$ M, $10^{-8}$ M, $5 \times 10^{-8}$ M, and greater. "Non-specific binding" refers to binding with an affinity of more than about $10^{-7}$ M, e.g., binding with an affinity of $10^{-6}$ M, $10^{-5}$ M, $10^{-4}$ M, etc. In some embodiments, the anti-C1s antibody specifically binds to both the active and the inactive forms of C1s, e.g., with similar affinity. In certain embodiments, the anti-C1s antibody specifically binds to the active form of C1s and does not specifically bind to the inactive form of C1s.

As used herein, the term "CDR" or "complementarity determining region" is intended to mean the non-contiguous antigen combining sites found within the variable region of both heavy and light chain polypeptides. CDRs have been described by Kabat et al., J. Biol. Chem. 252:6609-6616 (1977); Kabat et al., U.S. Dept. of Health and Human Services, "Sequences of proteins of immunological interest" (1991) (also referred to herein as Kabat 1991); by Chothia et al., J. Mol. Biol. 196:901-917 (1987) (also referred to herein as Chothia 1987); and MacCallum et al., J. Mol. Biol. 262:732-745 (1996), where the definitions include overlapping or subsets of amino acid residues when compared against each other. Nevertheless, application of either definition to refer to a CDR of an antibody or grafted antibodies or variants thereof is intended to be within the scope of the term as defined and used herein. The amino acid residues, which encompass the CDRs, as defined by each of the above cited references are set forth below in Table 2 as a comparison. The CDRs depicted in FIGS. 1-8 were defined in accordance with Kabat 1991.

TABLE 2

CDR Definitions

| | Kabat[1] | Chothia[2] | MacCallum[3] |
|---|---|---|---|
| $V_H$ CDR-1 | 31-35 | 26-32 | 30-35 |
| $V_H$ CDR-2 | 50-65 | 53-55 | 47-58 |
| $V_H$ CDR-3 | 95-102 | 96-101 | 93-101 |
| $V_L$ CDR-1 | 24-34 | 26-32 | 30-36 |
| $V_L$ CDR-2 | 50-56 | 50-52 | 46-55 |
| $V_L$ CDR-3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra As used herein, the terms "CDR-L1," "CDR-L2," and "CDR-L3" refer, respectively, to the first, second, and third CDRs in a light chain variable region. As used herein, the terms "CDR-H1," "CDR-H2," and "CDR-H3" refer, respectively, to the first, second, and third CDRs in a heavy chain variable region. As used herein, the terms "CDR-1," "CDR-2," and "CDR-3" refer, respectively, to the first, second and third CDRs of either chain's variable region.

As used herein, the term "framework" or "FR", when used in reference to an antibody variable region, is intended to mean all amino acid residues outside the CDR regions within the variable region of an antibody. A variable region framework is generally a discontinuous amino acid sequence between about 100-120 amino acids in length but is intended to reference only those amino acids outside of the CDRs. As used herein, the term "framework region" is intended to mean each domain of the framework that is separated by the CDRs. A light chain variable region (VL region) can have four framework regions: FR1, FR2, FR3, and FR4. Similarly, a heavy chain variable region (VH) can have four framework regions: FR1, FR2, FR3, and FR4.

The term "Fc domain" or "Fc region" as used herein, means functional FcR (e.g., FcRn) binding partners, unless otherwise specified. The Fc domain is the portion of a polypeptide which corresponds to the Fc domain of native Ig. A native Fc domain forms a homodimer with another Fc domain. In one embodiment, the "Fc region" refers to the portion of a single Ig heavy chain beginning in the hinge region just upstream of the papain cleavage site (i.e. residue 216 in IgG, taking the first residue of heavy chain constant region to be 114) and ending at the C-terminus of the antibody. In some embodiments, a complete Fc domain comprises at least a hinge domain, a CH2 domain, and a CH3 domain. The Fc region of an Ig constant region, depending on the Ig isotype can include the CH2, CH3, and CH4 domains, as well as the hinge region. In certain embodiments, the Fc region comprises SEQ ID NO: 52 (Table 3). In certain embodiments, the Fc region comprises SEQ ID NO: 53 (Table 3). In certain embodiments, the Fc region comprises SEQ ID NO: 28 (Table 3).

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In some embodiments, the antibody will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated antibody includes the antibody in situ within recombinant cells since at least one component of the antibody's natural environment will not be present. In some instances, isolated antibody will be prepared by at least one purification step.

The terms "polypeptide," "peptide," and "protein," used interchangeably herein, refer to a polymeric form of amino acids of any length, which can include genetically coded and non-genetically coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; and the like. A polypeptide, peptide, or protein can be naturally occurring or recombinant.

As used herein, the terms "treatment," "treating," "treat," and the like, refer to obtaining a desired pharmacologic and/or physiologic effect. The effect can be prophylactic in terms of completely or partially preventing a disease or symptom thereof and/or can be therapeutic in terms of a partial or complete cure for a disease and/or adverse effect attributable to the disease, e.g., reducing or ameliorating one or more symptoms of the disease. "Treatment," as used herein, covers any treatment of a disease in a mammal, particularly in a human, and includes: (a) preventing the disease from occurring in a subject which can be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, murines (rats, mice), non-human primates, humans, canines, felines, ungulates (e.g., equines, bovines, ovines, porcines, caprines), etc. Also encompassed by these terms are any animal that has a complement system, such as mammals, fish, and some invertebrates. As such these terms include complement system-containing mammal, fish, and invertebrate companion animals, agricultural animals, work animals, zoo animals, and lab animals.

A "therapeutically effective amount," "pharmaceutically effective amount," "effective amount," or "efficacious amount" refers to the amount of an anti-complement C1s antibody that, when administered to a mammal or other subject for treating a disease, is sufficient to effect such treatment for the disease. The "therapeutically effective amount" will vary depending on the anti-complement C1s antibody, the disease and its severity and the age, weight, etc., of the subject to be treated.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples. The term "biological sample" includes urine, saliva, cerebrospinal fluid, interstitial fluid, ocular fluid, synovial fluid, blood fractions such as plasma and serum, and the like. The term "biological sample" also includes solid tissue samples, tissue culture samples, and cellular samples.

The term "substitution," as used herein, refers to a difference between a given sequence and a reference sequence. "Substitution" is not limited to a particular method of arriving at the recited sequence. "Substitution" can be contrasted with "deleted," which indicates that one or more amino acids or nucleotides are missing in a given sequence relative to a reference sequence. In both cases, a given sequence can be said to have a substituted or deleted amino acid or nucleotide regardless of the origin of the sequence. For example, a given sequence can be said to have a substitution at position 100 relative to a reference sequence, even though the given sequence was created de novo, e.g., synthetically, and not through mutation of the reference sequence. In some embodiments, a substitution can comprise more than one amino acid replacing a single amino acid.

The terms "cross competes" and "cross competition," as used herein, refer to the ability of an antibody to compete for binding to a target antigen with a reference antibody. Any methods known in the art can be used to determine whether an antibody cross competes with a reference antibody. For example, BIAcore analysis, ELISA assays, or flow cytometry can be used to demonstrate cross-competition with the antibodies of the current disclosure. The ability of a test antibody to inhibit the binding of an antibody to human C1s demonstrates that the test antibody can compete with a reference antibody for binding to human C1s. In some embodiments, an antibody that cross competes with a reference antibody for binding to an antigen, e.g., human C1s, binds the same epitope as the reference antibody. In some embodiments, an antibody that cross competes with a reference antibody for binding to an antigen, e.g., human C1s, binds an epitope that is near or adjacent to the epitope recognized by the reference antibody. In some embodiments, an antibody that cross competes with a reference antibody for binding to an antigen, e.g., human C1s, binds an epitope that is distal to the epitope recognized by the reference antibody; however, binding of the antibody to the distal epitope is sufficient to disrupt the binding ability of the reference antibody to the antigen. An antibody binds the same epitope as a reference antibody if the antibody interacts with amino acid residues on the antigen which are the same as or overlap with the amino acids on the antigen that interact with the reference antibody.

Before the present disclosure is further described, it is to be understood that this disclosure is not limited to particular embodiments described, as such can, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges can independently be included in the smaller ranges, and are also encompassed within the disclosure, subject to any specifically excluded limit in the stated range. Where the stated range includes one or both of the limits, ranges excluding either or both of those included limits are also included in the disclosure. In addition, the term "about" is used herein to mean approximately, roughly, around, or in the regions of. When the term "about" is used in conjunction with a numerical range, it modifies that range by extending the boundaries above and below the numerical values set forth. Thus, "about 10-20" means "about 10 to about 20." In general, the term "about" can modify a numerical value above and below the stated value by a variance of, e.g., 10 percent, up or down (higher or lower).

Unless defined otherwise, all technical and scientific terms used herein have the same meaning as commonly understood by one of ordinary skill in the art to which this disclosure belongs. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure. Although any methods and materials similar or equivalent to those described herein can also be used in the practice or testing of the present disclosure, the preferred methods and materials are now described. All publications mentioned herein are incorporated herein by reference to disclose and describe the methods and/or materials in connection with which the publications are cited.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects of the disclosure, which can be had by reference to the specification as a whole. Accordingly, the terms defined immediately below are more fully defined by reference to the specification in its entirety.

It must be noted that as used herein and in the appended claims, the singular forms "a," "an," and "the" include plural referents unless the context clearly dictates otherwise. Thus, for example, reference to "a humanized anti-C1s antibody" includes a plurality of such antibodies and reference to "the framework region" includes reference to one or more framework regions and equivalents thereof known to those skilled in the art, and so forth. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

Furthermore, "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided.

It is appreciated that certain features of the disclosure, which are, for clarity, described in the context of separate embodiments, can also be provided in combination in a single embodiment. Conversely, various features of the disclosure, which are, for brevity, described in the context of a single embodiment, can also be provided separately or in any suitable sub-combination. All combinations of the embodiments pertaining to the disclosure are specifically embraced by the present disclosure and are disclosed herein just as if each and every combination was individually and explicitly disclosed. In addition, all sub-combinations of the various embodiments and elements thereof are also specifically embraced by the present disclosure and are disclosed herein just as if each and every such sub-combination was individually and explicitly disclosed herein.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided can be different from the actual publication dates which can need to be independently confirmed.

DETAILED DESCRIPTION

The present disclosure provides an antibody, e.g., a humanized antibody, that binds complement C1s protein (i.e., an anti-complement C1s antibody, also referred to herein as a "anti-C1s antibody," a "C1s antibody," and a "subject antibody") and a nucleic acid comprising a nucleotide sequence that encodes such an antibody. In some aspects, the anti-C1s antibody specifically binds active C1s. In certain embodiments, the anti-C1s antibody does not specifically bind inactive C1s. In some aspects, the anti-C1s antibody is a humanized antibody. In other aspects, the anti-C1s antibody of the present disclosure has one or more improved pharmacokinetic properties, e.g., improved half-life, stability, etc. In certain aspects, the anti-C1s antibody of the present disclosure can be administered subcutaneously. The present disclosure also provides a composition comprising an antibody, e.g., a humanized anti-C1s antibody, of the present disclosure. The present disclosure provides methods of producing and using antibodies, nucleic acids, and compositions of the present disclosure. The present disclosure provides methods of treating a complement-mediated disease or disorder, involving administering an antibody, e.g., a humanized anti-C1s antibody, of the present disclosure.

Anti-Complement C1s Antibodies

The present disclosure provides anti-complement C1s antibodies, e.g., humanized anti-complement C1s antibodies, and pharmaceutical compositions comprising such antibodies. Complement C1s is an attractive target as it is upstream in the complement cascade and has a narrow range of substrate specificity. Of interest in some cases is an antibody that specifically binds the activated form of C1s, e.g., where the antibody does not substantially bind the inactive form of C1s.

The present disclosure provides an anti-complement C1s antibody, e.g., a humanized anti-complement C1s antibody, comprising:

a) a heavy chain comprising: i) a VH region comprising the amino acid sequence: (Q/E)VQL(V/Q)QSGAE(V/L)KKPGASVK(L/V)SC(T/A)ASGFNIKDDYIHWV(K/R)QAPGQ GLEWIGRIDPADGHTKYAPKFQVK(V/A)TITADTST(S/N)TAY(L/M)(E/Q)LSSL(R/T)SEDT AVYYCARYGYGREVFDYWGQGTTVTVSS (SEQ ID NO:26); and ii) an Fc region comprising an amino acid sequence having at least 98% amino acid sequence identity with the amino acid sequence set forth in SEQ ID NO:28, wherein amino acid 308 is Leu and amino acid 314 is Ser; and b) a light chain comprising: i) a VL region comprising the amino acid sequence: DIVLTQSPDSLAVSLGER-ATISCKASQSVDYDGDSYMNWYQQK(T/P)GQ-PPK(I/L)LIYDA SNLESGIPARFSGSGSGTDFTLTI-SSLE(E/P)EDFA(I/V)YYCQQSNEDPWTFGGGTK-VEIK (SEQ ID NO:27); and ii) a light chain constant region.

In certain aspects of the present disclosure, the anti-C1s antibody comprises a heavy chain constant region, comprising an Fc region. In some embodiments, the heavy chain constant region comprises an immunoglobulin constant region, e.g., a human IgG constant region (e.g., IgG Fc), or a variant thereof. In some embodiments, the heavy chain constant region of the anti-C1s antibody is derived from a human immunoglobulin. In some embodiments, heavy chain constant region of the anti-C1s antibody comprises an IgG4 Fc or a variant thereof.

In some embodiments, the heavy chain Fc of the anti-C1s antibody comprises an amino acid sequence having at least about 80%, at least about 85%, at least about 90%, at least about 95%, at least about 96%, at least about 97%, at least about 98%, or at least about 99% sequence identity with human IgG4 Fc (SEQ ID NO: 52) or SEQ ID NO: 28, wherein amino acid 308 is Leu and amino acid 314 is Ser. In some embodiments, the heavy chain Fc of the anti-C1s antibody comprises an amino acid sequence having at least about 98% sequence identity with human IgG4 Fc (SEQ ID NO: 52) or SEQ ID NO: 28, wherein amino acid 308 is Leu and amino acid 314 is Ser. In some aspects, the Fc region comprises an amino acid sequence at least 99% identical to SEQ ID NO: 52 or SEQ ID NO: 28, wherein amino acid 308 is Leu and amino acid 314 is Ser. In other aspects, the Fc region for an anti-C1s antibody comprises, consists essentially of, or consists of SEQ ID NO: 28.

In certain aspects, an anti-C1s antibody of the present disclosure has one or more improved pharmacokinetics, e.g., longer half-life, stability, etc, compared to wild type Fc region (SEQ ID NO: 52). In certain embodiments, the anti-C1s antibodies comprising a heavy chain Fc region comprising SEQ ID NO: 28 have a longer half-life than comparable antibodies having a wild type Fc region, e.g., a human IgG4 Fc. In other embodiments, the anti-C1s antibodies are more stable following subcutaneous administration than comparable antibodies having a wild type Fc region, e.g., a human IgG4 Fc. Accordingly, in some aspects, an anti-C1s antibody of the present disclosure can be administered subcutaneously.

In some embodiments, the heavy chain Fc of the anti-C1s antibody comprises a substitution relative to human IgG4 Fc. In some embodiments, the anti-C1s antibody comprises an Fc having at least about 98% sequence identity to human IgG4 Fc. In certain embodiments, the anti-C1s antibody comprises an Fc, wherein the amino acid residue corresponding to amino acid 108 of SEQ ID NO: 28, when properly aligned, is a proline (e.g., a S241P variant of human IgG4). In certain embodiments, the anti-C1s antibody comprises an Fc, wherein the amino acid residue corresponding to amino acid 115 of SEQ ID NO: 28, when properly aligned, is a glutamic acid (e.g., a L248E variant of human IgG4). In certain embodiments, the anti-C1s antibody comprises an Fc, wherein the amino acid residue corresponding to amino acid 308 of SEQ ID NO: 28, when properly aligned, is a leucine (e.g., a M428L variant of human IgG4). In certain embodiments, the anti-C1s antibody comprises an Fc, wherein the amino acid residue corresponding to amino acid 314 of SEQ ID NO: 28, when properly aligned, is a serine (e.g., a N434S variant of human IgG4).

In some embodiments, the anti-C1s antibody comprises an Fc, wherein: (a) the amino acid residue corresponding to amino acid 108 of SEQ ID NO: 28, when properly aligned, is a proline; (b) the amino acid residue corresponding to amino acid 115 of SEQ ID NO: 28, when properly aligned, is a glutamic acid; (c) the amino acid residue corresponding to amino acid 308 of SEQ ID NO: 28, when properly aligned, is a leucine; (d) the amino acid residue corresponding to amino acid 314 of SEQ ID NO: 28, when properly aligned, is a serine; (e) or any combination of (a), (b), (c), and (d). In some embodiments, the anti-C1s antibody comprises an Fc, wherein: (a) the amino acid residue corresponding to amino acid 108 of SEQ ID NO: 28, when properly aligned, is a proline; (b) the amino acid residue corresponding to amino acid 115 of SEQ ID NO: 28, when properly aligned, is a glutamic acid; (c) the amino acid residue corresponding to amino acid 308 of SEQ ID NO: 28, when properly aligned, is a leucine; and (d) the amino acid residue corresponding to amino acid 314 of SEQ ID NO: 28, when properly aligned, is a serine.

In some embodiments, the Fc of the anti-C1s antibody has a greater binding affinity to an Fc receptor, e.g., FcRn, than human IgG4.

In some embodiments, the anti-C1s antibody, e.g., the humanized anti-C1s antibody, comprises an Fc comprising the amino acid sequence set forth in SEQ ID NO:28. In some embodiments, the anti-C1s antibody, e.g., the humanized anti-C1s antibody, comprises: a) an Fc comprising the amino acid sequence set forth in SEQ ID NO:28; and b) a light chain comprising a human Vκ constant region.

Variable Regions

In some embodiments, an antibody of the present disclosure comprises a heavy chain and a light chain, wherein the heavy chain comprises a heavy chain variable (VH) region and a heavy chain constant region, and the light chain comprises a light chain variable (VL) region; wherein the VL region comprises a VL complementary determining region (CDR) 1 comprising SEQ ID NO: 1, a VL CDR2 comprising SEQ ID NO: 2, and a VL CDR3 comprising SEQ ID NO: 3, and wherein the VH region comprises a VH CDR1 comprising SEQ ID NO: 4, a VH CDR2 comprising SEQ ID NO: 5, and a VH CDR3 comprising SEQ ID NO: 6; wherein the heavy chain constant region comprises an IgG4 constant region, wherein amino acid residue 308 of the heavy chain constant region corresponding to SEQ ID NO: 28 is a leucine, and amino acid residue 314 of the heavy chain constant region corresponding to SEQ ID NO: 28 is a serine; and wherein the antibody specifically binds activated C1s. In some embodiments, amino acid residue 108 of the heavy chain constant region corresponding to SEQ ID NO: 28 is a proline. In some embodiments, amino acid residue 115 of the heavy chain constant region corresponding to SEQ ID NO: 28 is a glutamic acid.

In some embodiments, an antibody of the present disclosure comprises a heavy chain and a light chain, wherein the heavy chain comprises a VH region and a heavy chain constant region, and the light chain comprises a VL region; wherein the VL region comprises a VL CDR1 comprising SEQ ID NO: 1, a VL CDR2 comprising SEQ ID NO: 2, and a VL CDR3 comprising SEQ ID NO: 3, and wherein the VH region comprises a VH CDR1 comprising SEQ ID NO: 4, a VH CDR2 comprising SEQ ID NO: 5, and a VH CDR3 comprising SEQ ID NO: 6; wherein the heavy chain constant region comprises SEQ ID NO: 28; and wherein the antibody specifically binds activated C1s.

In some embodiments, the antibody is a human antibody. In some embodiments, the antibody is a humanized antibody. In some embodiments, the antibody is a chimeric antibody. In some embodiments, the antibody is a murine antibody.

In some embodiments, the antibody is a monoclonal antibody. In some embodiments, the antibody is a recombinant antibody. In some embodiments, the antibody is a synthetic antibody.

In some cases, an anti-C1s antibody of the present disclosure inhibits C1s-mediated cleavage of complement component C4. In some embodiments, the anti-C1s antibody inhibits enzymatic activity of the serine-protease domain of C1s. In some cases, an anti-C1s antibody of the present disclosure inhibits C1s-mediated cleavage of complement component C2. In some cases, an anti-C1s antibody of the present disclosure inhibits C1s-mediated cleavage of C4 and C2. In some embodiments, the anti-C1s antibody of the present disclosure depletes C1s/aC1s from circulation.

In some embodiments, the anti-C1s antibody is a humanized antibody. In some cases, a humanized anti-C1s antibody of the present disclosure includes at least one humanized $V_H$ framework region. In some cases, an anti-C1s antibody of the present disclosure includes at least one humanized $V_L$ framework region. In some cases, an anti-C1s antibody of the present disclosure includes at least one humanized $V_H$ framework region and at least one humanized $V_L$ framework region.

In some cases, an anti-C1s antibody, e.g., a humanized anti-C1s antibody, of the present disclosure includes VL CDRs present in the following amino acid sequence: DIVLTQSPASLAVSLGQRATISCKASQSVDYDGDS-YM- NWYQQKTGQPPKILIYDASNLES GIPARFSGSG-SGTDFTLNIHPVEEEDAAIYYCQQSNEDPWTFGGGT KLEIK (SEQ ID NO: 7). In some cases, a humanized anti-C1s antibody of the present disclosure includes VH CDRs present in the following amino acid sequence: EVQLQQSGAELVRPGASVKLSCTASGFNIKDDYIH-WVKQRPEQGLEWIGRIDPADGHTK YAPKFQVKATI-TADTSSNTAYLQLSSLTSEDTAVYYCARYGYGREV-FDYWGQGTTLTVS S (SEQ ID NO: 8). In some cases, an anti-C1s antibody, e.g., a humanized anti-C1s antibody of the present disclosure includes VL CDRs present in SEQ ID NO: 7 and VH CDRs present in SEQ ID NO: 8.

In some embodiments, the anti-C1s antibody comprises one or more VL CDRs present in SEQ ID NO: 22. In some embodiments, the anti-C1s antibody comprises a VL CDR1 present in SEQ ID NO: 22. In some embodiments, the anti-C1s antibody comprises a VL CDR2 present in SEQ ID NO: 22. In some embodiments, the anti-C1s antibody comprises a VL CDR3 present in SEQ ID NO: 22. In some embodiments, the anti-C1s antibody comprises one or more VH CDRs present in SEQ ID NO: 14. In some embodiments, the anti-C1s antibody comprises a VH CDR1 present in SEQ ID NO: 14. In some embodiments, the anti-C1s antibody comprises a VH CDR2 present in SEQ ID NO: 14. In some embodiments, the anti-C1s antibody comprises a VH CDR3 present in SEQ ID NO: 14.

In some embodiments, the anti-C1s antibody comprises one or more VL CDRs present in SEQ ID NO: 30. In some embodiments, the anti-C1s antibody comprises a VL CDR1 present in SEQ ID NO: 30. In some embodiments, the anti-C1s antibody comprises a VL CDR2 present in SEQ ID NO: 30. In some embodiments, the anti-C1s antibody comprises a VL CDR3 present in SEQ ID NO: 30. In some embodiments, the anti-C1s antibody comprises one or more VH CDRs present in SEQ ID NO: 29. In some embodiments, the anti-C1s antibody comprises a VH CDR1 present in SEQ ID NO: 29. In some embodiments, the anti-C1s antibody comprises a VH CDR2 present in SEQ ID NO: 29. In some embodiments, the anti-C1s antibody comprises a VH CDR3 present in SEQ ID NO: 29.

In certain embodiments, the ant-C1s antibody comprises a VL CDR1 (CDR-L1) comprising SEQ ID NO:1: KASQSVDYDGDSYMN. In some embodiments, the ant-C1s antibody comprises a VL CDR1 (CDR-L1) comprising SEQ ID NO: 33: SQSVDYDGDSY. In some embodiments, the ant-C1s antibody comprises a VL CDR1 (CDR-L1) comprising SEQ ID NO: 39: DSYMNWY.

In certain embodiments, the ant-C1s antibody comprises a VL CDR2 (CDR-L2) comprising SEQ ID NO:2: DASNLES. In some embodiments, the ant-C1s antibody comprises a VL CDR2 (CDR-L2) comprising SEQ ID NO: 34: DAS. In some embodiments, the ant-C1s antibody comprises a VL CDR2 (CDR-L2) comprising SEQ ID NO: 40: ILIYDASNLE.

In certain embodiments, the ant-C1s antibody comprises a VL CDR3 (CDR-L3) comprising SEQ ID NO:3: QQSNEDPWT. In some embodiments, the anti-C1s antibody comprises a VL CDR3 (CDR-L3) comprising SEQ ID NO: 35: SNEDPW. In some embodiments, the ant-C1s antibody comprises a VL CDR3 (CDR-L3) comprising SEQ ID NO: 41: QQSNEDPW.

In certain embodiments, the ant-C1s antibody comprises a VH CDR1 (CDR-H1) comprising SEQ ID NO:4: DDYIH. In some embodiments, the ant-C1s antibody comprises a VH CDR1 (CDR-H1) comprising SEQ ID NO: 36: GFNIKDD. In some embodiments, the ant-C1s antibody comprises a VH CDR1 (CDR-H1) comprising SEQ ID NO: 42: KDDYIH.

In certain embodiments, the ant-C1s antibody comprises a VH CDR2 (CDR-H2) comprising SEQ ID NO:5: RIDPADGHTKYAPKFQV. In some embodiments, the anti-C1s antibody comprises a VH CDR2 (CDR-H2) comprising SEQ ID NO: 37: ADG. In some embodiments, the anti-C1s antibody comprises a VH CDR2 (CDR-H2) comprising SEQ ID NO: 43: WIGRIDPADGHTK.

In certain embodiments, the ant-C1s antibody comprises a VH CDR3 (CDR-H3) comprising SEQ ID NO:6: YGYGREVFDY. In some embodiments, the anti-C1s antibody comprises a VH CDR3 (CDR-H3) comprising SEQ ID NO: 38: GYGREVFD. In some embodiments, the anti-C1s antibody comprises a VH CDR3 (CDR-H3) comprising SEQ ID NO: 44: ARYGYGREVFD.

In some cases, an anti-C1s antibody, e.g., a humanized anti-C1s antibody, of the present disclosure comprises a light chain variable region comprising CDR amino acid sequences SEQ ID NO:1, SEQ ID NO:2, and SEQ ID NO:3 (CDR-L1, CDR-L2, and CDR-L3, respectively).

In some embodiments, an anti-C1s antibody of the present disclosure comprises a heavy chain variable region comprising CDR amino acid sequences SEQ ID NO:4, SEQ ID NO:5, and SEQ ID NO:6 (CDR-H1, CDR-H2, and CDR-H3, respectively).

In some cases, an anti-C1s antibody, e.g., a humanized anti-C1s antibody, of the present disclosure comprises a VH region comprising the following sequence:

(Q/E)VQL(V/Q)QSGAE(V/L)KKPGASVK(L/V)SC(T/A)ASGFNIKDDYIHWV(K/R)Q APGQGLEWIGRIDPADGHTKYAPKFQVK(V/A)TITADTST(S/N)TAY(L/M)(E/Q)LSSL(R/T)SEDTAVYYCARYGYGREVFDYWGQGTTVTVSS (SEQ ID NO:26).

In some cases, an anti-C1s antibody, e.g., a humanized anti-C1s antibody, of the present disclosure comprises a VH region comprising an amino acid sequence having at least 80%, at least 85%, at least 90%, at least 95%, at least 98%, at least 99%, or 100%, amino acid sequence identity to an amino acid sequence of Table 3. In certain embodiments, the VH region of the antibody comprises an amino acid sequence selected from the group consisting of SEQ ID NOs: 10, 12, 14, 16, and 18 (Table 3). In some embodiments, the VH region of the antibody comprises SEQ ID NO:14.

TABLE 3

Variable Heavy Chain Variants

| Variant | Variable Heavy | Mature Heavy Chain |
|---|---|---|
| Parental Murine anti-C1s VH | EVQLQQSGAELVRPGASV KLSCTASGFNIKDDYIHW VKQRPEQGLEWIGRIDPA DGHTKYAPKFQVKATITA DTSSNTAYLQLSSLTSED TAVYYCARYGYGREVEDY WGQGTTLTVSS (SEQ ID NO: 8) | EVQLQQSGAELVRPGASVKLSCTASGFNIKDDYIHWVKQRPEQGLEWIG RIDPADGHTKYAPKFQVKATITADTSSNTAYLQLSSLTSEDTAVYYCAR YGYGREVEDYWGQGTTLTVSSASTKGPSVFPLAPCSRSTSESTAALGCL VKDYFPEPVTVSWNSGALTSGVHTFPAVLQSSGLYSLSSVVTVPSSSLG TKTYTCNVDHKPSNTKVDKRVESKYGPPCPPCPAPEFEGGPSVFLFPPK PKDTLMISRTPEVTCVVVDVSQEDPEVQFNWYVDGVEVHNAKTKPREEQ FNSTYRVVSVLTVLHQDWLNGKEYKCKVSNKGLPSSIEKTISKAKGQPR EPQVYTLPPSQEEMTKNQVSLTCLVKGFYPSDIAVEWESNGQPENNYKT TPPVLDSDGSFFLYSRLTVDKSRWQEGNVFSCSVLHEALHSHYTQKSLS LSLGK (SEQ ID NO: 53) |
| VH1 | EVQLVQSGAELKKPGASV KLSCTASGFNIKDDYIHW VKQAPGQGLEWIGRIDPA | EVQLVQSGAELKKPGASVKLSCTASGFNIKDDYIHWVKQAPGQGLEWIG RIDPADGHTKYAPKFQVKATITADTSTNTAYLQLSSLTSEDTAVYYCAR YGYGREVFDYWGQGTTVTVSSASTKGPSVFPLAPCSRSTSESTAALGCL |

TABLE 3-continued

Variable Heavy Chain Variants

| Variant | Variable Heavy | Mature Heavy Chain |
|---|---|---|
| | DGHTKYAPKFQVKATITA<br>DTSTNTAYLQLSSLTSED<br>TAVYYCARYGYGREVEDY<br>WGQGTTVTVSS (SEQ<br>ID NO: 10) | VKDYFPEPVTVSWNSGALTSGVHTFPAVLQSSGLYSLSSVVTVPSSSLG<br>TKTYTCNVDHKPSNTKVDKRVESKYGPPCPPCPAPEFEGGPSVFLFPPK<br>PKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKT<br>TPPVLDSDGSFFLYSRLTVDKSRWQEGNVFSCSVLHEALHSHYTQKSLS<br>LSLGK (SEQ ID NO: 46) |
| VH2 | EVQLVQSGAEVKKPGASV<br>KLSCTASGFNIKDDYIHW<br>VKQAPGQGLEWIGRIDPA<br>DGHTKYAPKFQVKATITA<br>DTSTNTAYLELSSLRSED<br>TAVYYCARYGYGREVEDY<br>WGQGTTVTVSS (SEQ<br>ID NO: 12) | EVQLVQSGAEVKKPGASVKLSCTASGFNIKDDYIHWVKQAPGQGLEWIG<br>RIDPADGHTKYAPKFQVKATITADTSTNTAYLELSSLRSEDTAVYYCAR<br>YGYGREVEDYWGQGTTVTVSSASTKGPSVFPLAPCSRSTSESTAALGCL<br>VKDYFPEPVTVSWNSGALTSGVHTFPAVLQSSGLYSLSSVVTVPSSSLG<br>TKTYTCNVDHKPSNTKVDKRVESKYGPPCPPCPAPEFEGGPSVFLFPPK<br>PKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKT<br>TPPVLDSDGSFFLYSRLTVDKSRWQEGNVFSCSVLHEALHSHYTQKSLS<br>LSLGK (SEQ ID NO: 47) |
| VH3 | QVQLVQSGAEVKKPGASV<br>KLSCTASGFNIKDDYIHW<br>VKQAPGQGLEWIGRIDPA<br>DGHTKYAPKFQVKVTITA<br>DTSTSTAYLELSSLRSED<br>TAVYYCARYGYGREVEDY<br>WGQGTTVTVSS (SEQ<br>ID NO: 14) | QVQLVQSGAEVKKPGASVKLSCTASGFNIKDDYIHWVKQAPGQGLEWIG<br>RIDPADGHTKYAPKFQVKVTITADTSTSTAYLELSSLRSEDTAVYYCAR<br>YGYGREVFDYWGQGTTVTVSSASTKGPSVFPLAPCSRSTSESTAALGCL<br>VKDYFPEPVTVSWNSGALTSGVHTFPAVLQSSGLYSLSSVVTVPSSSLG<br>TKTYTCNVDHKPSNTKVDKRVESKYGPPCPPCPAPEFEGGPSVFLFPPK<br>PKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKT<br>TPPVLDSDGSFFLYSRLTVDKSRWQEGNVFSCSVLHEALHSHYTQKSLS<br>LSLGK (SEQ ID NO: 29) |
| VH4 | QVQLVQSGAEVKKPGASV<br>KVSCTASGFNIKDDYIHW<br>VRQAPGQGLEWIGRIDPA<br>DGHTKYAPKFQVKVTITA<br>DTSTSTAYMELSSLRSED<br>TAVYYCARYGYGREVEDY<br>WGQGTTVTVSS (SEQ<br>ID NO: 16) | QVQLVQSGAEVKKPGASVKVSCTASGFNIKDDYIHWVRQAPGQGLEWIG<br>RIDPADGHTKYAPKFQVKVTITADTSTSTAYMELSSLRSEDTAVYYCAR<br>YGYGREVFDYWGQGTTVTVSSASTKGPSVFPLAPCSRSTSESTAALGCL<br>VKDYFPEPVTVSWNSGALTSGVHTFPAVLQSSGLYSLSSVVTVPSSSLG<br>TKTYTCNVDHKPSNTKVDKRVESKYGPPCPPCPAPEFEGGPSVFLFPPK<br>PKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKT<br>TPPVLDSDGSFFLYSRLTVDKSRWQEGNVFSCSVLHEALHSHYTQKSLS<br>LSLGK (SEQ ID NO: 48) |
| VH5 | QVQLVQSGAEVKKPGASV<br>KVSCAASGFNIKDDYIHW<br>VRQAPGQGLEWIGRIDPA<br>DGHTKYAPKFQVKVTITA<br>DTSTSTAYMELSSLRSED<br>TAVYYCARYGYGREVEDY<br>WGQGTTVTVSS (SEQ<br>ID NO: 18) | QVQLVQSGAEVKKPGASVKVSCAASGFNIKDDYIHWVRQAPGQGLEWIG<br>RIDPADGHTKYAPKFQVKVTITADTSTSTAYMELSSLRSEDTAVYYCAR<br>YGYGREVFDYWGQGTTVTVSSASTKGPSVFPLAPCSRSTSESTAALGCL<br>VKDYFPEPVTVSWNSGALTSGVHTFPAVLQSSGLYSLSSVVTVPSSSLG<br>TKTYTCNVDHKPSNTKVDKRVESKYGPPCPPCPAPEFEGGPSVFLFPPK<br>PKDTLMISRTPEVTCVVVDVSQEDPEVQFNWYVDGVEVHNAKTKPREEQ<br>FNSTYRVVSVLTVLHQDWLNGKEYKCKVSNKGLPSSIEKTISKAKGQPR<br>EPQVYTLPPSQEEMTKNQVSLTCLVKGFYPSDIAVEWESNGQPENNYKT<br>TPPVLDSDGSFFLYSRLTVDKSRWQEGNVFSCSVLHEALHSHYTQKSLS<br>LSLGK (SEQ ID NO: 49) |

In some cases, an anti-C1s antibody, e.g., a humanized anti-C1s antibody, of the present disclosure comprises a VH region comprising an amino acid sequence having at least 80%, at least 85%, at least 90%, at least 95%, at least 98%, at least 99%, or 100%, amino acid sequence identity to the amino acid sequence depicted in FIG. 1, and set forth in SEQ ID NO:10, where amino acid 1 is Glu, amino acid 5 is Val, amino acid 11 is Leu, amino acid 12 is Lys, amino acid 13 is Lys, amino acid 20 is Leu, amino acid 23 is Thr, amino acid 38 is Lys, amino acid 40 is Ala, amino acid 42 is Gly, amino acid 67 is Ala, amino acid 75 is Thr, amino acid 76 is Asn, amino acid 80 is Leu, amino acid 81 is Gln, amino acid 83 is Thr, and amino acid 109 is Val, where the numbering of the amino acids is as depicted in FIG. 1.

In some cases, an anti-C1s antibody, e.g., a humanized anti-C1s antibody, of the present disclosure comprises a VH region comprising the amino acid sequence depicted in FIG. 1, and set forth in SEQ ID NO:10.

Figure 2:
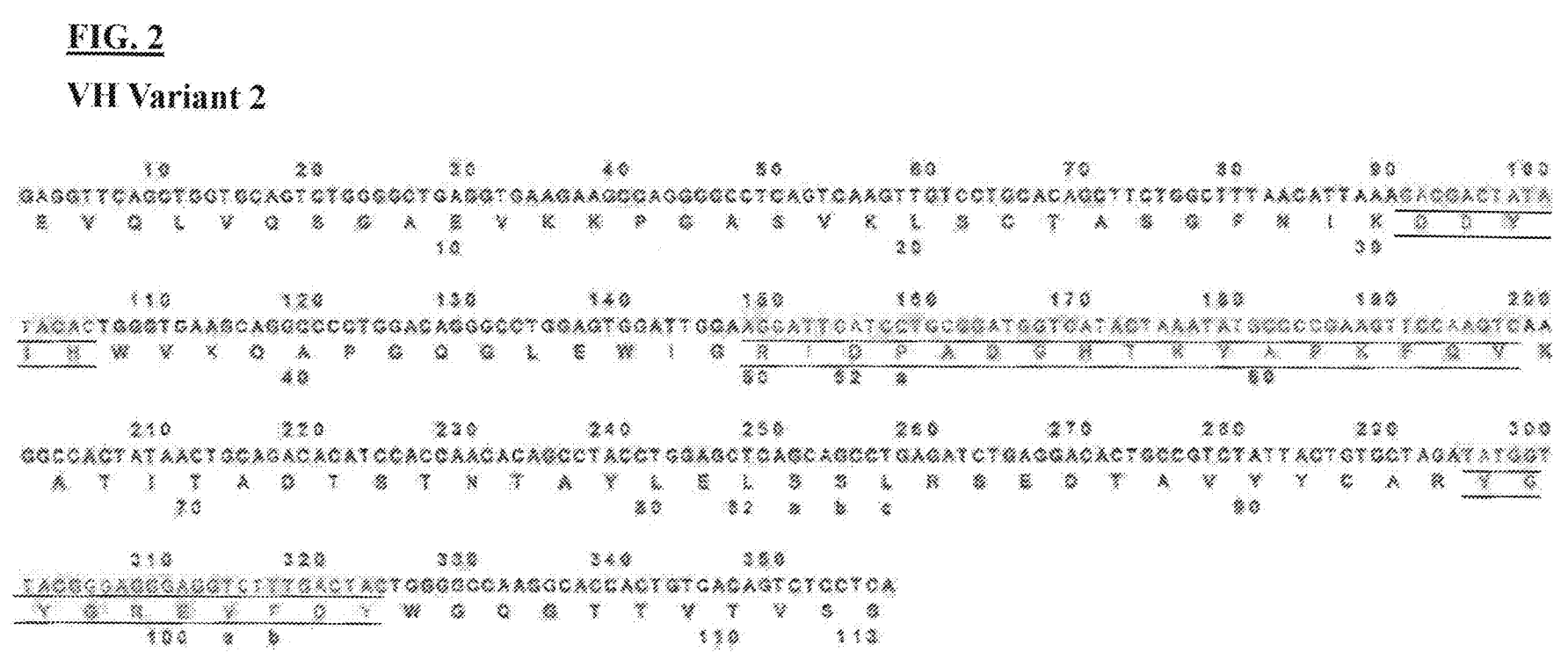

In some cases, an anti-C1s antibody, e.g., a humanized anti-C1s antibody, of the present disclosure comprises a VH region comprising an amino acid sequence having at least 80%, at least 85%, at least 90%, at least 95%, at least 98%, at least 99%, or 100%, amino acid sequence identity to the amino acid sequence depicted in FIG. 2 and set forth in SEQ ID NO:12, where amino acid 1 is Glu, amino acid 5 is Val, amino acid 11 is Val, amino acid 12 is Lys, amino acid 13 is Lys, amino acid 20 is Leu, amino acid 23 is Thr, amino acid 38 is Lys, amino acid 40 is Ala, amino acid 42 is Gly, amino acid 67 is Ala, amino acid 75 is Thr, amino acid 76 is Asn, amino acid 80 is Leu, amino acid 81 is Glu, amino acid 83 is Arg, and amino acid 109 is Val, where the numbering of the amino acids is as depicted in FIG. 2.

In some cases, an anti-C1s antibody, e.g., a humanized anti-C1s antibody, of the present disclosure comprises a VH region comprising the amino acid sequence depicted in FIG. 2, and set forth in SEQ ID NO:12.

Figure 3:
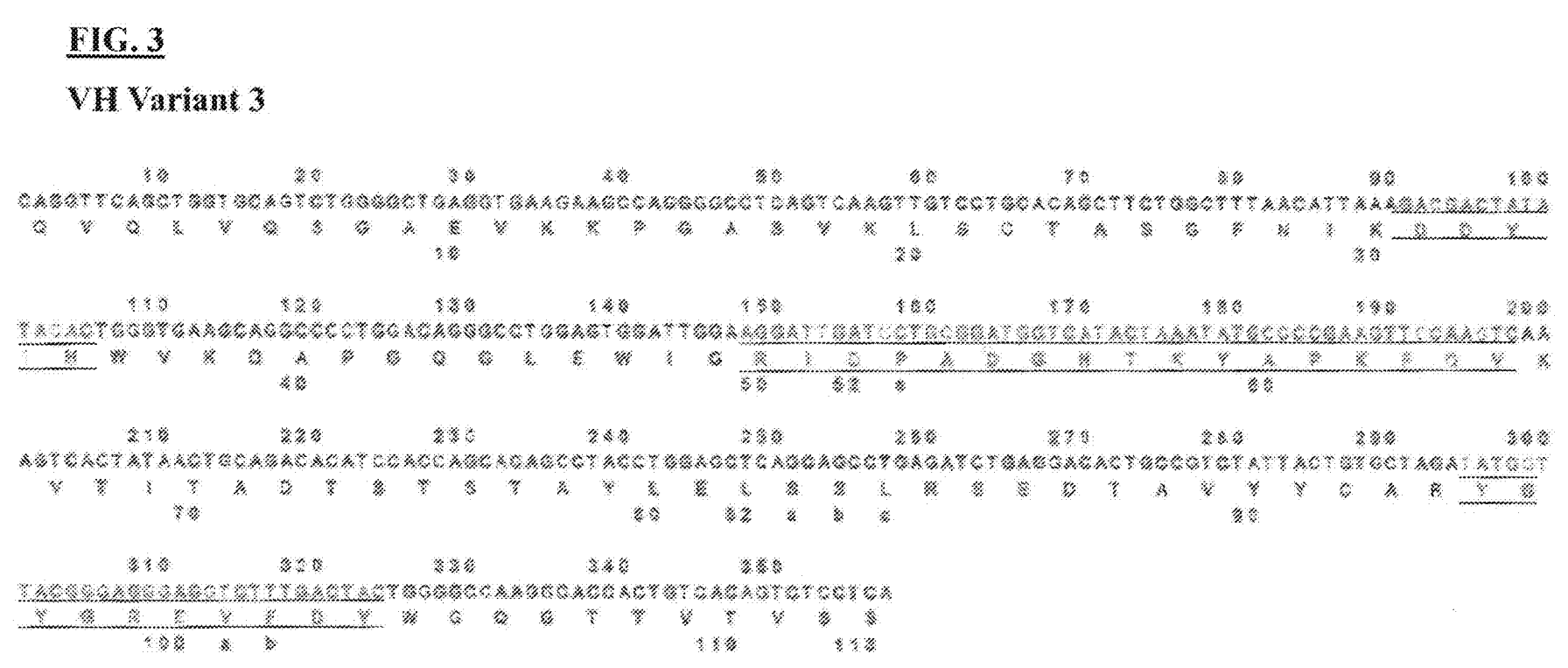

In some cases, an anti-C1s antibody, e.g., a humanized anti-C1s antibody, of the present disclosure comprises a VH region comprising an amino acid sequence having at least 80%, at least 85%, at least 90%, at least 95%, at least 98%, at least 99%, or 100%, amino acid sequence identity to the amino acid sequence depicted in FIG. 3 and set forth in SEQ ID NO:14, where amino acid 1 is Gln, amino acid 5 is Val, amino acid 11 is Val, amino acid 12 is Lys, amino acid 13 is Lys, amino acid 20 is Leu, amino acid 23 is Thr, amino acid 38 is Lys, amino acid 40 is Ala, amino acid 42 is Gly, amino acid 67 is Val, amino acid 75 is Thr, amino acid 76 is Ser, amino acid 80 is Leu, amino acid 81 is Glu, amino acid 83 is Arg, and amino acid 109 is Val, where the numbering of the amino acids is as depicted in FIG. 3.

In some cases, an anti-C1s antibody, e.g., a humanized anti-C1s antibody, of the present disclosure comprises a VH region comprising the amino acid sequence depicted in FIG. 3, and set forth in SEQ ID NO:14.

Figure 4:
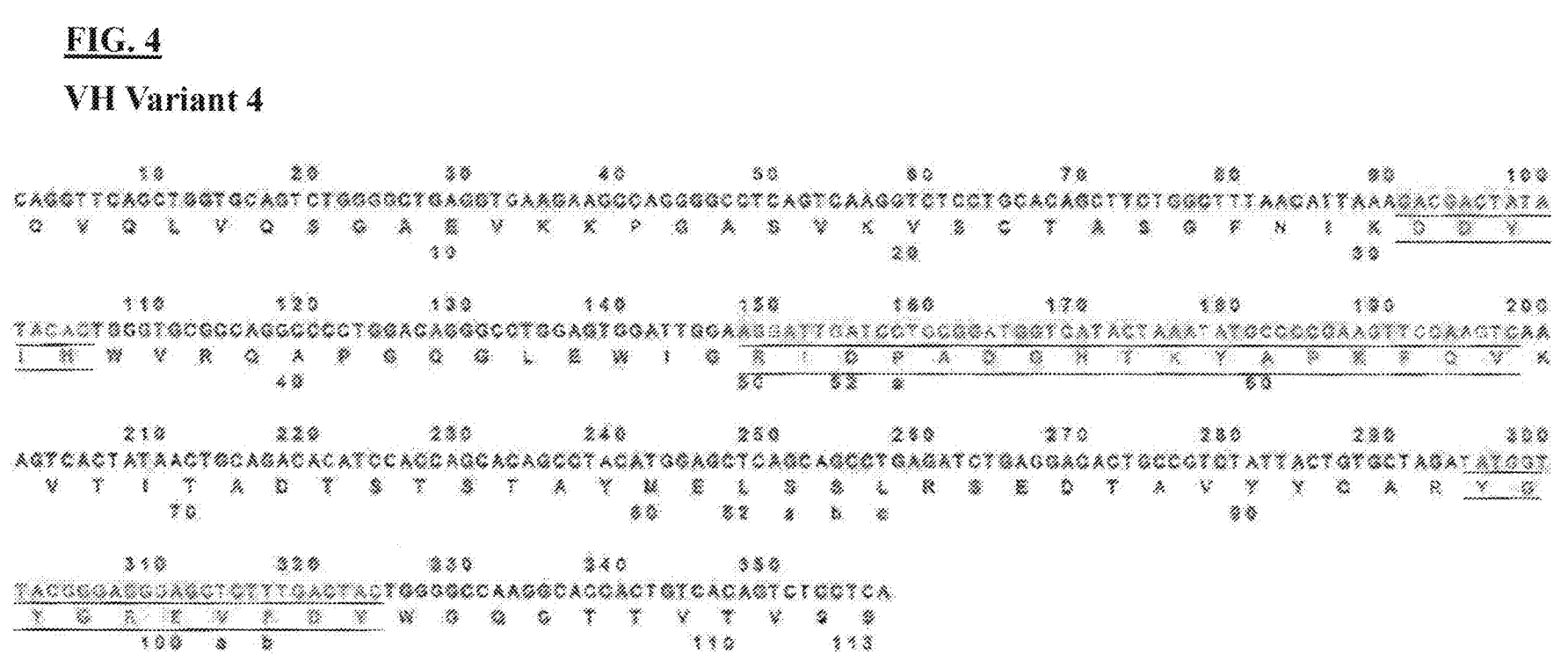

In some cases, an anti-C1s antibody, e.g., a humanized anti-C1s antibody, of the present disclosure comprises a VH region comprising an amino acid sequence having at least 80%, at least 85%, at least 90%, at least 95%, at least 98%, at least 99%, or 100%, amino acid sequence identity to the amino acid sequence depicted in FIG. 4 and set forth in SEQ ID NO:16, where amino acid 1 is Gln, amino acid 5 is Val, amino acid 11 is Val, amino acid 12 is Lys, amino acid 13 is Lys, amino acid 20 is Val, amino acid 23 is Thr, amino acid 38 is Arg, amino acid 40 is Ala, amino acid 42 is Gly, amino acid 67 is Val, amino acid 75 is Thr, amino acid 76 is Ser, amino acid 80 is Met, amino acid 81 is Glu, amino acid 83 is Arg, and amino acid 109 is Val, where the numbering of the amino acids is as depicted in FIG. 4.

In some cases, an anti-C1s antibody, e.g., a humanized anti-C1s antibody, of the present disclosure comprises a VH region comprising the amino acid sequence depicted in FIG. 4, and set forth in SEQ ID NO:16.

Figure 5:
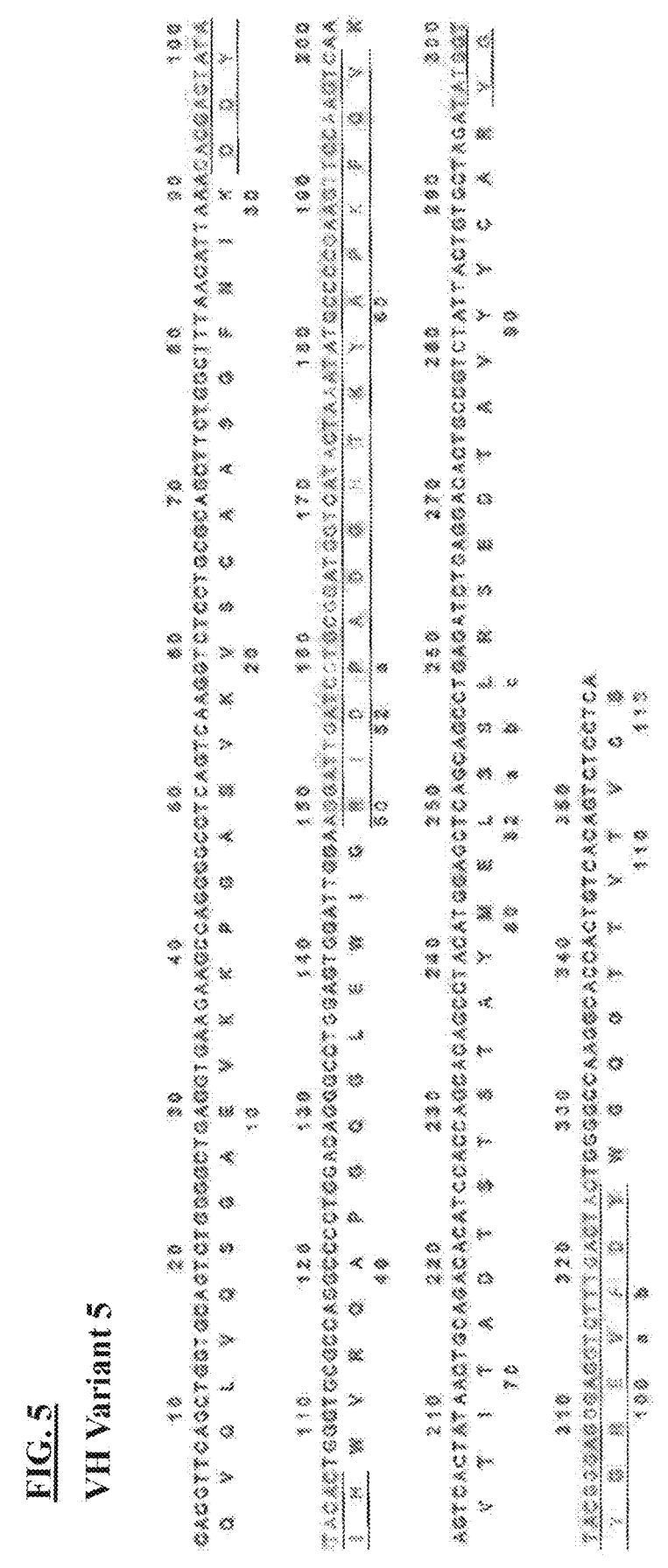

In some cases, an anti-C1s antibody, e.g., a humanized anti-C1s antibody, of the present disclosure comprises a VH region comprising an amino acid sequence having at least 80%, at least 85%, at least 90%, at least 95%, at least 98%, at least 99%, or 100%, amino acid sequence identity to the amino acid sequence depicted in FIG. 5 and set forth in SEQ ID NO:18, where amino acid 1 is Gln, amino acid 5 is Val, amino acid 11 is Val, amino acid 12 is Lys, amino acid 13 is Lys, amino acid 20 is Val, amino acid 23 is Ala, amino acid 38 is Arg, amino acid 40 is Ala, amino acid 42 is Gly, amino acid 67 is Val, amino acid 75 is Thr, amino acid 76 is Ser, amino acid 80 is Met, amino acid 81 is Glu, amino acid 83 is Arg, and amino acid 109 is Val, where the numbering of the amino acids is as depicted in FIG. 5.

In some cases, an anti-C1s antibody, e.g., a humanized anti-C1s antibody, of the present disclosure comprises a VH region comprising the amino acid sequence depicted in FIG. 5, and set forth in SEQ ID NO:18.

In some cases, an anti-C1s antibody, e.g., a humanized anti-C1s antibody, of the present disclosure comprises a VL region comprising the following sequence:
DIVLTQSPDSLAVSLGERATISCKASQSVDYDGDS-YMNWYQQK(T/P)GQPPK(I/L)LIYDASNLESGIPAR-FSGSGSGTDFTLTISSLE(E/P)EDFA(I/V)YYCQQSN-EDPWTFGGGTK VEIK (SEQ ID NO:27).

In some cases, an anti-C1s antibody, e.g., a humanized anti-C1s antibody, of the present disclosure comprises a VL region comprising an amino acid sequence having at least 80%, at least 85%, at least 90%, at least 95%, at least 98%, at least 99%, or 100%, amino acid sequence identity to an amino acid sequence of Table 4. In certain embodiments, the VL region of the antibody comprises an amino acid sequence selected from the group consisting of SEQ ID NOs: 20, 22, and 24 (Table 4). In some embodiments, the VL region of the antibody comprises SEQ ID NO: 22.

TABLE 4

Variable Light Chain Variants

| Variant | Variable Light | Mature Light Chain |
| --- | --- | --- |
| Parental Murine anti-C1s VL | DIVLTQSPASLAVSLGQRATIS CKASQSVDYDGDSYMNWYQQKT GQPPKILIYDASNLESGIPARF SGSGSGTDFTLNIHPVEEEDAA IYYCQQSNEDPWTFGGGTKLEI K (SEQ ID NO: 7) | DIVLTQSPASLAVSLGQRATISCKASQSVDYDGDSYMNWYQQKTGQ PPKILIYDASNLESGIPARFSGSGSGTDFTLNIHPVEEEDAAIYYC QQSNEDPWTFGGGTKLEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSENRGEC (SEQ ID NO: 54) |
| Vκ1 | DIVLTQSPDSLAVSLGERATIS CKASQSVDYDGDSYMNWYQQKT GQPPKILIYDASNLESGIPARF SGSGSGTDFTLTISSLEEEDFA IYYCQQSNEDPWTFGGGTKVEI K (SEQ ID NO: 20) | DIVLTQSPDSLAVSLGERATISCKASQSVDYDGDSYMNWYQQKTGQ PPKILIYDASNLESGIPARFSGSGSGTDFTLTISSLEEEDFAIYYC QQSNEDPWTFGGGTKVEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSENRGEC (SEQ ID NO: 50) |
| Vκ2 | DIVLTQSPDSLAVSLGERATIS CKASQSVDYDGDSYMNWYQQKP GQPPKILIYDASNLESGIPARF SGSGSGTDFTLTISSLEPEDFA IYYCQQSNEDPWTFGGGTKVEI K (SEQ ID NO: 22) | DIVLTQSPDSLAVSLGERATISCKASQSVDYDGDSYMNWYQQKPGQ PPKILIYDASNLESGIPARFSGSGSGTDFTLTISSLEPEDFAIYYC QQSNEDPWTFGGGTKVEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSENRGEC (SEQ ID NO: 30) |
| Vκ5 | DIVLTQSPDSLAVSLGERATIS CKASQSVDYDGDSYMNWYQQKP GQPPKLLIYDASNLESGIPARF SGSGSGTDFTLTISSLEPEDFA VYYCQQSNEDPWTFGGGTKVEI K (SEQ ID NO: 24) | DIVLTQSPDSLAVSLGERATISCKASQSVDYDGDSYMNWYQQKPGQ PPKLLIYDASNLESGIPARFSGSGSGTDFTLTISSLEPEDFAVYYC QQSNEDPWTFGGGTKVEIKRTVAAPSVFIFPPSDEQLKSGTASVVC LLNNFYPREAKVQWKVDNALQSGNSQESVTEQDSKDSTYSLSSTLT LSKADYEKHKVYACEVTHQGLSSPVTKSENRGEC (SEQ ID NO: 51) |

Figure 6:
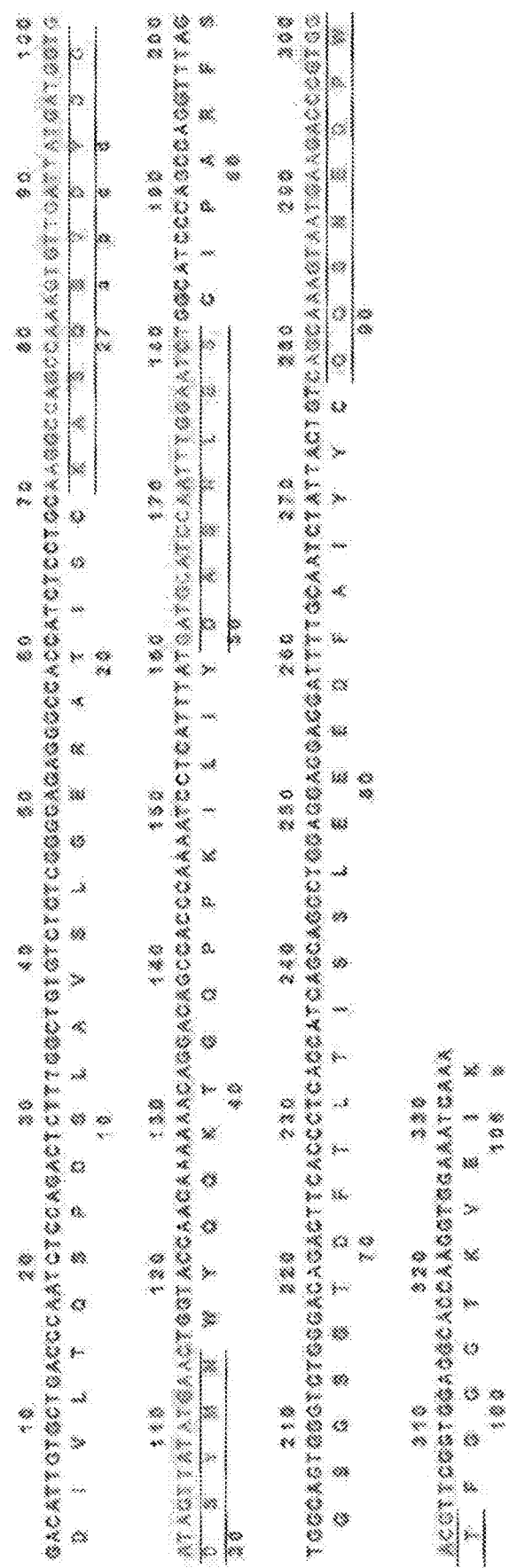
FIG. 6 depicts an amino acid sequence of humanized Vκ variant 1 (SEQ ID NO:20) and a nucleotide sequence (SEQ ID NO:21) encoding same. CDR definitions and protein sequence numbering are shown according to Kabat numbering. CDR nucleotides and protein sequences are underlined.

In some cases, an anti-C1s antibody, e.g., a humanized anti-C1s antibody, of the present disclosure comprises a VL region comprising an amino acid sequence having at least 80%, at least 85%, at least 90%, at least 95%, at least 98%, at least 99%, or 100%, amino acid sequence identity to the amino acid sequence depicted in FIG. 6, and set forth in SEQ ID NO:20, where amino acid 9 is Asp, amino acid 17 is Glu, amino acid 40 is Thr, amino acid 46 is Ile, amino acid 74 is Thr, amino acid 76 is Ser, amino acid 77 is Ser, amino acid 78 is Leu, amino acid 80 is Glu, amino acid 83 is Phe, amino acid 85 is Ile, and amino acid 104 is Val, where the numbering of the amino acids is as depicted in FIG. 6.

In some cases, an anti-C1s antibody, e.g., a humanized anti-C1s antibody, of the present disclosure comprises a VL region comprising the amino acid sequence depicted in FIG. 6, and set forth in SEQ ID NO:20.

Figure 7:
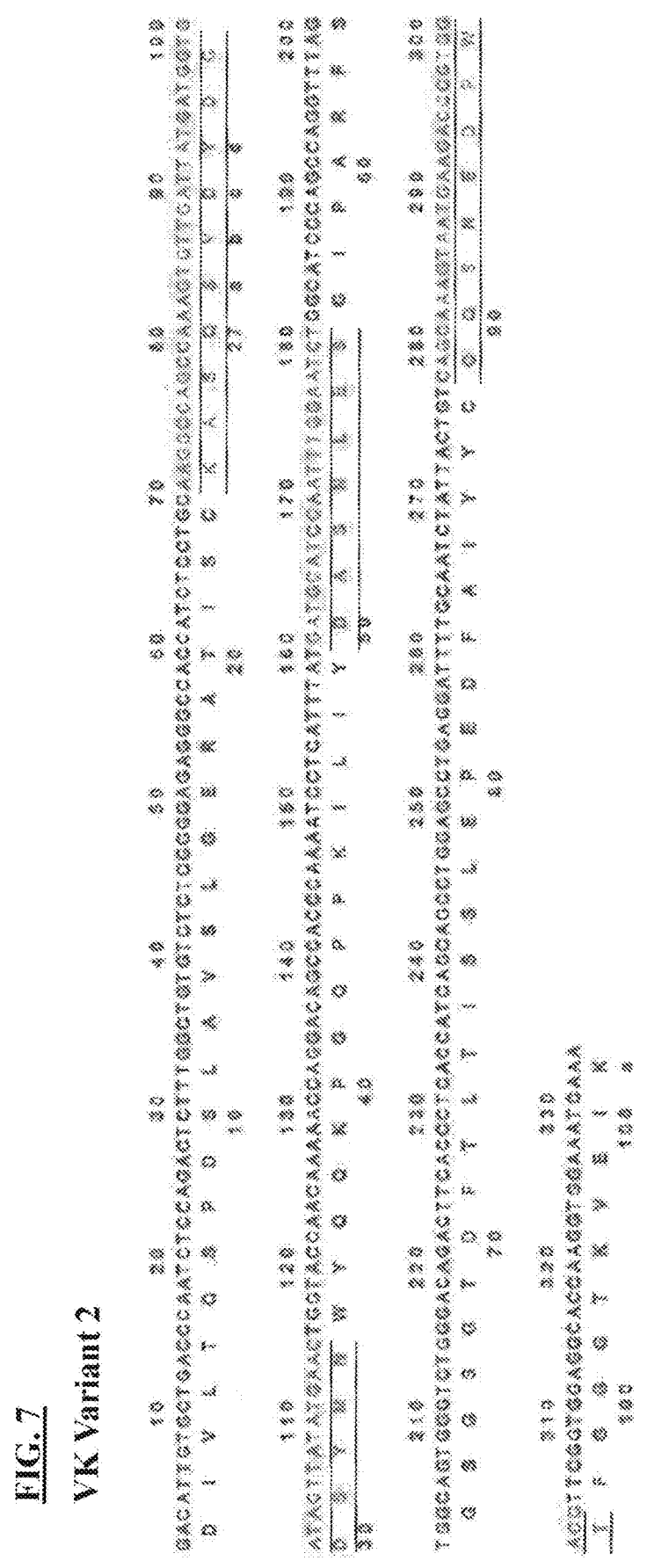

In some cases, an anti-C1s antibody, e.g., a humanized anti-C1s antibody, of the present disclosure comprises a VL region comprising an amino acid sequence having at least 80%, at least 85%, at least 90%, at least 95%, at least 98%, at least 99%, or 100%, amino acid sequence identity to the amino acid sequence depicted in FIG. 7, and set forth in SEQ ID NO:22, where amino acid 9 is Asp, amino acid 17 is Glu, amino acid 40 is Pro, amino acid 46 is Ile, amino acid 74 is Thr, amino acid 76 is Ser, amino acid 77 is Ser, amino acid 78 is Leu, amino acid 80 is Pro, amino acid 83 is Phe, amino acid 85 is Ile, and amino acid 104 is Val, where the numbering of the amino acids is as depicted in FIG. 7.

In some cases, an anti-C1s antibody, e.g., a humanized anti-C1s antibody, of the present disclosure comprises a VL region comprising the amino acid sequence depicted in FIG. 7, and set forth in SEQ ID NO:22.

Figure 8:
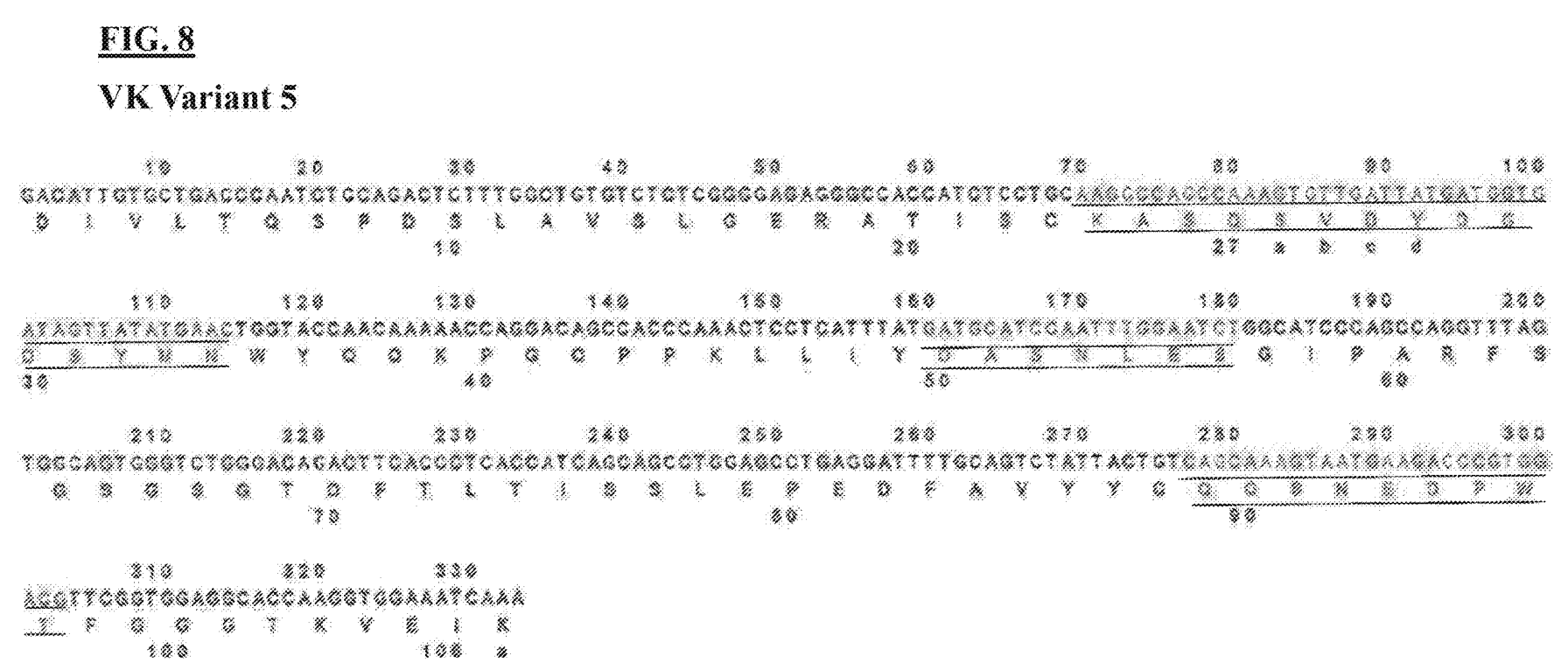

In some cases, an anti-C1s antibody, e.g., a humanized anti-C1s antibody, of the present disclosure comprises a VL region comprising an amino acid sequence having at least 80%, at least 85%, at least 90%, at least 95%, at least 98%, at least 99%, or 100%, amino acid sequence identity to the amino acid sequence depicted in FIG. 8 and set forth in SEQ ID NO:24, where amino acid 9 is Asp, amino acid 17 is Glu, amino acid 40 is Pro, amino acid 46 is Leu, amino acid 74 is Thr, amino acid 76 is Ser, amino acid 77 is Ser, amino acid 78 is Leu, amino acid 80 is Pro, amino acid 83 is Phe, amino acid 85 is Val, and amino acid 104 is Val, where the numbering of the amino acids is as depicted in FIG. 8.

In some cases, an anti-C1s antibody, e.g., a humanized anti-C1s antibody, of the present disclosure comprises a VL region comprising the amino acid sequence depicted in FIG. 8, and set forth in SEQ ID NO:24.

In some cases, an anti-C1s antibody, e.g., a humanized anti-C1s antibody, of the present disclosure comprises: a) a VH variant 1 amino acid sequence depicted in FIG. 1 and as set forth in SEQ ID NO: 10; and b) a VL variant 1 amino acid sequence depicted in FIG. 6 and as set forth in SEQ ID NO: 20.

In some cases, an anti-C1s antibody, e.g., a humanized anti-C1s antibody, of the present disclosure comprises: a) a VH variant 1 amino acid sequence depicted in FIG. 1 and as set forth in SEQ ID NO:10; and b) a VL variant 2 amino acid sequence depicted in FIG. 7 and as set forth in SEQ ID NO:22.

In some cases, an anti-C1s antibody, e.g., a humanized anti-C1s antibody, of the present disclosure comprises: a) a VH variant 1 amino acid sequence depicted in FIG. 1 and as set forth in SEQ ID NO:10; and b) a VL variant 5 amino acid sequence depicted in FIG. 8 and as set forth in SEQ ID NO:24.

In some cases, an anti-C1s antibody, e.g., a humanized anti-C1s antibody, of the present disclosure comprises: a) a VH variant 2 amino acid sequence depicted in FIG. 2 and as set forth in SEQ ID NO:12; and b) a VL variant 1 amino acid sequence depicted in FIG. 6 and as set forth in SEQ ID NO:20.

In some cases, an anti-C1s antibody, e.g., a humanized anti-C1s antibody, of the present disclosure comprises: a) a VH variant 2 amino acid sequence depicted in FIG. 2 and as set forth in SEQ ID NO:12; and b) a VL variant 2 amino acid sequence depicted in FIG. 7 and as set forth in SEQ ID NO:22.

In some cases, an anti-C1s antibody, e.g., a humanized anti-C1s antibody, of the present disclosure comprises: a) a VH variant 2 amino acid sequence depicted in FIG. 2 and as set forth in SEQ ID NO:12; and b) a VL variant 5 amino acid sequence depicted in FIG. 8 and as set forth in SEQ ID NO:24.

In some cases, an anti-C1s antibody, e.g., a humanized anti-C1s antibody, of the present disclosure comprises: a) a VH variant 3 amino acid sequence depicted in FIG. 3 and as set forth in SEQ ID NO:14; and b) a VL variant 1 amino acid sequence depicted in FIG. 6 and as set forth in SEQ ID NO:20.

In some cases, an anti-C1s antibody, e.g., a humanized anti-C1s antibody, of the present disclosure comprises: a) a VH variant 3 amino acid sequence depicted in FIG. 3 and as set forth in SEQ ID NO:14; and b) a VL variant 2 amino acid sequence depicted in FIG. 7 and set forth in SEQ ID NO:22.

In some embodiments, the anti-C1s antibody comprises: a) a VH region comprising an amino acid sequence having at least about 80%, at least about 85%, at least about 90%, at least about 95%, at least about 96%, at least about 97%, at least about 98%, or at least about 99% percent identity with SEQ ID NO: 14; and b) a VL region comprising an amino acid sequence having at least about 80%, at least about 85%, at least about 90%, at least about 95%, at least about 96%, at least about 97%, at least about 98%, or at least about 99% percent identity with SEQ ID NO: 22. In some embodiments, the anti-C1s antibody comprises: a) a VH region comprising the amino acid sequence of SEQ ID NO: 14; and b) a VL region comprising the amino acid sequence of SEQ ID NO: 22.

In some cases, an anti-C1s antibody, e.g., a humanized anti-C1s antibody, of the present disclosure comprises: a) a VH variant 3 amino acid sequence depicted in FIG. 3 and as set forth in SEQ ID NO:14; and b) a VL variant 5 amino acid sequence depicted in FIG. 8 and as set forth in SEQ ID NO: 24.

In some cases, an anti-C1s antibody, e.g., a humanized anti-C1s antibody, of the present disclosure comprises: a) a VH variant 4 amino acid sequence depicted in FIG. 4 and as set forth in SEQ ID NO:16; and b) a VL variant 1 amino acid sequence depicted in FIG. 6 and as set forth in SEQ ID NO:20.

In some cases, an anti-C1s antibody, e.g., a humanized anti-C1s antibody, of the present disclosure comprises: a) a VH variant 4 amino acid sequence depicted in FIG. 4 and as set forth in SEQ ID NO:16; and b) a VL variant 2 amino acid sequence depicted in FIG. 7 and as set forth in SEQ ID NO:22.

In some cases, an anti-C1s antibody, e.g., a humanized anti-C1s antibody, of the present disclosure comprises: a) a VH variant 4 amino acid sequence depicted in FIG. 4 and as set forth in SEQ ID NO:16; and b) a VL variant 5 amino acid sequence depicted in FIG. 8 and as set forth in SEQ ID NO: 24.

In some cases, an anti-C1s antibody, e.g., a humanized anti-C1s antibody, of the present disclosure comprises: a) a VH variant 5 amino acid sequence depicted in FIG. 5 and as set forth in SEQ ID NO:18; and b) a VL variant 1 amino acid sequence depicted in FIG. 6 and as set forth in SEQ ID NO:20.

In some cases, an anti-C1s antibody, e.g., a humanized anti-C1s antibody, of the present disclosure comprises: a) a VH variant 5 amino acid sequence depicted in FIG. 5 and as set forth in SEQ ID NO:18; and b) a VL variant 2 amino acid sequence depicted in FIG. 7 and as set forth in SEQ ID NO:22.

In some cases, an anti-C1s antibody, e.g., a humanized anti-C1s antibody, of the present disclosure comprises: a) a VH variant 5 amino acid sequence depicted in FIG. 5 and as set forth in SEQ ID NO:18; and b) a VL variant 5 amino acid sequence depicted in FIG. 8 and as set forth in SEQ ID NO:24.

In particular embodiments, the antibody comprises a VH region comprising SEQ ID NO:14, a VL region comprising SEQ ID NO:22, and a heavy chain constant region; wherein the heavy chain constant region comprises an IgG4 constant region, wherein amino acid residue 308 of the heavy chain constant region corresponding to SEQ ID NO: 28 is a leucine, and amino acid residue 314 of the heavy chain constant region corresponding to SEQ ID NO: 28 is a serine; and wherein the antibody specifically binds activated C1s. In another embodiment, the antibody comprises a VH region comprising SEQ ID NO:14, a VL region comprising SEQ ID NO:22, and a heavy chain constant region comprising SEQ ID NO:28; wherein the antibody specifically binds activated C1s.

In some embodiments, the anti-C1s antibody comprises a heavy chain comprising an amino acid sequence having at least about 80%, at least about 85%, at least about 90%, at least about 95%, at least about 96%, at least about 97%, at least about 98%, or at least about 99% identity to SEQ ID NO: 29. As one non-limiting example, in some cases, an antibody, e.g., a humanized anti-C1s antibody, of the present disclosure comprises a heavy chain comprising the amino acid sequence set forth in SEQ ID NO:29.

In some embodiments, the anti-C1s antibody comprises a light chain comprising an amino acid sequence having at least about 80%, at least about 85%, at least about 90%, at least about 95%, at least about 96%, at least about 97%, at least about 98%, or at least about 99% identity to SEQ ID NO: 30. As one non-limiting example, in some cases, an antibody, e.g., a humanized anti-C1s antibody, of the present disclosure comprises a light chain comprising the amino acid sequence set forth in SEQ ID NO:30.

In some embodiments, the antibody comprises a heavy chain comprising SEQ ID NO:29 and a light chain comprising SEQ ID NO:30.

In some embodiments, the anti-C1s antibody comprises: a) a heavy chain comprising an amino acid sequence having at least about 80%, at least about 85%, at least about 90%, at least about 95%, at least about 96%, at least about 97%, at least about 98%, or at least about 99% identity to SEQ ID NO:29; and b) a light chain comprising an amino acid sequence having at least about 80%, at least about 85%, at least about 90%, at least about 95%, at least about 96%, at least about 97%, at least about 98%, or at least about 99% identity to SEQ ID NO:30. In some cases, an antibody, e.g., a humanized anti-C1s antibody, of the present disclosure comprises: a) a heavy chain comprising the amino acid sequence set forth in SEQ ID NO:29; and b) a light chain comprising the amino acid sequence set forth in SEQ ID NO:30. In some embodiments, to produce such an antibody, a nucleic acid(s) comprising a nucleotide sequence(s) encoding the amino acid sequences set forth in SEQ ID NO:31 and SEQ ID NO:32 can be used.

In certain embodiments the anti-C1s antibody comprises a light chain constant region. In some embodiments, the light chain constant region comprises SEQ ID NO: 45 (RTVAAPSVFIFPPSDEQLKSGTASVVCLLNNFYPRE-AKVQWKVDNALQSGNSQESVTEQ DSKDSTYSLSS-TLTLSKADYEKHKVYACEVTHQGLSSPVTKSFN-RGEC).

Binding Affinity

In some cases, an antibody, e.g., a humanized anti-C1s antibody, of the present disclosure binds a complement C1s protein from an individual that has a complement system. In some embodiments, an antibody, e.g., a humanized anti-C1s antibody, of the present disclosure binds a complement C1s protein from a mammal, fish, or invertebrate that has a complement system. In some embodiments, an antibody, e.g., a humanized anti-C1s antibody, of the present disclosure binds a mammalian complement C1s protein. In some embodiments, an antibody, e.g., a humanized anti-C1s antibody, of the present disclosure binds a human complement C1s protein. In some embodiments, an antibody, e.g., a humanized anti-C1s antibody, of the present disclosure binds a rat complement C1s protein. In some embodiments, an antibody, e.g., a humanized anti-C1s antibody, of the present disclosure binds a complement C1s protein having the amino acid sequence depicted in FIG. 13 (SEQ ID NO:9). Amino acid sequence SEQ ID NO:9 represents *Homo sapiens* complement C1s protein, which has the amino acid sequence set forth in FIG. 13.

In some cases, an antibody, e.g., a humanized anti-C1s antibody, of the present disclosure binds a complement C1s protein with a dissociation constant ($K_D$) of no more than 2.5 nM. In some embodiments, an antibody, e.g., a humanized anti-C1s antibody, of the present disclosure binds a complement C1s protein with a $K_D$ of no more than 2 nM. In some embodiments, an antibody, e.g., a humanized anti-C1s antibody, of the present disclosure binds a complement C1s protein with a $K_D$ of no more than 1.5 nM. In some embodiments, an antibody, e.g., a humanized anti-C1s antibody, of the present disclosure binds a complement C1s protein with a $K_D$ of no more than 1 nM. In some embodiments, an antibody, e.g., a humanized anti-C1s antibody, of the present disclosure binds a complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some cases, an antibody, e.g., a humanized anti-C1s antibody, of the present disclosure binds a complement C1s protein with a $K_D$ of no more than 0.3 nM. In some cases, an antibody, e.g., a humanized anti-C1s antibody, of the present disclosure binds a complement C1s protein with a $K_D$ of no more than 0.2 nM. In some cases, an antibody, e.g., a humanized anti-C1s antibody of the present disclosure, binds a complement C1s protein with a $K_D$ of no more than 0.1 nM. Methods to measure binding of an antibody to C1s protein can be determined by one skilled in the art.

In some cases, an antibody, e.g., a humanized anti-C1s antibody, of the present disclosure binds a complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some cases, an antibody, e.g., a humanized anti-C1s antibody, of the present disclosure binds a human complement C1s protein with a dissociation constant ($K_D$) of no more than 2.5 nM. In some cases, an antibody, e.g., a humanized anti-C1s antibody, of the present disclosure binds a human complement C1s protein with a dissociation constant ($K_D$) of no more than 1.5 nM. In some embodiments, an antibody, e.g., a humanized anti-C1s antibody, of the present disclosure binds a human complement C1s protein with a $K_D$ of no more than 2 nM. In some cases, an antibody, e.g., a humanized anti-C1s antibody, of the present disclosure binds a human complement C1s protein with a $K_D$ of no more than 1 nM. In some cases, an antibody, e.g., a humanized anti-C1s antibody, of the present disclosure binds a human complement C1s protein with a $K_D$ of no more than 0.9 nM, no more than 0.8 nM, no more than 0.7 nM, no more than 0.6 nM, no more than 0.5 nM, no more than 0.4 nM, no more than 0.3 nM, no more than 0.2 nM, no more than 0.1 nM. In some embodiments, an antibody, e.g., a humanized anti-C1s antibody, of the present disclosure binds a human complement C1s protein with a $K_D$ of no more than 0.3 nM. In some cases, an antibody, e.g., a humanized anti-C1s antibody, of the present disclosure binds a human complement C1s protein with a $K_D$ of no more than 0.2 nM. In some cases, an antibody, e.g., a humanized anti-C1s antibody, of the present disclosure binds a human complement C1s protein with a $K_D$ of no more than 0.1 nM. Methods to measure binding of an antibody to human C1s protein can be determined by one skilled in the art. In some cases, a binding assay as described in the Examples is used to determine the $K_D$ between an antibody and a human C1s protein.

In some cases, an antibody, e.g., a humanized anti-C1s antibody, of the present disclosure binds a human complement C1s protein with a $K_D$ of no more than 90 pM, no more than 80 pM, no more than 70 pM, no more than 60 pM, no more than 50 pM, no more than 40 pM, no more than 30 pM, no more than 20 pM, no more than 10 pM, no more than 9 pM, no more than 8 pM, no more than 7 pM, no more than 6 pM, no more than 5 pM, no more than 4 pM, no more than 3 pM, no more than 2 pM, no more than 1 pM.

In some cases, an antibody, e.g., a humanized anti-C1s antibody, of the present disclosure inhibits the classical complement pathway with a half-maximal inhibitory concentration ($IC_{50}$) of $10^{-8}$ M or less, $5 \times 10^{-9}$ M or less, or $10^{-9}$ M or less.

An antibody, e.g., a humanized anti-C1s antibody, of the present disclosure, when administered to an individual in need thereof, can reduce complement pathway (CP) activity from 10% to 100% (e.g., from 10% to 15%, from 15% to 20%, from 20% to 25%, from 25% to 30%, from 30% to 40%, from 40% to 50%, from 50% to 60%, from 60% to 70%, from 70% to 80%, from 80% to 90%, or from 90% to 100%) for a period of time of from 1 day to 1 week, from 1 week to 2 weeks, from 2 weeks to 4 weeks, from 4 weeks to 2 months, or more than 2 months.

For example, in some cases, a single dose of an antibody, e.g., a humanized anti-C1s antibody, of the present disclosure, when administered to an individual in need thereof, can reduce CP activity from 10% to 100% (e.g., from 10% to 15%, from 15% to 20%, from 20% to 25%, from 25% to 30%, from 30% to 40%, from 40% to 50%, from 50% to 60%, from 60% to 70%, from 70% to 80%, from 80% to 90%, or from 90% to 100%) for a period of time of from 1 day to 1 week, from 1 week to 2 weeks, from 2 weeks to 4 weeks, from 4 weeks to 2 months, or more than 2 months.

An antibody, e.g., a humanized anti-C1s antibody, of the present disclosure, when administered to an individual in need thereof, can provide for a serum concentration of the humanized anti-C1s antibody that is effective to reduce CP activity from 10% to 100% (e.g., from 10% to 15%, from 15% to 20%, from 20% to 25%, from 25% to 30%, from 30% to 40%, from 40% to 50%, from 50% to 60%, from 60% to 70%, from 70% to 80%, from 80% to 90%, or from 90% to 100%) for a period of time of from 1 day to 1 week, from 1 week to 2 weeks, from 2 weeks to 4 weeks, from 4 weeks to 2 months, or more than 2 months.

Nucleic Acids, Expression Vectors, and Host Cells

The present disclosure provides a nucleic acid comprising a nucleotide sequence encoding an anti-C1s antibody, e.g., a humanized anti-C1s antibody, of the present disclosure. In some cases, a nucleic acid of the present disclosure comprises a nucleotide sequence encoding the VH region of an anti-C1s antibody, e.g., a humanized anti-C1s antibody, of the present disclosure. In some cases, a nucleic acid of the present disclosure comprises a nucleotide sequence encoding the VL region of an anti-C1s antibody, e.g., a humanized anti-C1s antibody, of the present disclosure. In some cases, a nucleic acid of the present disclosure comprises a nucleotide sequence encoding the VH region and the VL region of an anti-C1s antibody, e.g., a humanized anti-C1s antibody, of the present disclosure.

A nucleotide sequence encoding an anti-C1s antibody, e.g., a humanized anti-C1s antibody, of the present disclosure can be operably linked to one or more regulatory elements, such as a promoter and enhancer, that allow expression of the nucleotide sequence in the intended target cells (e.g., a cell that is genetically modified to synthesize the encoded antibody). Thus, in some cases, the present disclosure provides a nucleic acid comprising a nucleotide sequence encoding an anti-C1s antibody, e.g., a humanized anti-C1s antibody, of the present disclosure, where the nucleotide sequence is operably linked to one or more regulatory elements, e.g., a promoter and/or an enhancer.

Suitable promoter and enhancer elements are known in the art. Suitable promoters for use in prokaryotic host cells include, but are not limited to, a bacteriophage T7 RNA polymerase promoter; a T3 promoter; a T5 promoter; a lambda P promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; a gpt promoter; an araBAD promoter; in vivo regulated promoters, such as an ssaG promoter or a related promoter (see, e.g., U.S. Patent Publication No. 20040131637), a pagC promoter (Pulkkinen and Miller, *J. Bacteriol.*, 1991: 173(1): 86-93; Alpuche-Aranda et al., PNAS, 1992; 89(21): 10079-83), a nirB promoter (Harborne et al. (1992) *Mol. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mol. Microbiol.* 22:367); a tet promoter (see, e.g., Hillen, W. and Wissmann, A. (1989) In Saenger, W. and Heinemann, U. (eds), *Topics* in *Molecular and Structural Biology, Protein—Nucleic Acid Interaction.* Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and $P_{Lambda}$. Non-limiting examples of operators for use in bacterial host cells include a lactose promoter operator (LacI repressor protein changes conformation when contacted with lactose, thereby preventing the LacI repressor protein from binding the operator), a tryptophan promoter operator (when complexed with tryptophan, TrpR repressor protein has a conformation that binds the operator; in the absence of tryptophan, the TrpR repressor protein has a conformation that does not bind the operator), and a tac promoter operator (see, for example, deBoer et al. (1983) Proc. Natl. Acad. Sci. U.S.A. 80:21-25).

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*).

For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters. Constitutive mammalian promoters include, but are not limited to, the promoters for the following genes: hypoxanthine phosphoribosyl transferase (HPRT), adenosine deaminase, pyruvate kinase, beta-actin promoter, and other constitutive promoters. Additional exemplary viral promoters which function constitutively in eukaryotic cells include, for example, promoters from the cytomegalovirus (CMV), simian virus (e.g., SV40), papilloma virus, adenovirus, human immunodeficiency virus (HIV), Rous sarcoma virus, cytomegalovirus, the long terminal repeats (LTR) of Moloney leukemia virus, and other retroviruses, and the thymidine kinase promoter of herpes simplex virus. Other constitutive promoters are known to those of ordinary skill in the art. The promoters useful as gene expression sequences of the disclosure also include inducible promoters. Inducible promoters are expressed in the presence of an inducing agent. For example, the metallothionein promoter is induced to promote transcription and translation in the presence of certain metal ions. Other inducible promoters are known to those of ordinary skill in the art.

Selection of the appropriate vector and promoter is well within the level of ordinary skill in the art.

A nucleic acid comprising a nucleotide sequence encoding an anti-C1s antibody, e.g., a humanized anti-C1s antibody, of the present disclosure can be present in any expression vector and/or a cloning vector known in the art. As used herein, an expression vector refers to any nucleic acid construct which contains the necessary elements for the transcription and translation of an inserted coding sequence, or in the case of an RNA viral vector, the necessary elements for replication and translation, when introduced into an appropriate host cell. Expression vectors can include plasmids, phagemids, viruses, and derivatives thereof.

Certain aspects of the present disclosure provide a recombinant vector comprising a nucleic acid comprising a nucleotide sequence encoding an anti-C1s antibody, e.g., a humanized anti-C1s antibody, of the present disclosure, where the recombinant vector is a cloning vector. Certain aspects of the present disclosure provide a recombinant vector comprising a nucleic acid comprising a nucleotide sequence encoding an anti-C1s antibody, e.g., a humanized anti-C1s antibody, of the present disclosure, where the recombinant vector is an expression vector, e.g., where the nucleotide sequence is operably linked to appropriate regulatory sequence(s) in the expression vector to ensure expression of the encoded antibody. Where a subject antibody comprises two separate polypeptides, nucleic acids encoding the two polypeptides can be cloned in the same or separate vectors to form one or more recombinant vectors. A recombinant vector can include a selectable marker, an origin of replication, and other features that provide for replication and/or maintenance of the recombinant vector (e.g., recombinant expression vector).

Large numbers of suitable vectors and promoters are known to those of skill in the art; many are commercially available for generating a subject recombinant vector. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host can be present. Suitable expression vectors include, but are not limited to, viral vectors. Examples of viral vectors include, but are not limited to, viral vectors based on: vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90:10613-10617); SV40; herpes simplex virus; a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus (see, e.g., Miyoshi et al., PNAS 94:10319 23, 1997; Takahashi et al., J Virol 73:7812 7816, 1999), myeloproliferative sarcoma virus, and mammary tumor virus); and the like.

In some embodiments, the vector is a viral vector. Viral vectors include, but are not limited to, nucleic acid sequences from the following viruses: retrovirus, such as Moloney murine leukemia virus, Harvey murine sarcoma virus, murine mammary tumor virus, and Rous sarcoma virus; adenovirus, adeno-associated virus; SV40-type viruses; polyomaviruses; Epstein-Barr viruses; papilloma viruses; herpes virus; vaccinia virus; polio virus; and RNA virus such as a retrovirus. One can readily employ other vectors well-known in the art. Certain viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Retroviruses have been approved for human gene therapy trials. Most useful are those retroviruses that are replication-deficient (i.e., capable of directing synthesis of the desired proteins, but incapable of manufacturing an infectious particle). Such genetically altered retroviral expression vectors have general utility for the high efficiency transduction of genes in vivo. Standard protocols for producing replication-deficient retroviruses (including the steps of incorporation of exogenous genetic material into a plasmid, transfection of a packaging cell line with plasmid, production of recombinant retroviruses by the packaging cell line, collection of viral particles from tissue culture media, and infection of the target cells with viral particles) are provided in Kriegler, M., Gene Transfer and Expression, A Laboratory Manual, W.H. Freeman Co., New York (1990) and Murry, E. J., Methods in Molecular Biology, Vol. 7, Humana Press, Inc., Cliffton, N.J. (1991).

In one embodiment, the virus is an adeno-associated virus, a double-stranded DNA virus. The adeno-associated virus can be engineered to be replication-deficient and is capable of infecting a wide range of cell types and species. It further has advantages such as heat and lipid solvent stability; high transduction frequencies in cells of diverse lineages, including hematopoietic cells; and lack of superinfection inhibition thus allowing multiple series of transductions. Reportedly, the adeno-associated virus can integrate into human cellular DNA in a site-specific manner, thereby minimizing the possibility of insertional mutagenesis and variability of inserted gene expression characteristic of retroviral infection. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In another embodiment, the viral vector is an adeno-associated virus (AAV) that has been manipulated to carry a polynucleotide encoding an anti-C1s antibody as disclosed herein. General methods for obtaining recombinant AAVs (rAAVs) have been disclosed. See, for example, U.S. Pat. No. 8,734,809, 2013/0195801 as well as the references cited therein. In some embodiments, a rAAV vector comprises one or more AAV inverted terminal repeats (ITRs) and a transgene of interest (e.g., an optimized FIX polynucleotide sequence). In certain embodiments, the methods of making rAAV involve culturing a desired host cell which contains a nucleic acid sequence encoding an AAV capsid protein or fragment thereof; a functional rep gene; a rAAV vector composed of, AAV inverted terminal repeats (ITRs) and a transgene of interest; and sufficient helper functions to permit packaging of the recombinant AAV vector into the AAV capsid proteins. Materials and methods for performing these and related procedures have been disclosed, for example, in U.S. Pat. No. 8,734,809, 2013/0195801, PCT/US1997/015692, PCT/US2002/033692, PCT/US2002/033630, WO2007/148971, WO00/20561, WO03/042361, and WO2007/04670.

One or more of different AAV vector sequences derived from nearly any serotype can be used in accord with the present disclosure. Choice of a particular AAV vector sequence will be guided by known parameters such as tropism of interest, required vector yields, etc. Generally, the AAV serotypes have genomic sequences of significant homology at the amino acid and the nucleic acid levels, provide a related set of genetic functions, produce virions which are related, and replicate and assemble similarly. For the genomic sequence of the various AAV serotypes and an overview of the genomic similarities see e.g. GenBank Accession number U89790; GenBank Accession number J01901; GenBank Accession number AF043303; GenBank Accession number AF085716; Chlorini et al. (1997, J. Vir. 71: 6823-33); Srivastava et al. (1983, J. Vir. 45:555-64); Chlorini et al. (1999, J. Vir. 73:1309-1319); Rutledge et al. (1998, J. Vir. 72:309-319); and Wu et al. (2000, J. Vir. 74: 8635-47). AAV serotypes 1, 2, 3, 4 and 5 are an illustrative source of AAV nucleotide sequences for use in the context of the present disclosure. AAV6, AAV7, AAV8 or AAV9 or newly developed AAV-like particles obtained by e.g. capsid shuffling techniques and AAV capsid libraries, or from newly designed, developed or evolved ITR's are also suitable for certain disclosure applications. See Dalkara, D et al. (2013), Sci Transl. Med. 5(189): 189ra76; Kotterman, MA Nat. Rev. Genet. (2014) 15(7):455.

In other embodiments, the vector is derived from lentivirus. In certain embodiments, the vector is a vector of a recombinant lentivirus capable of infecting non-dividing cells.

The lentiviral genome and the proviral DNA typically have the three genes found in retroviruses: gag, pol and env, which are flanked by two long terminal repeat (LTR) sequences. The gag gene encodes the internal structural (matrix, capsid and nucleocapsid) proteins; the pol gene encodes the RNA-directed DNA polymerase (reverse transcriptase), a protease and an integrase; and the env gene encodes viral envelope glycoproteins. The 5' and 3' LTR's serve to promote transcription and polyadenylation of the virion RNA's. The LTR contains all other cis-acting sequences necessary for viral replication. Lentiviruses have additional genes including vif, vpr, tat, rev, vpu, nef and vpx (in HIV-1, HIV-2 and/or SIV).

Adjacent to the 5' LTR are sequences necessary for reverse transcription of the genome (the tRNA primer binding site) and for efficient encapsidation of viral RNA into particles (the Psi site). If the sequences necessary for encapsidation (or packaging of retroviral RNA into infectious virions) are missing from the viral genome, the cis defect prevents encapsidation of genomic RNA.

However, the resulting mutant remains capable of directing the synthesis of all virion proteins. The disclosure provides a method of producing a recombinant lentivirus capable of infecting a non-dividing cell comprising transfecting a suitable host cell with two or more vectors carrying the packaging functions, namely gag, pol and env, as well as rev and tat. As will be disclosed herein below, vectors lacking a functional tat gene are desirable for certain applications. Thus, for example, a first vector can provide a nucleic acid encoding a viral gag and a viral pol and another vector can provide a nucleic acid encoding a viral env to produce a packaging cell. Introducing a vector providing a heterologous gene, herein identified as a transfer vector, into that packaging cell yields a producer cell which releases infectious viral particles carrying the foreign gene of interest.

According to the above-indicated configuration of vectors and foreign genes, the second vector can provide a nucleic acid encoding a viral envelope (env) gene. The env gene can be derived from nearly any suitable virus, including retroviruses. In some embodiments, the env protein is an amphotropic envelope protein which allows transduction of cells of human and other species.

Examples of retroviral-derived env genes include, but are not limited to: Moloney murine leukemia virus (MoMuLV or MMLV), Harvey murine sarcoma virus (HaMuSV or HSV), murine mammary tumor virus (MuMTV or MMTV), gibbon ape leukemia virus (GaLV or GALV), human immunodeficiency virus (HIV) and Rous sarcoma virus (RSV). Other env genes such as Vesicular stomatitis virus (VSV) protein G (VSV G), that of hepatitis viruses and of influenza also can be used.

The vector providing the viral env nucleic acid sequence is associated operably with regulatory sequences described elsewhere herein.

In certain embodiments, the vector includes a lentiviral vector in which the HIV virulence genes env, vif, vpr, vpu and nef were deleted without compromising the ability of the vector to transduce non-dividing cells.

In some embodiments, the vector includes a lentiviral vector which comprises a deletion of the U3 region of the 3' LTR. The deletion of the U3 region can be the complete deletion or a partial deletion.

In some embodiments, the lentiviral vector of the disclosure comprising a nucleotide sequence encoding an anti-C1s antibody described herein can be transfected in a cell with (a) a first nucleotide sequence comprising a gag, a pol, or gag and pol genes and (b) a second nucleotide sequence comprising a heterologous env gene; wherein the lentiviral vector lacks a functional tat gene. In other embodiments, the cell is further transfected with a fourth nucleotide sequence comprising a rev gene. In certain embodiments, the lentiviral vector lacks functional genes selected from vif, vpr, vpu, vpx and nef, or a combination thereof.

In certain embodiments, a lentiviral vector comprises one or more nucleotide sequences encoding a gag protein, a Rev-response element, a central polypurine track (cPPT), or any combination thereof.

Examples of the lentiviral vectors are disclosed in WO9931251, WO9712622, WO9817815, WO9817816, and WO9818934, which are incorporated herein by reference in their entireties.

Other vectors include plasmid vectors. Plasmid vectors have been extensively described in the art and are well-known to those of skill in the art. See, e.g., Sambrook et al., Molecular Cloning: A Laboratory Manual, Second Edition, Cold Spring Harbor Laboratory Press, 1989. In the last few years, plasmid vectors have been found to be particularly advantageous for delivering genes to cells in vivo because of their inability to replicate within and integrate into a host genome. These plasmids, however, having a promoter compatible with the host cell, can express a peptide from a gene operably encoded within the plasmid. Some commonly used plasmids available from commercial suppliers include pBR322, pUC18, pUC19, various pcDNA plasmids, pRC/CMV, various pCMV plasmids, pSV40, and pBlueScript. Additional examples of specific plasmids include pcDNA3.1, catalog number V79020; pcDNA3.1/hygro, catalog number V87020; pcDNA4/myc-His, catalog number V86320; and pBudCE4.1, catalog number V53220, all from Invitrogen (Carlsbad, CA.). Other plasmids are well-known to those of ordinary skill in the art. Additionally, plasmids can be custom designed using standard molecular biology techniques to remove and/or add specific fragments of DNA.

Host Cells

The present disclosure provides isolated genetically modified host cells (e.g., in vitro cells) that are genetically modified with a subject nucleic acid. In some embodiments, a subject isolated genetically modified host cell can produce a subject antibody. Such a cell is referred to as a "recombinant cell" or a "genetically modified host cell." A genetically modified host cell of the present disclosure comprises a nucleic acid comprising a nucleotide sequence encoding an anti-C1s antibody, e.g., a humanized anti-C1s antibody, of the present disclosure.

Suitable host cells include eukaryotic host cells, such as a mammalian cell, an insect host cell, a yeast cell; and prokaryotic cells, such as a bacterial cell. Introduction of a subject nucleic acid into the host cell can be effected, for example by calcium phosphate precipitation, DEAE dextran mediated transfection, liposome-mediated transfection, electroporation, or other known method.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), CVI (monkey kidney line), RAT1 cells, mouse L cells (ATCC No. CCLI.3), human embryonic kidney (HEK) cells (ATCC No. CRL1573), HLHepG2 cells, and the like. In some cases, the cells are HEK cells. In certain embodiments, the cells are HEK 293 cells. In some cases, the cells are CHO cells, e.g., CHO-K1 cells (ATCC No. CCL-61), CHO-M cells, CHO-DG44 cells (ATCC No. PTA-3356), DUXB11 (Chinese Hamster Ovary line, DHFR minus), R1610 (Chinese hamster fibroblast), BALBC/3T3 (mouse fibroblast), HAK (hamster kidney line), SP2/O (mouse myeloma), P3x63-Ag3.653 (mouse myeloma), BFA-1c1BPT (bovine endothelial cells), RAJI (human lymphocyte), PER.C6®, NS0, CAP, BHK21, and the like. In some embodiments, the host cell is a COS cell. In some embodiments, the host cell is a 293 cell. In some embodiments, the host cell is a CHO cell.

Suitable yeast cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii*, and the like. In some embodiments, the host cell is a *Saccharomyces*. In some embodiments, the host cell is a *Pichia*.

Suitable prokaryotic cells include, but are not limited to, any of a variety of laboratory strains of *Escherichia coli, Bacillus* (e.g., *B. subtilis*), *Lactobacillus* sp., and the like. See, e.g., Carrier et al. (1992) *J. Immunol.* 148:1176-1181; U.S. Pat. No. 6,447,784; and Sizemore et al. (1995) Science 270:299-302. Typically, the laboratory strain is one that is non-pathogenic. In some embodiments, the host cell is *Escherichia coli*. In some embodiments, the host cell is *Bacillus subtilis*.

Introduction of the isolated nucleic acid molecules of the disclosure into the host cell can be accomplished by various techniques well known to those of skill in the art. These include, but are not limited to, transfection (including electrophoresis and electroporation), protoplast fusion, calcium phosphate precipitation, cell fusion with enveloped DNA, microinjection, and infection with intact virus. See, Ridgway, A. A. G. "*Mammalian Expression Vectors*" Chapter 24.2, pp. 470-472 Vectors, Rodriguez and Denhardt, Eds. (Butterworths, Boston, Mass. 1988). Most preferably, plasmid introduction into the host is via electroporation. The transformed cells are grown under conditions appropriate to the production of the light chains and heavy chains, and assayed for heavy and/or light chain protein synthesis. Exemplary assay techniques include enzyme-linked immunosorbent assay (ELISA), radioimmunoassay (RIA), or flourescence-activated cell sorter analysis (FACS), immunohistochemistry and the like.

Host cells comprising the isolated nucleic acid molecules of the disclosure are grown in an appropriate growth medium. As used herein, the term "appropriate growth medium" means a medium containing nutrients required for the growth of cells. Nutrients required for cell growth can include a carbon source, a nitrogen source, essential amino acids, vitamins, minerals, and growth factors. Optionally, the media can contain one or more selection factors. Optionally the media can contain bovine calf serum or fetal calf serum (FCS). In one embodiment, the media contains substantially no IgG. The growth medium will generally select for cells containing the DNA construct by, for example, drug selection or deficiency in an essential nutrient which is complemented by the selectable marker on the DNA construct or co-transfected with the DNA construct. Cultured mammalian cells are generally grown in commercially available serum-containing or serum-free media (e.g., MEM, DMEM, DMEM/F12). In one embodiment, the medium is CDoptiCHO (Invitrogen, Carlsbad, CA.). In another embodiment, the medium is CD17 (Invitrogen, Carlsbad, CA.). Selection of a medium appropriate for the particular cell line used is within the level of those ordinary skilled in the art.

Pharmaceutical Compositions

The present disclosure provides compositions, including pharmaceutical compositions comprising an anti-C1s antibody, e.g., a humanized anti-C1s antibody, of the present disclosure. In general, a pharmaceutical composition, also referred to herein as a formulation, comprises an effective amount of an anti-C1s antibody, e.g., a humanized anti-C1s antibody, of the present disclosure. An "effective amount" means a dosage sufficient to produce a desired result, e.g., reduction in an adverse symptom associated with a complement-mediated disease or disorder, amelioration of a symptom of a complement-mediated disease or disorder, slowing progression of a complement-mediated disease or disorder, etc. Generally, the desired result is at least a reduction in a symptom of a complement-mediated disease or disorder, as compared to a control. In some embodiments, an anti-C1s antibody, e.g., a humanized anti-C1s antibody, of the present disclosure is formulated and/or modified to enable the antibody to cross the blood-brain barrier. In some embodiments, an anti-C1s antibody, e.g., a humanized anti-C1s antibody, of the present disclosure is delivered in such a manner as to avoid the blood-brain barrier. In some embodiments, an anti-C1s antibody, e.g., a humanized anti-C1s antibody, of the present disclosure is formulated with an agent that facilitates crossing the blood-brain barrier. In some embodiments, an anti-C1s antibody, e.g., a humanized anti-C1s antibody, of the present disclosure is fused, directly or through a linker, to a compound that promotes the crossing of the blood-brain barrier.

Formulations

The pharmaceutical composition can be formulated for parenteral administration (i.e. intravenous, subcutaneous, or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

In the subject methods, an anti-C1s antibody, e.g., a humanized anti-C1s antibody, of the present disclosure can be administered to the host using any convenient means capable of resulting in the desired therapeutic effect or diagnostic effect. Thus, the agent can be incorporated into a variety of formulations for therapeutic administration. More particularly, an anti-C1s antibody, e.g., a humanized anti-C1s antibody, of the present disclosure can be formulated into pharmaceutical compositions by combination with appropriate, pharmaceutically acceptable carriers, pharmaceutically acceptable diluents, or other pharmaceutically acceptable excipients and can be formulated into preparations in solid, semi-solid, liquid or gaseous forms, such as tablets, capsules, powders, granules, ointments, solutions, suppositories, injections, inhalants and aerosols. In some embodiments, a pharmaceutical composition comprises an anti-C1s antibody, e.g., a humanized anti-C1s antibody, of the present disclosure and a pharmaceutically acceptable excipient.

In pharmaceutical dosage forms, an anti-C1s antibody, e.g., a humanized anti-C1s antibody, of the present disclosure can be administered in the form of their pharmaceutically acceptable salts, or they can also be used alone or in appropriate association, as well as in combination, with other pharmaceutically active compounds. The following methods and excipients are merely exemplary and are in no way limiting.

For oral preparations, an anti-C1s antibody, e.g., a humanized anti-C1s antibody, of the present disclosure can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

An anti-C1s antibody, e.g., a humanized anti-C1s antibody, of the present disclosure can be formulated into preparations for injection by dissolving, suspending or emulsifying the antibody in an aqueous or nonaqueous solvent, such as vegetable or other similar oils, propylene glycol, synthetic aliphatic acid glycerides, injectable organic esters (e.g., ethyl oleate), esters of higher aliphatic acids or propylene glycol; and if desired, with conventional additives such as solubilizers, isotonic agents, suspending agents, emulsifying agents, stabilizers and preservatives. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Furthermore, the pharmaceutical composition of the present disclosure can comprise further agents such as dopamine or psychopharmacologic drugs, depending on the intended use of the pharmaceutical composition.

Pharmaceutical compositions comprising an anti-C1s antibody, e.g., a humanized anti-C1s antibody, of the present disclosure are prepared by mixing an anti-C1s antibody, e.g., a humanized anti-C1s antibody, of the present disclosure having the desired degree of purity with optional physiologically acceptable carriers, other excipients, stabilizers, surfactants, buffers and/or tonicity agents. Acceptable carriers, other excipients and/or stabilizers are nontoxic to recipients at the dosages and concentrations employed, and include buffers such as phosphate, citrate, and other organic acids; antioxidants including ascorbic acid, glutathione, cysteine, methionine and citric acid; preservatives (such as ethanol, benzyl alcohol, phenol, m-cresol, p-chlor-m-cresol, methyl or propyl parabens, benzalkonium chloride, or combinations thereof); amino acids such as arginine, glycine, ornithine, lysine, histidine, glutamic acid, aspartic acid, isoleucine, leucine, alanine, phenylalanine, tyrosine, tryptophan, methionine, serine, proline and combinations thereof; monosaccharides, disaccharides and other carbohydrates; low molecular weight (less than about 10 residues) polypeptides; proteins, such as gelatin or serum albumin; chelating agents such as EDTA; sugars such as trehalose, sucrose, lactose, glucose, mannose, maltose, galactose, fructose, sorbose, raffinose, glucosamine, N-methylglucosamine, galactosamine, and neuraminic acid; and/or non-ionic surfactants such as Tween, Brij Pluronics, Triton-X, or polyethylene glycol (PEG).

The pharmaceutical composition can be in a liquid form, a lyophilized form, or a liquid form reconstituted from a lyophilized form, wherein the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents can be used for the production of pharmaceutical compositions for parenteral administration; see also Chen (1992) Drug Dev Ind Pharm 18, 1311-54.

Exemplary antibody concentrations in a subject pharmaceutical composition can range from about 1 mg/mL to about 200 mg/mL or from about 50 mg/mL to about 200 mg/mL, or from about 150 mg/mL to about 200 mg/mL.

An aqueous formulation of an anti-C1s antibody, e.g., a humanized anti-C1s antibody, of the present disclosure can be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

A tonicity agent can be included in the antibody formulation to modulate the tonicity of the formulation. Exemplary tonicity agents include sodium chloride, potassium chloride, glycerin and any component from the group of amino acids, sugars as well as combinations thereof. In some embodiments, the aqueous formulation is isotonic, although hypertonic or hypotonic solutions can be suitable. The term "isotonic" denotes a solution having the same tonicity as some other solution with which it is compared, such as a physiological salt solution or serum. Tonicity agents can be used in an amount of about 5 mM to about 350 mM, e.g., in an amount of 100 mM to 350 nM.

A surfactant can also be added to the antibody formulation to reduce aggregation of the formulated antibody and/or minimize the formation of particulates in the formulation and/or reduce adsorption. Exemplary surfactants include polyoxyethylensorbitan fatty acid esters (Tween), polyoxyethylene alkyl ethers (Brij), alkylphenylpolyoxyethylene ethers (Triton-X), polyoxyethylene-polyoxypropylene copolymer (Poloxamer, Pluronic), and sodium dodecyl sulfate (SDS). Examples of suitable polyoxyethylenesorbitan-fatty acid esters are polysorbate 20, (sold under the trademark TWEEN 20™) and polysorbate 80 (sold under the trademark Tween 80™). Examples of suitable polyethylene-polypropylene copolymers are those sold under the names PLURONIC® F68 or POLOXAMER 188™. Examples of suitable Polyoxyethylene alkyl ethers are those sold under the trademark BRIJ™. Exemplary concentrations of surfactant can range from about 0.001% to about 1% w/v.

A lyoprotectant can also be added in order to protect the labile active ingredient (e.g. a protein) against destabilizing conditions during the lyophilization process. For example, known lyoprotectants include sugars (including glucose and sucrose); polyols (including mannitol, sorbitol and glycerol); and amino acids (including alanine, glycine and glutamic acid). Lyoprotectants can be included in an amount of about 10 mM to 500 nM.

In some cases, a subject formulation includes an anti-C1s antibody, e.g., a humanized anti-C1s antibody, of the present disclosure, and one or more of the above-identified agents (e.g., a surfactant, a buffer, a stabilizer, a tonicity agent) and is essentially free of one or more preservatives, such as ethanol, benzyl alcohol, phenol, m-cresol, p-chlor-m-cresol, methyl or propyl parabens, benzalkonium chloride, and combinations thereof. In other embodiments, a preservative is included in the formulation, e.g., at concentrations ranging from about 0.001 to about 2% (w/v).

For example, a subject formulation can be a liquid or lyophilized formulation suitable for parenteral administration, and can comprise: about 1 mg/mL to about 200 mg/mL of an anti-C1s antibody, e.g., a humanized anti-C1s antibody, of the present disclosure; about 0.001% to about 1% of at least one surfactant; about 1 mM to about 100 mM of a buffer; optionally about 10 mM to about 500 mM of a stabilizer; and about 5 mM to about 305 mM of a tonicity agent; and has a pH of about 4.0 to about 7.0.

As another example, a subject parenteral formulation is a liquid or lyophilized formulation comprising: about 1 mg/mL to about 200 mg/mL of an anti-C1s antibody, e.g., a humanized anti-C1s antibody, of the present disclosure; 0.04% Tween 20 w/v; 20 mM L-histidine; and 250 mM Sucrose; and has a pH of 5.5.

As another example, a subject parenteral formulation comprises a lyophilized formulation comprising: 1) 15 mg/mL of a subject antibody (e.g., a humanized anti-C1s antibody of the present disclosure); 0.04% Tween 20 w/v; 20 mM L-histidine; and 250 mM sucrose; and has a pH of 5.5; or 2) 75 mg/mL of a subject antibody; 0.04% Tween 20 w/v; 20 mM L-histidine; and 250 mM sucrose; and has a pH of 5.5; or 3) 75 mg/mL of a subject antibody; 0.02% Tween 20 w/v; 20 mM L-histidine; and 250 mM sucrose; and has a pH of 5.5; or 4) 75 mg/mL of a subject antibody; 0.04% Tween 20 w/v; 20 mM L-histidine; and 250 mM trehalose; and has a pH of 5.5; or 5) 75 mg/mL of a subject antibody; 0.02% Tween 20 w/v; 20 mM L-histidine; and 250 mM trehalose; and has a pH of 5.5.

As another example, a subject parenteral formulation is a liquid formulation comprising: 1) 7.5 mg/mL of a subject antibody; 0.02% Tween 20 w/v; 120 mM L-histidine; and 250 125 mM sucrose; and has a pH of 5.5; or 2) 37.5 mg/mL of a subject antibody; 0.02% Tween 20 w/v; 10 mM L-histidine; and 125 mM sucrose; and has a pH of 5.5; or 3) 37.5 mg/mL of a subject antibody; 0.01% Tween 20 w/v; 10 mM L-histidine; and 125 mM sucrose; and has a pH of 5.5; or 4) 37.5 mg/mL of a subject antibody; 0.02% Tween 20 w/v; 10 mM L-histidine; 125 mM trehalose; and has a pH of 5.5; or 5) 37.5 mg/mL of a subject antibody; 0.01% Tween 20 w/v; 10 mM L-histidine; and 125 mM trehalose; and has a pH of 5.5; or 6) 5 mg/mL of a subject antibody; 0.02% Tween 20 w/v; 20 mM L-histidine; and 250 mM trehalose; and has a pH of 5.5; or 7) 75 mg/mL of a subject antibody; 0.02% Tween 20 w/v; 20 mM L-histidine; and 250 mM mannitol; and has a pH of 5.5; or 8) 75 mg/mL of a subject antibody; 0.02% Tween 20 w/v; 20 mM L histidine; and 140 mM sodium chloride; and has a pH of 5.5; or 9) 150 mg/mL of a subject antibody; 0.02% Tween 20 w/v; 20 mM L-histidine; and 250 mM trehalose; and has a pH of 5.5; or 10) 150 mg/mL of a subject antibody; 0.02% Tween 20 w/v; 20 mM L-histidine; and 250 mM mannitol; and has a pH of 5.5; or 11) 150 mg/mL of a subject antibody; 0.02% Tween 20 w/v; 20 mM L-histidine; and 140 mM sodium chloride; and has a pH of 5.5; or 12) 10 mg/mL of a subject antibody; 0.01% Tween 20 w/v; 20 mM L-histidine; and 40 mM sodium chloride; and has a pH of 5.5.

A subject antibody can be utilized in aerosol formulation to be administered via inhalation. A subject antibody can be formulated into pressurized acceptable propellants such as dichlorodifluoromethane, propane, nitrogen and the like. Aerosol formulations such as nasal spray formulations include purified aqueous or other solutions of the active agent with preservative agents and isotonic agents. Such formulations are adjusted to a pH and isotonic state compatible with the nasal mucous membranes.

Unit dosage forms for oral administration such as syrups, elixirs, and suspensions can be provided wherein each dosage unit, for example, teaspoonful, tablespoonful, or tablet, contains a predetermined amount of the composition. Similarly, unit dosage forms for injection or intravenous administration can comprise a subject antibody in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of an anti-C1s antibody, e.g., a humanized anti-C1s antibody, of the present disclosure, calculated in an amount sufficient to produce the desired effect in association with a pharmaceutically acceptable diluent, carrier or vehicle. The specifications for a subject antibody can depend on the particular antibody employed and the effect to be achieved, and the pharmacodynamics associated with each antibody in the host.

Other modes of administration will also find use with a method of the present disclosure. For instance, a subject antibody can be formulated in suppositories and, in some cases, aerosol and intranasal compositions. For suppositories, the vehicle composition will include traditional binders and carriers such as, polyalkylene glycols, or triglycerides. Such suppositories can be formed from mixtures containing the active ingredient in the range of about 0.5% to about 10% (w/w), e.g., about 1% to about 2%.

Intranasal formulations will usually include vehicles that neither cause irritation to the nasal mucosa nor significantly disturb ciliary function. Diluents such as water, aqueous saline or other known substances can be employed. The nasal formulations can also contain preservatives such as, but not limited to, chlorobutanol and benzalkonium chloride. A surfactant can be present to enhance absorption of the subject antibody by the nasal mucosa.

A subject antibody can be administered as an injectable formulation. Typically, injectable compositions are prepared as liquid solutions or suspensions; solid forms suitable for solution in, or suspension in, liquid vehicles prior to injection can also be prepared. The preparation can also be emulsified or the antibody encapsulated in liposome vehicles.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pennsylvania, 17th edition, 1985. The composition or formulation to be administered will, in any event, contain a quantity of a subject antibody adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

In some embodiments, an anti-C1s antibody, e.g., a humanized anti-C1s antibody, of the present disclosure is formulated in a controlled release formulation. Sustained-release preparations can be prepared using methods well known in the art. Suitable examples of sustained-release preparations include semipermeable matrices of solid hydrophobic polymers containing the antibody in which the matrices are in the form of shaped articles, e.g. films or microcapsules. Examples of sustained-release matrices include polyesters, copolymers of L-glutamic acid and ethyl-L-glutamate, non-degradable ethylene-vinyl acetate, hydrogels, polylactides, degradable lactic acid-glycolic acid copolymers and poly-D-(−)-3-hydroxybutyric acid. Possible loss of biological activity and possible changes in immunogenicity of antibodies comprised in sustained-release preparations can be prevented by using appropriate additives, by controlling moisture content and by developing specific polymer matrix compositions.

Controlled release within the scope of the present disclosure can be taken to mean any one of a number of extended release dosage forms. The following terms can be considered to be substantially equivalent to controlled release, for the purposes of the present disclosure: continuous release, controlled release, delayed release, depot, extended release, gradual release, immediate release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, and sustained-action medications. Further discussions of these terms can be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release can be found in Agis F. Kydonieus, *Controlled Release Technologies: Methods, Theory and Applications,* 1980 (CRC Press, Inc.).

There are a number of controlled release drug formulations that are developed for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems can be found in Yie W. Chien, *Novel Drug Delivery Systems,* 1992 (Marcel Dekker, Inc.).

Dosages

A suitable dosage can be determined by an attending physician or other qualified medical personnel, based on various clinical factors. As is well known in the medical arts, dosages for any one patient depend upon many factors, including the patient's size, body surface area, age, the particular compound to be administered, sex of the patient, time, and route of administration, general health, and other drugs being administered concurrently. An anti-C1s antibody, e.g., a humanized anti-C1s antibody of the present disclosure can be administered in amounts between 1 ng/kg body weight and 20 mg/kg body weight per dose, e.g. between 0.1 mg/kg body weight to 10 mg/kg body weight, e.g., between 0.5 mg/kg body weight to 5 mg/kg body weight; however, doses below or above this exemplary range are envisioned, especially considering the aforementioned factors. If the regimen is a continuous infusion, it can also be in the range of 1 µg to 10 mg per kilogram of body weight per minute.

In some embodiments, a dose of an anti-C1s antibody, e.g., a humanized anti-C1s antibody, of the present disclosure is in the range of 0.001 µg to 1000 µg; however, doses below or above this exemplary range are envisioned, especially considering the aforementioned factors. In some embodiments, the dosage can range, e.g., from about 0.0001 to 100 mg/kg, or from about 0.01 to 5 mg/kg (e.g., 0.02 mg/kg, 0.25 mg/kg, 0.5 mg/kg, 0.75 mg/kg, 1 mg/kg, 2 mg/kg, etc.) body weight. For example dosages can be 1 mg/kg body weight or 10 mg/kg body weight or within the range of 1-10 mg/kg, or at least 1 mg/kg. Doses intermediate in the above ranges are also intended to be within the scope of the disclosure.

In some embodiments, an anti-C1s antibody, e.g., a humanized anti-C1s antibody, of the present disclosure is administered in an amount that provides for a peak serum concentration of from about 1 µg/ml to about 1 mg/ml, e.g., from about 1 µg/ml to about 2.5 µg/ml, from about 2.5 µg/ml to about 5 µg/ml, from about 5 µg/ml to about 7.5 µg/ml, from about 7.5 µg/ml to about 10 µg/ml, from about 10 µg/ml to about 25 µg/ml, from about 25 µg/ml to about 50 µg/ml, from about 50 µg/ml to about 100 µg/ml, from about 100 µg/ml to about 250 µg/ml, from about 250 µg/ml to about 500 µg/ml, from about 500 µg/ml to about 750 µg/ml, or from about 750 µg/ml to about 1000 µg/ml. In some embodiments, a subject anti-C1s antibody is administered in an amount that provides for a peak serum concentration of greater than 1 mg/ml, e.g., from about 1 mg/ml to about 2 mg/ml, from about 2 mg/ml to about 5 mg/ml, or from about 5 mg/ml to about 10 mg/ml. A humanized antibody of the present disclosure can be administered according to any schedule and for any period of time.

Those of skill will readily appreciate that dose levels and administration schedules can vary as a function of the specific antibody, the severity of the symptoms and the susceptibility of the subject to side effects. Preferred dosages and administration schedules for a given compound are readily determinable by those of skill in the art by a variety of means.

Routes of Administration

A subject antibody is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intrathecal, intracranial, subcutaneous, intradermal, topical, intravenous, intraperitoneal, intraarterial (e.g., via the carotid artery), spinal or brain delivery, rectal, nasal, oral, and other enteral and parenteral routes of administration. Routes of administration can be combined, if desired, or adjusted depending upon the antibody and/or the desired effect. A subject antibody composition can be administered in a single dose or in multiple doses. In some embodiments, a subject antibody composition is administered orally. In some embodiments, a subject antibody composition is administered via an inhalational route. In some embodiments, a subject antibody composition is administered intranasally. In some embodiments, a subject antibody composition is administered locally. In some embodiments, a subject antibody composition is administered intracranially. In some embodiments, a subject antibody composition is administered intravenously. In some embodiments, a subject antibody composition is administered subcutaneously. In some embodiments, a subject antibody composition is administered intramuscularly. In some embodiments, a subject antibody composition is administered intrathecally.

An antibody of the present disclosure can be administered to a host using any available conventional methods and routes suitable for delivery of conventional drugs, including systemic or localized routes. In general, routes of administration contemplated by the disclosure include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, intrathecal, and intravenous routes, i.e., any route of administration other than through the alimentary canal. Parenteral administration can be carried to effect systemic or local delivery of a subject antibody. Where systemic delivery is desired, administration typically involves invasive or systemically absorbed topical or mucosal administration of pharmaceutical preparations.

A subject antibody can also be delivered to the subject by enteral administration. Enteral routes of administration include, but are not necessarily limited to, oral and rectal (e.g., using a suppository) delivery.

By treatment is meant at least an amelioration of the symptoms associated with the pathological condition afflicting the host, where amelioration is used in a broad sense to refer to at least a reduction in the magnitude of a parameter, e.g., symptom, associated with the pathological condition being treated, such as a complement-mediated disease or disorder. As such, treatment also includes situations where the pathological condition, or at least symptoms associated therewith, are completely inhibited, e.g., prevented from happening, or stopped, e.g., terminated, such that the host no longer suffers from the pathological condition, or at least the symptoms that characterize the pathological condition.

In some embodiments, an anti-C1s antibody, e.g., a humanized anti-C1s antibody, of the present disclosure is administered by injection and/or delivery, e.g., to a site in a brain artery or directly into brain tissue. A subject antibody, e.g., a humanized antibody, can also be administered directly to a target site e.g., by biolistic delivery to the target site.

A variety of hosts (wherein the term "host" is used interchangeably herein with the terms "subject," "individual," and "patient") are treatable according to the subject methods. Generally such hosts are "mammals" or "mammalian," where these terms are used broadly to describe organisms which are within the class mammalia, including the orders carnivore (e.g., cats), herbivores (e.g., cattle, horses, and sheep), omnivores (e.g., dogs, goats, and pigs), rodentia (e.g., mice, guinea pigs, and rats), and primates (e.g., humans, chimpanzees, and monkeys). In some embodiments, the host is an individual that has a complement system, such as a mammal, fish, or invertebrate. In some embodiments, the host is a complement system-containing mammal, fish, or invertebrate companion animal, agricultural animal, work animal, zoo animal, or lab animal. In some embodiments, the host is human.

The embodiments include compositions comprising a container suitable for containing a composition comprising a subject anti-C1s antibody for administration to an individual. For example, a subject antibody can be disposed within a container suitable for containing a pharmaceutical composition. The container can be, for example, a bottle (e.g., with a closure device, such as a cap), a blister pack (e.g., which can provide for enclosure of one or more doses per blister), a vial, flexible packaging (e.g., sealed Mylar or plastic bags), an ampule (for single doses in solution), a dropper, a syringe, thin film, a tube and the like. In some embodiments, a container, such as a sterile container, comprises a subject pharmaceutical composition. In some embodiments the container is a bottle or a syringe. In some embodiments the container is a bottle. In some embodiments the container is a syringe.

Kits with unit doses of an anti-C1s antibody, e.g., a humanized anti-C1s antibody, of the present disclosure, e.g. in oral or injectable doses, are provided. In such kits, in addition to the containers containing the unit doses will be an informational package insert describing the use and attendant benefits of the antibody in treating pathological condition of interest. Preferred compounds and unit doses are those described herein above.

Methods of Treating a Complement-Mediated Disease or Disorder

The present disclosure provides methods of treating a subject in need thereof with an anti-C1s antibody or a nucleotide encoding an anti-C1s antibody of the present disclosure. In some embodiments, the methods comprise treating a complement-mediated disease or disorder. The methods generally involve administering an effective amount of an anti-C1s antibody, e.g., a humanized anti-C1s antibody, of the present disclosure, or a pharmaceutical composition comprising such an antibody, to an individual in need thereof. In some cases, administration of a subject anti-C1s antibody modulates the activity of complement C1s in a cell, a tissue, a fluid, or an organ of an individual, and treats the complement-mediated disease or disorder.

Certain aspects of the present disclosure provide methods of inhibiting activation of complement component C4 in an individual, the methods comprising administering to the individual an effective amount of an anti-C1s antibody, e.g., a humanized anti-C1s antibody, of the present disclosure or a pharmaceutical composition comprising such an antibody. The present disclosure provides methods of inhibiting complement C1s activity in an individual, the methods comprising administering to the individual an effective amount of an anti-C1s antibody, e.g., a humanized anti-C1s antibody, of the present disclosure or a pharmaceutical composition comprising such an antibody. The present disclosure provides methods of reducing the level of a complement component cleavage product in an individual (e.g., in a fluid, tissue, or organ in an individual), the methods comprising administering to the individual an effective amount of an anti-C1s antibody, e.g., a humanized anti-C1s antibody, of the present disclosure or a pharmaceutical composition comprising such an antibody.

In some cases, a method of the present disclosure to treat an individual having a complement-mediated disease or disorder comprises administering to the individual an effective amount of an anti-C1s antibody, e.g., a humanized anti-C1s antibody, of the present disclosure or an effective amount of a pharmaceutical composition comprising: a) an anti-C1s antibody, e.g., a humanized anti-C1s antibody, of the present disclosure; and b) a pharmaceutically acceptable excipient suitable for administration to such individual. In some embodiments, the individual is a mammal. In some embodiments, the individual is a human. Administration can be by any route known to those skilled in the art, including those disclosed herein. In some embodiments, administering is intravenous. In some embodiments, administering is intrathecal. In some embodiments, administering is subcutaneous. In some embodiments, administering intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the level of a complement component cleavage product in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the level of a complement component cleavage product in the individual (e.g., in a fluid, tissue, or organ in the individual) by at least about 1%, by at least about 5%, by at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the complement component cleavage product in the fluid, tissue, or organ in the absence of treatment with the anti-C1s antibody, e.g., before treatment with the anti-C1s antibody. In some embodiments, the individual is a mammal. In some embodiments, the individual is a human. Administering can be by any route known to those skilled in the art, including those disclosed herein. In some embodiments, administering is intravenous. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the activity of the classical complement pathway in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces, within about 48 hours, within about 24 hours, within about 12 hours, within about 8 hours, or within about 4 hours of administration of the anti-C1s antibody, the activity of the classical complement pathway in the individual (e.g., in a fluid, tissue, or organ in the individual), by at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the activity of the classical complement pathway in the fluid, tissue, or organ in the absence of treatment with the anti-C1s antibody, e.g., before treatment with the anti-C1s antibody. In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular. The level of activity of the classical complement pathway can be determined using any of a variety of methods. As one non-limiting example, the activity of the classical complement pathway can be determined ex vivo, e.g., by determining the level of activity of the classical complement pathway in a blood, serum, or plasma sample obtained from the individual. For example, the classical complement pathway in the blood, serum, or plasma sample can be activated ex vivo, and the amount of a complement component cleavage product (such as C5b-9) generated by such activation can be determined.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the activity of the classical complement pathway in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces, within about 48 hours, within about 24 hours, within about 12 hours, within about 8 hours, or within about 4 hours of administration of the anti-C1s antibody, the level of activity of the classical complement pathway in the individual (e.g., in a fluid, tissue, or organ in the individual), by at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the activity of the classical complement pathway in the fluid, tissue, or organ in the absence of treatment with the anti-C1s antibody, e.g., before treatment with the anti-C1s antibody. In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the activity of the classical complement pathway in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, maintains a reduction in the level of activity of the classical complement pathway in the individual (e.g., in a fluid, tissue, or organ in the individual) of at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the activity of the classical complement pathway in the fluid, tissue, or organ in the absence of treatment with the anti-C1s antibody, e.g., before treatment with the anti-C1s antibody, where the reduction is maintained for a period of time of from about 4 hours to about 30 days (e.g., from 4 hours to 8 hours, from 8 hours to 24 hours, from 2 days to 4 days, from 4 days to 7 days, from 7 days to 14 days, from 14 days to 21 days, or from 21 days to 30 days). In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the activity of the classical complement pathway in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, maintains a reduction in the level of activity of the classical complement pathway in the individual (e.g., in a fluid, tissue, or organ in the individual) of at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of activity of the classical complement pathway in the fluid, tissue, or organ in the absence of treatment with the anti-C1s antibody, e.g., before treatment with the anti-C1s antibody, where the reduction is maintained for a period of time of from about 4 hours to about 21 days (e.g., from 4 hours to 8 hours, from 8 hours to 24 hours, from 2 days to 4 days, from 4 days to 7 days, from 7 days to 14 days, or from 14 days to 21 days). In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the level of a complement component cleavage product in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody of the present disclosure, is an amount that, when administered in one or more doses to an individual in need thereof, reduces, within about 48 hours, within about 24 hours, within about 12 hours, within about 8 hours, or within about 4 hours of administration of the anti-C1s antibody, e.g., the humanized anti-C1s antibody, the level of a complement component cleavage product in the individual (e.g., in a fluid, tissue, or organ in the individual), by at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the complement component cleavage product in the fluid, tissue, or organ in the absence of treatment with the anti-C1s antibody, e.g., before treatment with the anti-C1s antibody. In some embodiments, the individual is a mammal. In some embodiments, the individual is a human. Administration of the anti-C1s antibody, e.g., the humanized anti-C1s antibody can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the level of a complement component cleavage product in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces, within about 48 hours, within about 24 hours, within about 12 hours, within about 8 hours, or within about 4 hours of administration of the anti-C1s antibody, the level of a complement component cleavage product in the individual (e.g., in a fluid, tissue, or organ in the individual), by at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the complement component cleavage product in the fluid, tissue, or organ in the absence of treatment with the anti-C1s antibody, e.g., before treatment with the anti-C1s antibody. In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the level of a complement component cleavage product in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, maintains a reduction in the level of a complement component cleavage product in the individual (e.g., in a fluid, tissue, or organ in the individual) of at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the complement component cleavage product in the fluid, tissue, or organ in the absence of treatment with the anti-C1s antibody, e.g., before treatment with the anti-C1s antibody, where the reduction is maintained for a period of time of from about 4 hours to about 30 days (e.g., from 4 hours to 8 hours, from 8 hours to 24 hours, from 2 days to 4 days, from 4 days to 7 days, from 7 days to 14 days, from 14 days to 21 days, or from 21 days to 30 days). In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces the level of a complement component cleavage product in the individual (e.g., in a fluid, tissue, or organ in the individual). In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, maintains a reduction in the level of a complement component cleavage product in the individual (e.g., in a fluid, tissue, or organ in the individual) of at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the level of the complement component cleavage product in the fluid, tissue, or organ in the absence of treatment with the anti-C1s antibody, e.g., before treatment with the anti-C1s antibody, where the reduction is maintained for a period of time of from about 4 hours to about 21 days (e.g., from 4 hours to 8 hours, from 8 hours to 24 hours, from 2 days to 4 days, from 4 days to 7 days, from 7 days to 14 days, or from 14 days to 21 days). In some embodiments, the individual is a mammal. In some embodiments, the individual is a human. Administration of the anti-C1s antibody, e.g., the humanized anti-C1s antibody, can be by any route known to those skilled in the art, including those disclosed herein. In some embodiments, the route of administration is intrathecal. In some embodiments, the route of administration is intravenous. In some embodiments, the route of administration is subcutaneous. In some embodiments, the route of administration is intramuscular.

In some cases, an "effective amount" of an anti-C1s antibody, e.g., a humanized anti-C1s antibody, of the present disclosure, or an "effective amount" of a subject pharmaceutical composition comprising an anti-C1s antibody, e.g., a humanized anti-C1s antibody, of the present disclosure, is an amount that, when administered in one or more doses to an individual in need thereof, reduces production of C4b2a (i.e., complement C4b and C2a complex; also known as "C3 convertase") in the individual (or in a fluid, tissue, or organ of the individual) by at least about 1%, at least about 5%, at least about 10%, at least about 20%, at least about 30%, at least about 40%, at least about 50%, at least about 60%, at least about 65%, at least about 70%, at least about 75%, at least about 80%, at least about 85%, at least about 90%, at least about 95%, or about 100%, compared to the amount of C4b2a produced in the individual, or the fluid, tissue, or organ, in the absence of treatment with the anti-C1s antibody, e.g., before treatment with the anti-C1s antibody. In some embodiments, the individual is a mammal. In some embodiments, the individual is a human. Administering can be by any route known to those skilled in the art, including those disclosed herein. In some embodiments, administering is intravenous. In some embodiments, the route of administration is intrathecal. In some embodiments, the route of administration is intravenous. In some embodiments, the route of administration is subcutaneous. In some embodiments, the route of administration is intramuscular.

The present disclosure provides a method to modulate complement activation. In some embodiments the method inhibits complement activation, for example to reduce production of C4b2a. In some embodiments, the present disclosure provides a method to modulate complement activation in an individual having a complement-mediated disease or disorder, the method comprising administering to the individual an anti-C1s antibody, e.g., a humanized anti-C1s antibody, of the present disclosure or a pharmaceutical composition of the present disclosure, wherein the pharmaceutical composition comprises an anti-C1s antibody, e.g., a humanized anti-C1s antibody, of the present disclosure. In some embodiments such a method inhibits complement activation. In some embodiments, the individual is a mammal. In some embodiments, the individual is a human. Administering can be by any route known to those skilled in the art, including those disclosed herein. In some embodiments, administering is intravenous. In some embodiments, administering is intrathecal. In some embodiments, administering is subcutaneous. In some embodiments, the route of administration is intramuscular.

A complement-mediated disease or disorder is a disorder characterized by an abnormal amount of complement C1s or an abnormal level of complement C1s proteolytic activity in a cell, a tissue, a fluid, or an organ of an individual.

In some cases, a complement-mediated disease or disorder is characterized by the presence in a cell, a tissue, or a fluid of an elevated (higher than normal) amount of C1s or of an elevated level of complement C1s activity. For example, in some cases, a complement-mediated disease or disorder is characterized by the presence in brain tissue and/or cerebrospinal fluid of an elevated amount and/or an elevated activity of C1s. A "higher than normal" amount of C1s in a cell, a tissue, or a fluid indicates that the amount of C1s in the cell, tissue or fluid is higher than a normal, control level, e.g., higher than a normal, control level for an individual or population of individuals of the same age group. A "higher than normal" level of C1s activity in a cell, a tissue, an organ, or a fluid indicates that the proteolytic cleavage effected by C1s in the cell, tissue, organ, or fluid is higher than a normal, control level, e.g., higher than a normal, control level for an individual or population of individuals of the same age group. In some cases, an individual having a complement-mediated disease or disorder exhibits one or more additional symptoms of such a disease or disorder.

In other cases, a complement-mediated disease or disorder is characterized by the presence in a cell, a tissue, or a fluid of a lower than normal amount of C1s or of a lower level of complement C1s activity. For example, in some cases, a complement-mediated disease or disorder is characterized by the presence in brain tissue and/or cerebrospinal fluid of a lower amount and/or a lower activity of C1s. A "lower than normal" amount of C1s in a cell, a tissue, or a fluid indicates that the amount of C1s in the cell, tissue or fluid is lower than a normal, control level, e.g., lower than a normal, control level for an individual or population of individuals of the same age group. A "lower than normal" level of C1s activity in a cell, a tissue, or a fluid indicates that the proteolytic cleavage effected by C1s in the cell, tissue or fluid is lower than a normal, control level, e.g., lower than a normal, control level for an individual or population of individuals of the same age group. In some cases, an individual having a complement-mediated disease or disorder exhibits one or more additional symptoms of such a disease or disorder.

A complement-mediated disease or disorder is a disease or disorder in which the amount or activity of complement C1s is such as to cause disease or disorder in an individual. In some embodiments, the complement-mediated disease or disorder is selected from the group consisting of alloimmune disease, autoimmune disease, cancer, hematological disease, infectious disease, inflammatory disease, ischemia-reperfusion injury, neurodegenerative disease, neurodegenerative disorder, ocular disease, renal disease, transplant rejection, vascular disease, and vasculitis disease. In some embodiments, the complement-mediated disease or disorder is an autoimmune disease. In some embodiments, the complement-mediated disease or disorder is an alloimmune disease. In some embodiments, the complement-mediated disease or disorder is cancer. In some embodiments, the complement-mediated disease or disorder is an infectious disease. In some embodiments, the complement-mediated disease or disorder is an inflammatory disease. In some embodiments, the complement-mediated disease or disorder is a hematological disease. In some embodiments, the complement-mediated disease or disorder is an ischemia-reperfusion injury. In some embodiments, the complement-mediated disease or disorder is ocular disease. In some embodiments, the complement-mediated disease or disorder is a renal disease. In some embodiments, the complement-mediated disease or disorder is transplant rejection. In some embodiments, the complement-mediated disease or disorder is antibody-mediated transplant rejection. In some embodiments, the complement-mediated disease or disorder is a vascular disease. In some embodiments, the complement-mediated disease or disorder is a vasculitis disorder. In some embodiments, the complement-mediated disease or disorder is a neurodegenerative disease or disorder. In some embodiments, the complement-mediated disease is a neurodegenerative disease. In some embodiments, the complement-mediated disorder is a neurodegenerative disorder.

Examples of a complement-mediated disease or disorder include, but are not limited to, age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases (including, e.g., autoimmune hemolytic anemia (AIHA); warm AIHA; mixed AIHA; etc.), Barraquer-Simons syndrome, Behçet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, Evan's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barré syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, Epidermolysis bullosa acquisita, delayed hemolytic transfusion reaction, hypocomplementemic urticarial vasculitis syndrome, pseudophakic bullous keratopathy, platelet refractoriness, chronic inflammatory demyelinating polyneuropathy (CIDP), myelodysplastic syndrome (MDS), miller fisher syndrome, acute inflammatory demyelinating polyneuropathy (AIDP), acute motor axonal neuropathy (AMAN), acute motor and sensory axonal neuropathy (AMSAN), and pharyngeal-cervical-brachial variant. In one embodiment, the complement-mediated disease or disorder comprises bullous pemphigoid. In one embodiment, the complement-mediated disease or disorder comprises cold agglutinin disease. In one embodiment, the complement-mediated disease or disorder comprises autoimmune hemolytic anemia (AIHA). In one embodiment, the complement-mediated disease or disorder comprises immunothrombocytopenic purpura (ITP). In one embodiment, the complement-mediated disease or disorder comprises multifocal motor neuropathy. In one embodiment, the complement-mediated disease or disorder comprises neuromyelitis optica.

In some embodiments, the complement-mediated disease or disorder comprises Alzheimer's disease. In some embodiments, the complement-mediated disease or disorder comprises Parkinson's disease. In some embodiments, the complement-mediated disease or disorder comprises transplant rejection. In some embodiments, the complement-mediated disease or disorder is antibody-mediated transplant rejection.

In some embodiments, an anti-C1s antibody, e.g., a humanized anti-C1s antibody, of the present disclosure prevents or delays the onset of at least one symptom of a complement-mediated disease or disorder in an individual. In some embodiment, an anti-C1s antibody of the present disclosure reduces or eliminates at least one symptom of a complement-mediated disease or disorder in an individual. Examples of symptoms include, but are not limited to, symptoms associated with autoimmune disease, cancer, hematological disease, infectious disease, inflammatory disease, ischemia-reperfusion injury, neurodegenerative disease, neurodegenerative disorder, renal disease, transplant rejection, ocular disease, vascular disease, or a vasculitis disorder. The symptom can be a neurological symptom, for example, impaired cognitive function, memory impairment, loss of motor function, etc. The symptom can also be the activity of C1s protein in a cell, tissue, or fluid of an individual. The symptom can also be the extent of complement activation in a cell, tissue, or fluid of an individual.

In some embodiments, administering an anti-C1s antibody, e.g., a humanized anti-C1s antibody, of the present disclosure to an individual modulates complement activation in a cell, tissue, or fluid of an individual. In some embodiments, administration of a subject anti-C1s antibody to an individual inhibits complement activation in a cell, tissue, or fluid of an individual. For example, in some embodiments, a subject anti-C1s antibody, e.g., a humanized anti-C1s antibody, when administered in one or more doses as monotherapy or in combination therapy to an individual having a complement-mediated disease or disorder, inhibits complement activation in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, at least about 95%, or 100%, compared to complement activation in the individual before treatment with the anti-C1s antibody.

In some embodiments, an anti-C1s antibody, e.g., a humanized anti-C1s antibody, of the present disclosure reduces C3 deposition onto red blood cells; for example, in some embodiments, an anti-C1s antibody, e.g., an anti-C1s antibody, of the present disclosure reduces deposition of C3b, iC3b, etc., onto RBCs). In some embodiments, an anti-C1s antibody, e.g., an anti-C1s antibody, of the present disclosure inhibits complement-mediated red blood cell lysis.

In some embodiments, an anti-C1s antibody, e.g., a humanized anti-C1s antibody, of the present disclosure reduces C3 deposition onto platelets; for example, in some embodiments, an anti-C1s antibody, e.g., an anti-C1s antibody, of the present disclosure reduces deposition of C3b, iC3b, etc., onto platelets).

In some embodiments, administering an anti-C1s antibody, e.g., a humanized anti-C1s antibody, of the present disclosure results in an outcome selected from the group consisting of: (a) a reduction in complement activation; (b) an improvement in cognitive function; (c) a reduction in neuron loss; (d) a reduction in glial cell activation; (e) a reduction in lymphocyte infiltration; (f) a reduction in macrophage infiltration; (g) a reduction in antibody deposition, (h) a reduction in glial cell loss; (i) a reduction in oligodendrocyte loss; (j) a reduction in dendritic cell infiltration; (k) a reduction in neutrophil infiltration; (l) a reduction in red blood cell lysis; (m) a reduction in red blood cell phagocytosis; (n) a reduction in platelet phagocytosis; (o) a reduction in platelet lysis; (p) an improvement in transplant graft survival; (q) a reduction in macrophage mediated phagocytosis; (r) an improvement in vision; (s) an improvement in motor control; (t) an improvement in thrombus formation; (u) an improvement in clotting; (v) an improvement in kidney function; (w) a reduction in antibody mediated complement activation; (x) a reduction in autoantibody mediated complement activation; (y) an improvement in anemia; (aa) reduction of demyelination; (ab) reduction of eosinophilia; (ac) a reduction of C3 deposition on red blood cells (e.g., a reduction of deposition of C3b, iC3b, etc., onto RBCs); and (ad) a reduction in C3 deposition on platelets (e.g., a reduction of deposition of C3b, iC3b, etc., onto platelets); and (ae) a reduction of anaphylatoxin toxin production; (af) a reduction in autoantibody mediated blister formation; (ag) a reduction in autoantibody induced pruritis; (ah) a reduction in autoantibody induced erythematosus; (ai) a reduction in autoantibody mediated skin erosion; (aj) a reduction in red blood cell destruction due to transfusion reactions; (ak) a reduction in red blood cell lysis due to alloantibodies; (al) a reduction in hemolysis due to transfusion reactions; (am) a reduction in allo-antibody mediated platelet lysis; (an) a reduction in platelet lysis due to transfusion reactions; (ao) a reduction in mast cell activation; (ap) a reduction in mast cell histamine release; (aq) a reduction in vascular permeability; (ar) a reduction in edema; (as) a reduction in complement deposition on transplant graft endothelium; (at) a reduction of anaphylatoxin generation in transplant graft endothelium; (au) a reduction in the separation of the dermal-epidermal junction; (av) a reduction in the generation of anaphylatoxins in the dermal-epidermal junction; (aw) a reduction in alloantibody mediated complement activation in transplant graft endothelium; (ax) a reduction in antibody mediated loss of the neuromuscular junction; (ay) a reduction in complement activation at the neuromuscular junction; (az) a reduction in anaphylatoxin generation at the neuromuscular junction; (ba) a reduction in complement deposition at the neuromuscular junction; (bb) a reduction in paralysis; (bc) a reduction in numbness; (bd) increased bladder control; (be) increased bowel control; (bf) a reduction in mortality associated with autoantibodies; (bg) a reduction in morbidity associated with autoantibodies; (bh) a reduction in Schwann cell damage; (bi) a reduction in Schwann cell loss; (bj) a reduction in motor neuron damage; (bk) a reduction in motor neuron axonal loss; (bl) an amelioration of action potential conduction block; (bm) an improvement in upper or lower limb movement; (bn) an improvement in neuronal sensory-motor deficits, and (bo) any combination thereof.

In some embodiments, an anti-C1s antibody, e.g., a subject anti-C1s antibody, when administered in one or more doses as monotherapy or in combination therapy to an individual having a complement-mediated disease or disorder, is effect to achieve a reduction of at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: (a) complement activation; (b) decline in cognitive function; (c) neuron loss; (d) glial cell activation; (e) lymphocyte infiltration; (f) macrophage infiltration; (g) antibody deposition, (h) glial cell loss; (i) oligodendrocyte loss; (j) dendritic cell infiltration; (k) neutrophil infiltration; (l) red blood cell lysis; (m) red blood cell phagocytosis; (n) platelet phagocytosis; (o) platelet lysis; (p) transplant graft rejection; (q) macrophage mediated phagocytosis; (r) vision loss; (s) antibody mediated complement activation; (t) autoantibody mediated complement activation; (u) demyelination; (v) eosinophilia; (w) or any combination thereof, compared to the level or degree of the outcome in the individual before treatment with the anti-C1s antibody.

In some embodiments, a subject anti-C1s antibody, when administered in one or more doses as monotherapy or in combination therapy to an individual having a complement-mediated disease or disorder, is effect to achieve an improvement of at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, of one or more of the following outcomes: a) cognitive function; b) transplant graft survival; c) vision; d) motor control; e) thrombus formation; f) clotting; g) kidney function; h) hematocrit (red blood cell count); and i) any combination thereof, compared to the level or degree of the outcome in the individual before treatment with the anti-C1s antibody.

In some embodiments, administering an anti-C1s antibody, e.g., a humanized anti-C1s antibody, of the present disclosure to an individual reduces complement activation in the individual. For example, in some embodiments, a subject anti-C1s antibody, when administered in one or more doses as monotherapy or in combination therapy to an individual having a complement-mediated disease or disorder, reduces complement activation in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to complement activation in the individual before treatment with the anti-C1s antibody.

In some embodiments, administering an anti-C1s antibody, e.g., a humanized anti-C1s antibody, of the present disclosure improves cognitive function in the individual. For example, in some embodiments, a subject anti-C1s antibody, when administered in one or more doses as monotherapy or in combination therapy to an individual having a complement-mediated disease or disorder, improves cognitive function in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to the cognitive function in the individual before treatment with the anti-C1s antibody.

In some embodiments, administering an anti-C1s antibody, e.g., a humanized anti-C1s antibody, of the present disclosure reduces the rate of decline in cognitive function in the individual. For example, in some embodiments, a subject anti-C1s antibody, when administered in one or more doses as monotherapy or in combination therapy to an individual having a complement-mediated disease or disorder, reduces the rate of decline of cognitive function in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to the rate of decline in cognitive function in the individual before treatment with the anti-C1s antibody.

In some embodiments, administering an anti-C1s antibody, e.g., a humanized anti-C1s antibody, of the present disclosure to an individual reduces neuron loss in the individual. For example, in some embodiments, a subject anti-C1s antibody, when administered in one or more doses as monotherapy or in combination therapy to an individual having a complement-mediated disease or disorder, reduces neuron loss in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to neuron loss in the individual before treatment with the anti-C1s antibody.

In some embodiments, administering an anti-C1s antibody, e.g., a humanized anti-C1s antibody, of the present disclosure to an individual reduces glial cell activation in the individual. For example, in some embodiments, a subject anti-C1s antibody, when administered in one or more doses as monotherapy or in combination therapy to an individual having a complement-mediated disease or disorder, reduces glial activation in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to glial cell activation in the individual before treatment with the anti-C1s antibody. In some embodiments, the glial cells are astrocytes or microglia.

In some embodiments, administering an anti-C1s antibody, e.g., a humanized anti-C1s antibody of the present disclosure to an individual reduces lymphocyte infiltration in the individual. For example, in some embodiments, a subject anti-C1s antibody, when administered in one or more doses as monotherapy or in combination therapy to an individual having a complement-mediated disease or disorder, reduces lymphocyte infiltration in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to lymphocyte infiltration in the individual before treatment with the anti-C1s antibody.

In some embodiments, administering an anti-C1s antibody, e.g., a humanized anti-C1s antibody, of the present disclosure to an individual reduces macrophage infiltration in the individual. For example, in some embodiments, an anti-C1s antibody, e.g., a humanized anti-C1s antibody, of the present disclosure, when administered in one or more doses as monotherapy or in combination therapy to an individual having a complement-mediated disease or disorder, reduces macrophage infiltration in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to macrophage infiltration in the individual before treatment with the anti-C1s antibody.

In some embodiments, administering an anti-C1s antibody, e.g., a humanized anti-C1s antibody, of the present disclosure to an individual reduces antibody deposition in the individual. For example, in some embodiments, an anti-C1s antibody, e.g., a humanized anti-C1s antibody, of the present disclosure, when administered in one or more doses as monotherapy or in combination therapy to an individual having a complement-mediated disease or disorder, reduces antibody deposition in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to antibody deposition in the individual before treatment with the anti-C1s antibody.

In some embodiments, administering an anti-C1s antibody of the present disclosure to an individual reduces anaphylatoxin (e.g., C3a, C4a, C5a) production in an individual. For example, in some embodiments, an anti-C1s antibody, e.g., a humanized anti-C1s antibody, of the present disclosure, when administered in one or more doses as monotherapy or in combination therapy to an individual having a complement-mediated disease or disorder, reduces anaphylatoxin production in the individual by at least about 1%, at least about 5%, at least about 10%, at least about 15%, at least about 20%, at least about 25%, at least about 30%, at least about 40%, at least about 50%, at least about 60%, at least about 70%, at least about 80%, at least about 90%, or more than 90%, compared to the level of anaphylatoxin production in the individual before treatment with the anti-C1s antibody.

The present disclosure provides for use of an anti-C1s antibody, e.g., a humanized anti-C1s antibody, of the present disclosure or a pharmaceutical composition comprising an anti-C1s antibody, e.g., a humanized anti-C1s antibody, of the present disclosure and a pharmaceutically acceptable excipient to treat an individual having a complement-mediated disease or disorder. In some embodiments, the present disclosure provides for use of an anti-C1s antibody, e.g., a humanized anti-C1s antibody, of the present disclosure to treat an individual having a complement-mediated disease or disorder. In some embodiments, the present disclosure provides for use of a pharmaceutical composition comprising an anti-C1s antibody, e.g., a humanized anti-C1s antibody, of the present disclosure and a pharmaceutically acceptable excipient to treat an individual having a complement-mediated disease or disorder.

The present disclosure provides for use of an anti-C1s antibody, e.g., a humanized anti-C1s antibody, of the present disclosure in the manufacture of a medicament for the treatment of an individual having a complement-mediated disease or disorder.

The present disclosure provides for use of an anti-C1s antibody, e.g., a humanized anti-C1s antibody, of the present disclosure or a pharmaceutical composition comprising an anti-C1s antibody, e.g., a humanized anti-C1s antibody, of the present disclosure and a pharmaceutically acceptable excipient to inhibit complement activation. In some embodiments, the present disclosure provides for use of an anti-C1s antibody, e.g., a humanized anti-C1s antibody, of the present disclosure or a pharmaceutical composition comprising an anti-C1s antibody, e.g., a humanized anti-C1s antibody, of the present disclosure and a pharmaceutically acceptable excipient to inhibit complement activation in an individual having a complement-mediated disease or disorder. In some embodiments, the present disclosure provides for use of an anti-C1s antibody, e.g., a humanized anti-C1s antibody, of the present disclosure to inhibit complement activation in an individual having a complement-mediated disease or disorder. In some embodiments, the present disclosure provides for use of a pharmaceutical composition comprising an anti-C1s antibody, e.g., a humanized anti-C1s antibody, of the present disclosure and a pharmaceutically acceptable excipient to inhibit complement activation in an individual having a complement-mediated disease or disorder.

The present disclosure provides for use of an anti-C1s antibody, e.g., a humanized anti-C1s antibody, of the present disclosure in the manufacture of a medicament for modulating complement activation. In some embodiments, the medicament inhibits complement activation. In some embodiments, the medicament inhibits complement activation in an individual having a complement-mediated disease or disorder.

The present disclosure provides for an anti-C1s antibody, e.g., a humanized anti-C1s antibody, of the present disclosure or a pharmaceutical composition comprising an anti-C1s antibody, e.g., a humanized anti-C1s antibody, of the present disclosure and a pharmaceutically acceptable excipient for use in medical therapy. In some embodiments, the present disclosure provides for an anti-C1s antibody, e.g., a humanized anti-C1s antibody, of the present disclosure for use in medical therapy. In some embodiments, the present disclosure provides for a pharmaceutical composition comprising an anti-C1s antibody, e.g., a humanized anti-C1s antibody, of the present disclosure and a pharmaceutically acceptable excipient for use in medical therapy.

The present disclosure provides for an anti-C1s antibody, e.g., a humanized anti-C1s antibody, of the present disclosure or a pharmaceutical composition comprising an anti-C1s antibody, e.g., a humanized anti-C1s antibody, of the present disclosure and a pharmaceutically acceptable excipient for treating an individual having a complement-mediated disease or disorder. In some embodiments, the present disclosure provides for an anti-C1s antibody, e.g., a humanized anti-C1s antibody, of the present disclosure for treating an individual having a complement-mediated disease or disorder. In some embodiments, the present disclosure provides for a pharmaceutical composition comprising an anti-C1s antibody, e.g., a humanized anti-C1s antibody, of the present disclosure and a pharmaceutically acceptable excipient for treating an individual having a complement-mediated disease or disorder.

The present disclosure provides for an anti-C1s antibody, e.g., a humanized anti-C1s antibody, of the present disclosure or a pharmaceutical composition comprising an anti-C1s antibody, e.g., a humanized anti-C1s antibody, of the present disclosure and a pharmaceutically acceptable excipient for modulating complement activation. In some embodiments, the present disclosure provides for an anti-C1s antibody, e.g., a humanized anti-C1s antibody, of the present disclosure for modulating complement activation. In some embodiments, the present disclosure provides for a pharmaceutical composition comprising an anti-C1s antibody, e.g., a humanized anti-C1s antibody, of the present disclosure and a pharmaceutically acceptable excipient for modulating complement activation. In some embodiments, the anti-C1s antibody inhibits complement activation.

EXAMPLES OF NON-LIMITING ASPECTS OF THE DISCLOSURE

Aspects, including embodiments, of the present subject matter described above can be beneficial alone or in combination, with one or more other aspects or embodiments. Without limiting the foregoing description, certain non-limiting aspects of the disclosure numbered 1-37 are provided below. As will be apparent to those of skill in the art upon reading this disclosure, each of the individually numbered aspects can be used or combined with any of the preceding or following individually numbered aspects. This is intended to provide support for all such combinations of aspects and is not limited to combinations of aspects explicitly provided below:

Aspect 1. A humanized antibody that specifically binds complement component C1s, wherein the antibody comprises:
a) a heavy chain comprising:

```
i) a VH region comprising the amino acid sequence:
                                          (SEQ ID NO: 26)
(Q/E)VQL(V/Q)QSGAE(V/L)KKPGASVK(L/V)SC(T/A)ASGFNIK

DDYIHWV(K/R)QAPGQGLEWIGRIDPADGHTKYAPKFQVK(V/A)TITA

DTST(S/N)TAY(L/M)(E/Q)LSSL(R/T)SEDTAVYYCARYGYGREVF

DYWGQGTTVTVSS;
and
``` ii) an Fc region comprising an amino acid sequence having at least 98% amino acid sequence identity with the amino acid sequence set forth in SEQ ID NO:28, wherein amino acid 308 is Leu and amino acid 314 is Ser; and
b) a light chain comprising:

```
i) a VL region comprising the amino acid sequence:
                                          (SEQ ID NO: 27)
DIVLTQSPDSLAVSLGERATISCKASQSVDYDGDSYMNWYQQK(T/P)GQ

PPK(I/L)LIYDASNLESGIPARFSGSGSGTDFTLTISSLE(E/P)EDFA (I/V)YYCQQSNEDPWTFGGGTKVEIK;
and
``` ii) a light chain constant region.

Aspect 2. The humanized antibody of aspect 1, comprising: a) a VH region comprising SEQ ID NO:10; and b) a VL region comprising SEQ ID NO:20.

Aspect 3. The humanized antibody of aspect 1, comprising: a) a VH region comprising SEQ ID NO:10; and b) a VL region comprising SEQ ID NO:22.

Aspect 4. The humanized antibody of aspect 1, comprising: a) a VH region comprising SEQ ID NO:10; and b) a VL region comprising SEQ ID NO:24.

Aspect 5. The humanized antibody of aspect 1, comprising: a) a VH region comprising SEQ ID NO:12; and b) a VL region comprising SEQ ID NO:20.

Aspect 6 The humanized antibody of aspect 1, comprising: a) a VH region comprising SEQ ID NO:12; and b) a VL region comprising SEQ ID NO:22.

Aspect 7. The humanized antibody of aspect 1, comprising: a) a VH region comprising SEQ ID NO:12; and b) a VL region comprising SEQ ID NO:24.

Aspect 8. The humanized antibody of aspect 1, comprising: a) a VH region comprising SEQ ID NO:14; and b) a VL region comprising SEQ ID NO:20.

Aspect 9. The humanized antibody of aspect 1, comprising: a) a VH region comprising SEQ ID NO:14; and b) a VL region comprising SEQ ID NO:22.

Aspect 10. The humanized antibody of aspect 1, comprising: a) a VH region comprising SEQ ID NO:14; and b) a VL region comprising SEQ ID NO:24.

Aspect 11. The humanized antibody of aspect 1, comprising: a) a VH region comprising SEQ ID NO:16; and b) a VL region comprising SEQ ID NO:20.

Aspect 12. The humanized antibody of aspect 1, comprising: a) a VH region comprising SEQ ID NO:16; and b) a VL region comprising SEQ ID NO:22.

Aspect 13. The humanized antibody of aspect 1, comprising: a) a VH region comprising SEQ ID NO:16; and b) a VL region comprising SEQ ID NO:24.

Aspect 14. The humanized antibody of aspect 1, comprising: a) a VH region comprising SEQ ID NO:18; and b) a VL region comprising SEQ ID NO:20.

Aspect 15. The humanized antibody of aspect 1, comprising: a) a VH region comprising SEQ ID NO:18; and b) a VL region comprising SEQ ID NO:22.

Aspect 16. The humanized antibody of aspect 1, comprising: a) a VH region comprising SEQ ID NO:18; and b) a VL region comprising SEQ ID NO:24.

Aspect 17. The humanized antibody of aspect 1, wherein the light chain constant region is a human kappa light chain constant region.

Aspect 18. The humanized antibody of aspect 1, wherein the heavy chain constant region comprises the amino acid sequence set forth in SEQ ID NO:28.

Aspect 19. The humanized antibody of aspect 1, wherein: a) the heavy chain comprises the amino acid sequence set forth in SEQ ID NO:29; and b) the light chain comprises the amino acid sequence set forth in SEQ ID NO:30.

Aspect 20. A composition comprising: a) the humanized antibody of any one of aspects 1-19; and b) a pharmaceutically acceptable excipient.

Aspect 21. A container comprising the composition of aspect 20.

Aspect 22. The container of aspect 21, wherein the container is sterile.

Aspect 23. The container of aspect 21 or aspect 22, wherein the container is a vial, a bottle, or a syringe.

Aspect 24. A method of reducing the level of a complement component cleavage product in an individual, the method comprising administering to the individual the antibody of any one of aspects 1-19, or the composition of aspect 20, in an amount effective to inhibit C1s and to reduce the level of the cleavage product.

Aspect 25. The method of aspect 24, wherein the complement component cleavage product is a C4 cleavage product.

Aspect 26. The method of aspect 25, wherein the complement component cleavage product is a C2 cleavage product.

Aspect 27. The method of aspect 25, wherein the complement component cleavage product is a C3 cleavage product.

Aspect 28. The method of any one of aspects 24-27, wherein the individual is a human.

Aspect 29. The method of any one of aspects 24-28, wherein the administering is intravenous.

Aspect 30. The method of any one of aspects 24-28, wherein the administering is intramuscular.

Aspect 31. The method of any one of aspects 24-28, wherein the administering is intrathecal.

Aspect 32. The method of any one of aspects 24-28, wherein the administering is subcutaneous.

Aspect 33. The method of any one of aspects 24-28, wherein said reducing is effective to treat a complement-mediated disorder.

Aspect 34. The method of aspect 33, wherein the complement-mediated disorder is an alloimmune disorder.

Aspect 35. The method of aspect 33, wherein the complement-mediated disorder is an autoimmune disorder.

Aspect 36. A method of inhibiting C1s-mediated cleavage of a complement component in an individual, the method comprising administering to the individual the antibody of any one of aspects 1-19, or the composition of aspect 20, in an amount effective to inhibit C1s-mediated cleavage of a complement component.

Aspect 37. A method of treating a complement-mediated disease or disorder in an individual, the method comprising administering to the individual the antibody of any one of aspects 1-19, or the composition of aspect 20, in an amount effective to treat the complement-mediated disease or disorder.

Aspect 38. An antibody, comprising a heavy chain and a light chain, wherein the heavy chain comprises a VH region and a heavy chain constant region, and the light chain comprises a VL region;
  wherein the VL region comprises a VL CDR1, a VL CDR2, and a VL CDR3, and wherein the VH region comprises a VH CDR1, a VH CDR2, and a VH CDR3;
  wherein the VL CDR1 comprises SEQ ID NO: 1;
  wherein the VL CDR2 comprises SEQ ID NO: 2;
  wherein the VL CDR3 comprises SEQ ID NO: 3;
  wherein the VH CDR1 comprises SEQ ID NO: 4;
  wherein the VH CDR2 comprises SEQ ID NO: 5;
  wherein the VH CDR3 comprises SEQ ID NO: 6;
  wherein the heavy chain constant region comprises an IgG4 constant region, wherein amino acid residue 308 of the heavy chain constant region corresponding to SEQ ID NO: 28 is Leu, and amino acid residue 314 of the heavy chain constant region corresponding to SEQ ID NO: 28 is Ser;
  and wherein the antibody specifically binds activated C1s.

Aspect 39. The antibody of aspect 38, wherein amino acid residue 108 of the heavy chain constant region corresponding to SEQ ID NO: 28 is Pro.

Aspect 40. The antibody of aspect 38 or 39, wherein amino acid residue 115 of the heavy chain constant region corresponding to SEQ ID NO: 28 is Glu.

Aspect 41. An antibody, comprising a heavy chain and a light chain, wherein the heavy chain comprises a VH region and a heavy chain constant region, and the light chain comprises a VL region;
  wherein the VL region comprises a VL CDR1, a VL CDR2, and a VL CDR3, and wherein the VH region comprises a VH CDR1, a VH CDR2, and a VH CDR3;
  wherein the VL CDR1 comprises SEQ ID NO: 1;
  wherein the VL CDR2 comprises SEQ ID NO: 2;
  wherein the VL CDR3 comprises SEQ ID NO: 3;
  wherein the VH CDR1 comprises SEQ ID NO: 4;
  wherein the VH CDR2 comprises SEQ ID NO: 5;
  wherein the VH CDR3 comprises SEQ ID NO: 6;
  wherein the heavy chain constant region comprises SEQ ID NO: 28;
  and wherein the antibody specifically binds activated C1s.

Aspect 42. The antibody of any one of aspects 38 to 41, wherein the VL region comprises an amino acid sequence selected from the group consisting of SEQ ID NOs: 20, 22, and 24.

Aspect 43. The antibody of any one of aspects 38 to 42, wherein the VH region comprises an amino acid sequence selected from the group consisting of SEQ ID NOs: 10, 12, 14, 16, and 18.

Aspect 44. The antibody of any one of aspects 38 to 43, wherein:
  (a) the VH region comprises SEQ ID NO:10, and the VL region comprises SEQ ID NO:20;
  (b) the VH region comprises SEQ ID NO:10, and the VL region comprises SEQ ID NO:22;
  (c) the VH region comprises SEQ ID NO:10, and the VL region comprises SEQ ID NO:24;
  (d) the VH region comprises SEQ ID NO:12, and the VL region comprises SEQ ID NO:20;
  (e) the VH region comprises SEQ ID NO:12, and the VL region comprises SEQ ID NO:22;
  (f) the VH region comprises SEQ ID NO:12, and the VL region comprises SEQ ID NO:24;
  (g) the VH region comprises SEQ ID NO:14, and the VL region comprises SEQ ID NO:20;
  (h) the VH region comprises SEQ ID NO:14, and the VL region comprises SEQ ID NO:22;
  (i) the VH region comprises SEQ ID NO:14, and the VL region comprises SEQ ID NO:24;
  (j) the VH region comprises SEQ ID NO:16, and the VL region comprises SEQ ID NO:20;
  (j) the VH region comprises SEQ ID NO:16, and the VL region comprises SEQ ID NO:22;
  (k) the VH region comprises SEQ ID NO:16, and the VL region comprises SEQ ID NO:24;
  (l) the VH region comprises SEQ ID NO:18, and the VL region comprises SEQ ID NO:20;
  (m) the VH region comprises SEQ ID NO:18, and the VL region comprises SEQ ID NO:22; or
  (n) the VH region comprises SEQ ID NO:18, and the VL region comprises SEQ ID NO:24.

Aspect 45. The antibody of any one of aspects 38 to 44, wherein the VH region comprises SEQ ID NO:14, and the VL region comprises SEQ ID NO:22.

Aspect 46. The antibody of any one of aspects 38 to 45, wherein the light chain further comprises a light chain constant region.

Aspect 47. The antibody of aspect 46, wherein the light chain constant region comprises SEQ ID NO: 45.

Aspect 48. The antibody of any one of aspects 38 to 47, where the heavy chain comprises SEQ ID NO: 29.

Aspect 49. The antibody of any one of aspects 38 to 48, wherein the light chain comprises SEQ ID NO: 30.

Aspect 50. The antibody of any one of aspects 1 to 19 and 38 to 49, which is a bispecific antibody or a multispecific antibody.

Aspect 51. An immunoconjugate comprising the antibody of any one of aspects 1 to 19 and 38 to 50.

Aspect 52. A nucleotide of a set of nucleotides encoding the antibody of any one of aspects 1 to 19 and 38 to 50.

Aspect 53. A vector or a set of vectors comprising the nucleotide of the set of nucleotides of aspect 52.

Aspect 54. A host cell comprising the nucleotide of the set of nucleotides of aspect 52 or the vector or the set of vectors of aspect 53.

Aspect 55. A pharmaceutical composition comprising the antibody of any one of aspects 1 to 19 and 38 to 50, the immunoconjugate of aspect 51, the nucleotide or the set of nucleotides of aspect 52, the vector or the set of vectors of aspect 53, or the host cell of aspect 54, and a pharmaceutically acceptable excipient.

Aspect 56. A method of inhibiting a complement pathway in a subject in need thereof, comprising administering to the subject a pharmaceutically effective amount of the antibody of any one of aspects 1 to 19 and 38 to 50, the immunoconjugate of aspect 51, the nucleotide or the set of nucleotides of aspect 52, the vector or the set of vectors of aspect 53, the host cell of aspect 54, or the pharmaceutical composition of aspect 55.

Aspect 57. A method of inhibiting C1s-mediated cleavage of complement component C4 in a subject in need thereof, comprising administering to the subject a pharmaceutically effective amount of the antibody of any one of aspects 1 to 19 and 38 to 50, the immunoconjugate of aspect 51, the nucleotide or the set of nucleotides of aspect 52, the vector or the set of vectors of aspect 53, the host cell of aspect 54, or the pharmaceutical composition of aspect 55.

Aspect 58. A method of treating a complement-mediated disease or disorder in a subject in need thereof, comprising administering to the subject a pharmaceutically effective amount of the antibody of any one of aspects 1 to 19 and 38 to 50, the immunoconjugate of aspect 51, the nucleotide or the set of nucleotides of aspect 52, the vector or the set of vectors of aspect 53, the host cell of aspect 54, or the pharmaceutical composition of aspect 55.

Aspect 59. The method of aspect 58, wherein the complement-mediated disease or disorder is selected from the group consisting of age-related macular degeneration, Alzheimer's disease, amyotrophic lateral sclerosis, anaphylaxis, argyrophilic grain dementia, arthritis (e.g., rheumatoid arthritis), asthma, atherosclerosis, atypical hemolytic uremic syndrome, autoimmune diseases (including, e.g., autoimmune hemolytic anemia (AIHA); warm AIHA; mixed AIHA; etc.), Barraquer-Simons syndrome, Behçet's disease, British type amyloid angiopathy, bullous pemphigoid, Buerger's disease, C1q nephropathy, cancer, catastrophic antiphospholipid syndrome, cerebral amyloid angiopathy, cold agglutinin disease, corticobasal degeneration, Creutzfeldt-Jakob disease, Crohn's disease, cryoglobulinemic vasculitis, dementia pugilistica, dementia with Lewy Bodies (DLB), diffuse neurofibrillary tangles with calcification, Discoid lupus erythematosus, Down's syndrome, Evan's syndrome, focal segmental glomerulosclerosis, formal thought disorder, frontotemporal dementia (FTD), frontotemporal dementia with parkinsonism linked to chromosome 17, frontotemporal lobar degeneration, Gerstmann-Straussler-Scheinker disease, Guillain-Barré syndrome, Hallervorden-Spatz disease, hemolytic-uremic syndrome, hereditary angioedema, hypophosphastasis, idiopathic pneumonia syndrome, immune complex diseases, inclusion body myositis, infectious disease (e.g., disease caused by bacterial (e.g., *Neisseria meningitidis* or *Streptococcus*) viral (e.g., human immunodeficiency virus (HIV)), or other infectious agents), inflammatory disease, ischemia/reperfusion injury, mild cognitive impairment, immunothrombocytopenic purpura (ITP), molybdenum cofactor deficiency (MoCD) type A, membranoproliferative glomerulonephritis (MPGN) I, membranoproliferative glomerulonephritis (MPGN) II (dense deposit disease), membranous nephritis, multi-infarct dementia, lupus (e.g., systemic lupus erythematosus (SLE)), glomerulonephritis, Kawasaki disease, multifocal motor neuropathy, multiple sclerosis, multiple system atrophy, myasthenia gravis, myocardial infarction, myotonic dystrophy, neuromyelitis optica, Niemann-Pick disease type C, non-Guamanian motor neuron disease with neurofibrillary tangles, Parkinson's disease, Parkinson's disease with dementia, paroxysmal nocturnal hemoglobinuria, Pemphigus vulgaris, Pick's disease, postencephalitic parkinsonism, polymyositis, prion protein cerebral amyloid angiopathy, progressive subcortical gliosis, progressive supranuclear palsy, psoriasis, sepsis, Shiga-toxin *E coli* (STEC)-HuS, spinal muscular atrophy, stroke, subacute sclerosing panencephalitis, Tangle only dementia, transplant rejection, vasculitis (e.g., ANCA associated vasculitis), Wegner's granulomatosis, sickle cell disease, cryoglobulinemia, mixed cryoglobulinemia, essential mixed cryoglobulinemia, Type II mixed cryoglobulinemia, Type III mixed cryoglobulinemia, nephritis, drug-induced thrombocytopenia, lupus nephritis, Epidermolysis bullosa acquisita, delayed hemolytic transfusion reaction, hypocomplementemic urticarial vasculitis syndrome, pseudophakic bullous keratopathy, platelet refractoriness, chronic inflammatory demyelinating polyneuropathy (CIDP), myelodysplastic syndrome (MDS), miller fisher syndrome, acute inflammatory demyelinating polyneuropathy (AIDP), acute motor axonal neuropathy (AMAN), acute motor and sensory axonal neuropathy (AMSAN), pharyngeal-cervical-brachial variant, and any combination thereof.

Aspect 60. The method of aspect 58 or 59, wherein the complement-mediated disease or disorder is selected from the group consisting of bullous pemphigoid, cold agglutinin disease, autoimmune hemolytic anemia (AIHA), immunothrombocytopenic purpura (ITP), multifocal motor neuropathy, neuromyelitis optica, and any combination thereof.

Aspect 61. The method of any one of aspects 56 to 60, wherein the antibody is administered parenterally, intravenously, subcutaneously, intradermally, transdermally, intramuscularly, orally, intraocularly, intrathecally, intraperitoneally, intranasally, buccally, sublingually, rectally, vaginally, or via pulmonary route.

EXAMPLES

The following examples are put forth so as to provide those of ordinary skill in the art with a complete disclosure and description of how to make and use the present disclosure, and are not intended to limit the scope of what the inventors regard as their disclosure nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); and the like.

Example 1: Humanized Anti-aC1s Variants

Figure 9:
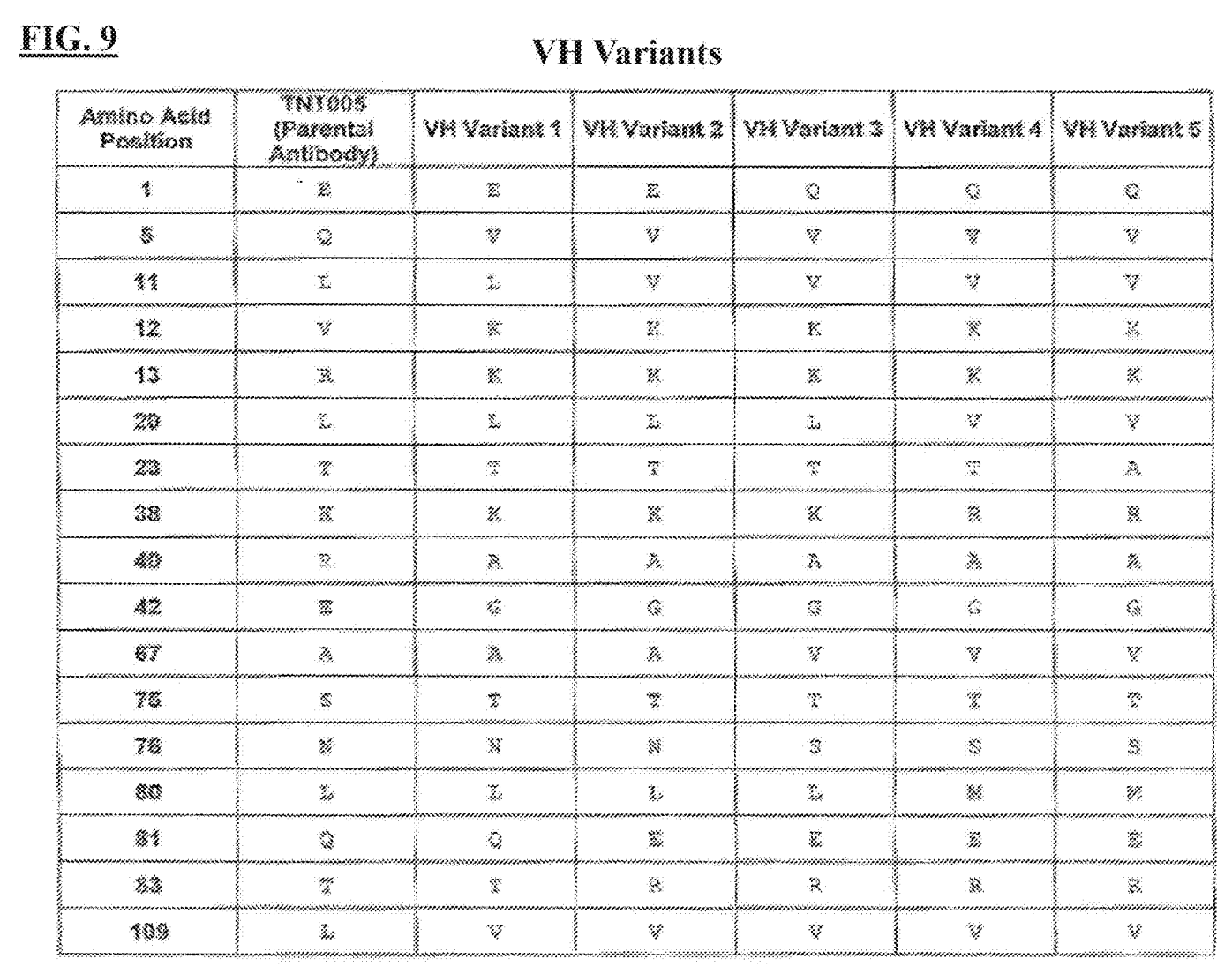

Humanized variants of anti-aC1s were generated. Amino acid sequences of the heavy chain VH domains of humanized variants 1-5; nucleotide sequences encoding the heavy chain VH domain of the humanized variants are also provided. Amino acid sequences of the light chain VL domain of the humanized variants 1, 2, and 5, and nucleotide sequences encoding the light chain VL domain of the humanized variants, are shown in FIGS. 6-8. Amino acid differences relative to the amino acid sequence of murine anti-aC1s (VL SEQ ID NO: 7; VH SEQ ID NO: 8) are summarized in FIGS. 9 and 10.

Single letter amino acid codes are as follows (with 3-letter amino acid codes in parentheses):
  G—Glycine (Gly)
  P—Proline (Pro)
  A—Alanine (Ala)
  V—Valine (Val)
  L—Leucine (Leu)
  I—Isoleucine (Ile)
  M—Methionine (Met)
  C—Cysteine (Cys)
  F—Phenylalanine (Phe)
  Y—Tyrosine (Tyr)
  W—Tryptophan (Trp)
  H—Histidine (His)
  K—Lysine (Lys)
  R—Arginine (Arg)
  Q—Glutamine (Gln)
  N—Asparagine (Asn)
  E—Glutamic Acid (Glu)
  D—Aspartic Acid (Asp)
  S—Serine (Ser)
  T—Threonine (Thr)

Example 2: Characterization of Humanized Anti-aC1s Variants

Binding characteristics of humanized anti-aC1s variants are provided in Tables 4 and 5 (FIG. 11 and FIG. 12, respectively). The relative binding affinities for various humanized anti-aC1s variants to activated C1s are provided in Table 4 (first data column), which is presented in FIG. 11.

All 15 combinations (VH variant 1+Vk variant 1; VH variant 1+Vk variant 2; VH variant 1+Vk variant 5; VH variant 2+Vk variant 1; VH variant 2+Vk variant 2; VH variant 2+Vk variant 5; VH variant 3+Vk variant 1; VH variant 3+Vk variant 2; VH variant 3+Vk variant 5; VH variant 4+Vk variant 1; VH variant 4+Vk variant 2; VH variant 4+Vk variant 5; VH variant 5+Vk variant 1; VH variant 5+Vk variant 2; VH variant 5+Vk variant 5) were produced. Each humanized variant was tested for the ability to compete with biotinylated murine anti-aC1s for binding to active C1s. The data are shown in FIG. 11, second data column.

Each humanized variant was tested in a commercially available assay that measures complement classical pathway (CP) activation. The results are shown in FIG. 11, third data column. The data show that all 15 humanized variants inhibit CP activation with an $IC_{50}$ similar to that of murine anti-aC1s.

Kinetic characterization of binding affinity was carried out on 8 of the humanized anti-aC1s variants. The data are depicted in Table 5, which is presented in FIG. 12.

Example 3: In Vivo Studies in Cynomolgus Monkeys

To assess the pharmacokinetic (PK) and pharmacodynamic (PD) properties of humanized anti-aC1s, single-dose studies of humanized anti-aC1s were performed in cynomolgus monkeys (*Macaca fascicularis*). Additionally, to compare the bioavailability of humanized anti-aC1s by various routes of administration, the humanized anti-aC1s variant was administered either by intravenous (IV) or subcutaneous (SC) injection. Following humanized anti-aC1s dosing, plasma and serum samples were taken at designated time points to determine circulating concentrations of humanized anti-aC1s; and to assess inhibition of the classical complement pathway (CP) by humanized anti-aC1s. Plasma and serum levels of humanized anti-aC1s over time provide PK data; inhibition of the CP over time provides PD data.

All study animals were female, between 2.4-3.9 kg body weight, and were between the ages of 3-5 years old. Additionally, all animals were naïve to pharmaceutical dosing.

Whole blood was collected in $K_2EDTA$ tubes and serum separator tubes for plasma and serum processing, respectively, and immediately stored at −15° C. to −25° C.

Figure 13:
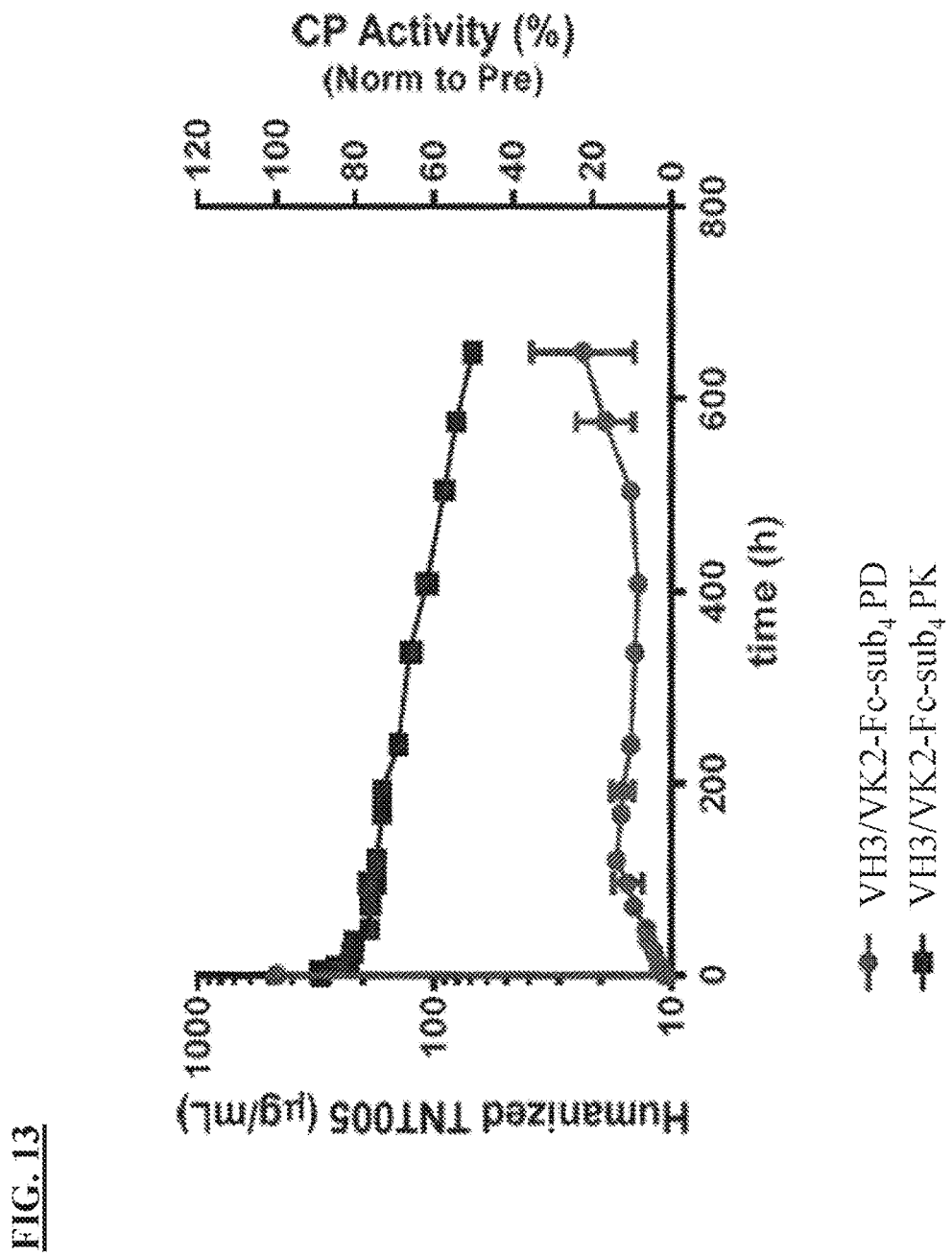
FIG. 13 depicts a pharmacokinetic (PK) profile and a pharmacodynamic (PD) profile for a humanized anti-aC1s variant (VH3/VK2-Fc-sub$_4$; also known as TNT020) delivered intravenously at 10 mg/kg to cynomolgus monkeys. The data show % complement pathway (CP) activity (normalized to pre-administration level), and serum concentration (g/mL) of administered antibody, at times up to 650 hours post-administration.
Figure 14:
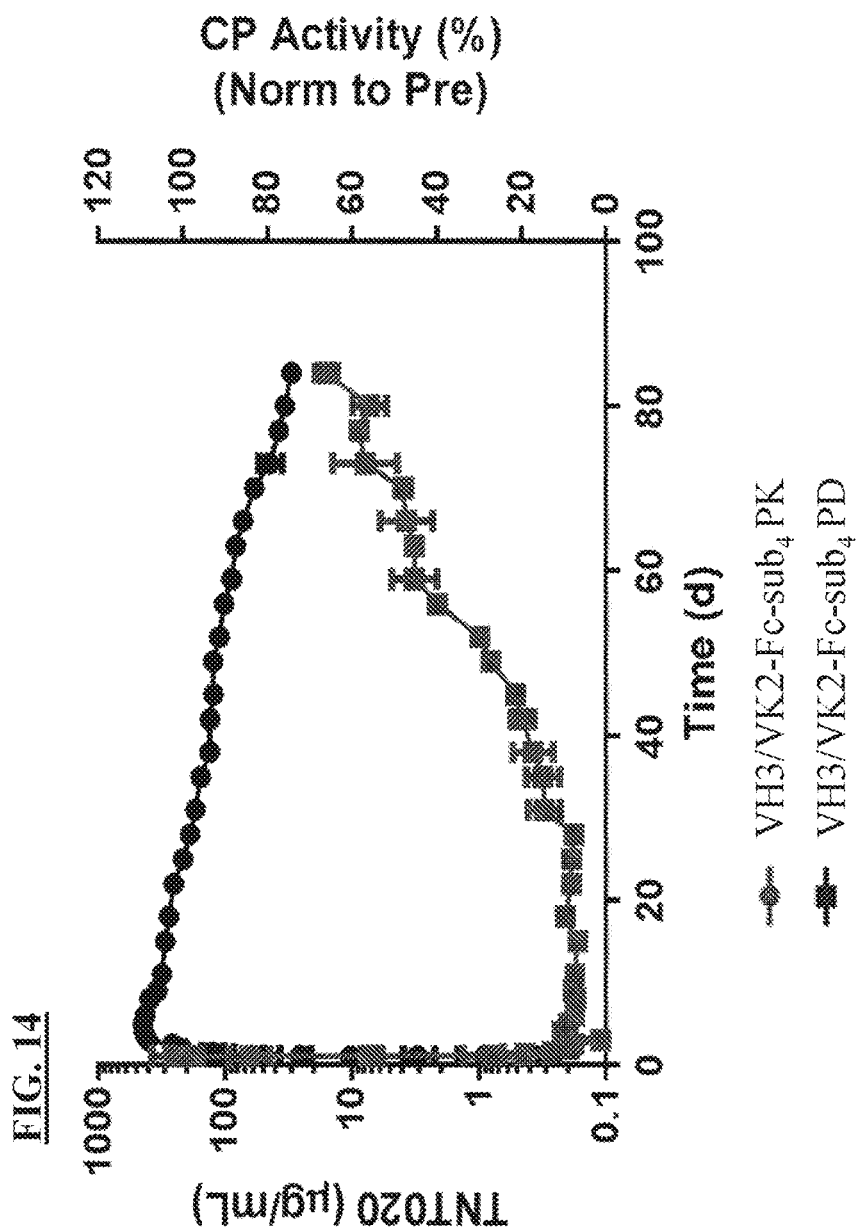
FIG. 14 depicts a PK profile and a PD profile for VH3/VK2-Fc-sub$_4$ delivered subcutaneously at 20 mg/kg to cynomolgus monkeys. The data show % CP activity (normalized to pre-administration level), and serum concentration (g/mL) of administered antibody, at times up to 55 days post-administration. The pharmacokinetic (circles) and pharmacodynamic (squares) profiles are overlaid. CP=complement pathway.

To assess the pharmacokinetic profile of the humanized anti-aC1s variant VH3/VK2-Fc-sub$_4$, plasma samples taken at the time points depicted in FIG. 13 and FIG. 14 were diluted and run in an ELISA to quantify VH3/VK2-Fc-sub$_4$ plasma concentrations. Briefly, diluted plasma samples were added to a 96-well plate pre-coated with activated C1s. Following plasma sample incubation and subsequent washing, a horseradish peroxidase-conjugated detection antibody specific for human IgG was added to detect C1s-bound VH3/VK2-Fc-sub$_4$. Finally, 3,3', 5,5'-tetramethylbenzidine (TMB) substrate was added to initiate a colorimetric reaction that was read on a spectrophotometer. By interpolating from a standard curve of VH3/VK2-Fc-sub$_4$ run in parallel with the plasma samples, VH3/VK2-Fc-sub$_4$ plasma concentrations were determined for all samples.

The pharmacodynamic effects of VH3/VK2-Fc-sub$_4$ were assessed using the WIESLAB® classical complement pathway kit. The WIESLAB® kit is commercially available, and involves use of an enzyme-linked immunosorbent assay (ELISA) that is designed to evaluate the strength of classical complement pathway activity in serum samples by activating the classical pathway of the sample ex vivo and measuring the ex vivo generation of the final split product of the pathway, C5b-9. Samples were assayed according to the manufacturer's instructions. Briefly, serum samples from the monkeys, collected at the time points indicated in FIG. 14 and FIG. 15, were diluted and added to the wells of the provided 96-well plate. Following incubation, a detection antibody specific for the final split product of the classical pathway, C5b-9, was added and the colorimetric reaction measured on a spectrophotometer. All samples for an individual monkey were compared and normalized to the pre-dose sample of the same monkey (pre-dose=100% activity).

FIG. 13 depicts PD and PK data from 3 animals dosed with VH3/VK2-Fc-sub$_4$, administered intravenously at 10 mg/kg. As shown in FIG. 13, the serum concentration of VH3/VK2-Fc-sub$_4$ was between 70 μg/mL and 300 μg/mL over a period of time of up to 650 hours (27 days). During this same time period, CP activity was inhibited 80% to 99%.

FIG. 14 depicts PD and PK data from 3 animals dosed with VH3/VK2-Fc-sub$_4$, administered subcutaneously at 20 mg/kg. As shown in FIG. 14, the serum concentration of VH3/VK2-Fc-sub$_4$ was between about 50 μg/mL and about 450 μg/mL over a period of time of up to 85 days. During the same time period, CP activity, as measured using the WEISLAB® kit was inhibited 60% to 99%. Further, a single 20 mg/kg subcutaneous dose of VH3/VK2-Fc-sub$_4$ inhibited the complement pathway by greater than 90% for 28 days (FIG. 19).

Example 4: Characterization of an Anti-C1s Antibody Comprising a Modified Fc Region The humanized anti-aC1s variant, VH3/VK2, comprised a human IgG4, with S241P and L248E substitutions. To enhance half-life and subcutaneous availability, the Fc region of VH3/VK2 was modified to include M428L and N434S substitutions. The resulting antibody, referred to as VH3/VK2-Fc-sub$_4$, was found to specifically bind active C1s with a dissociation constant of $1.53 \times 10^{-9}$.

Figure 17A:
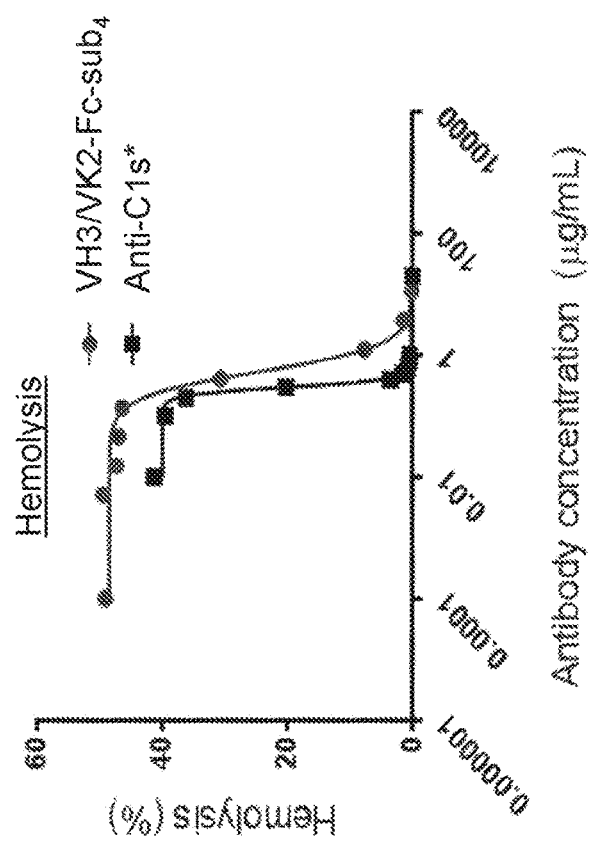
FIGS. 17A-17B are graphical representations illustrating the serum complement pathway (CP) activity (FIG. 17A) and hemolysis (FIG. 17B) in vitro, following exposure to varying concentrations of an anti-C1s antibody that targets both active and inactive C1s (squares) or VH3/VK2-Fc-sub$_4$ (circles).
Figure 17B:
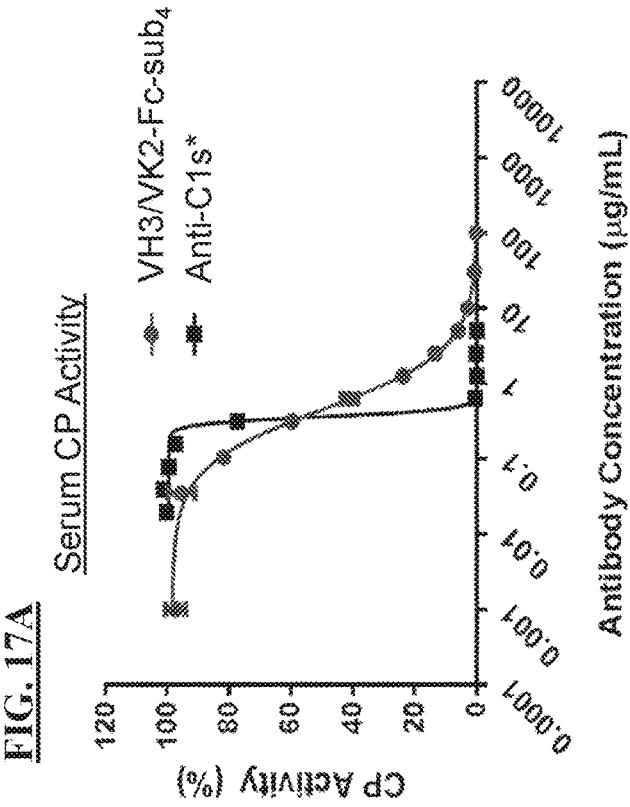

VH3/VK2-Fc-sub$_4$ inhibited the complement pathway in vitro to a similar extent as a general anti-C1s antibody, previously described as VH4/VK2 in U.S. Pat. No. 8,945,562. In an in vitro classical complement pathway serum activity assay, VH3/VK2-Fc-sub$_4$ (circles) displayed a similar ED$_{50}$ as anti-C1s (squares), though the inhibition of classical complement pathway activity by VH3/VK2-Fc-sub$_4$ was more gradual than the inhibition of complement activity by anti-C1s (FIG. 17A). In addition, VH3/VK2-Fc-sub$_4$ displayed similar levels of hemolysis as the general anti-C1s antibody (FIG. 17B).

effects were also observed in cynomolgus monkeys administered a single subcutaneous dose of 20 mg/kg VH3/VK2-Fc-sub$_4$ (see FIG. 14).

Example 5: Pharmacokinetic Study of Anti-C1s Antibody Following Intravenous and Subcutaneous Administrations in Cynomolgus Monkeys The objective of this investigational study is to evaluate the pharmacokinetics of VH3/VK2-Fc-sub$_4$, following a single intravenous (IV) bolus injection, single IV bolus injection followed by once weekly subcutaneous (SC) injections, or repeat SC injections in female cynomolgus monkeys.

Study Design

Animals will be assigned to groups and treated as indicated in Table 2. Animals will either be dosed via intravenous (IV) bolus injection in a peripheral vein using primed butterfly infusion lines or by subcutaneous (SC) bolus injection in the interscapular region of the back. If irritation is noted at the injection site, the lower thoracic region can be used for subsequent SC injections to avoid further irritation. The frequency of dosage is consistent with the anticipated pharmacokinetics of the test article. The regimen for treatment selected for this study is anticipated to identify achievable concentrations in peripheral blood and associated pharmacological activity.

TABLE 2

Group assignments

| Group | Test Material | Dosing Days/ Frequency | Route | Dose Level (mg/kg) | Concentration (mg/mL) | Volume$^a$ (mL/kg) | Number of Animals Females |
|---|---|---|---|---|---|---|---|
| 1 | CA/V | 1 | IV | 0 | 0 | 4 | 3 |
|   |   | 8, 15, 22, 29, 36, and 43 | SC | 0 | 0 | 2 |   |
| 2 | VH3/VK2-Fc-sub$_4$ | 1 | IV | 45 | 15 | 3 | 3 |
| 3 | VH3/VK2-Fc-sub$_4$ | 1 | IV | 10 | 2.5 | 4 | 3 |
|   |   | 8, 15, 22, 29, 36, and 43 | SC | 2 | 1 | 2 |   |
| 4 | VH3/VK2-Fc-sub$_4$ | 1 and 29 | SC | 10 | 5 | 2 | 3 |

$^a$Total dose volume (mL) will be calculated based on the most recent body weight.
CA/V: control article/vehicle; IV: intravenous bolus injection; SC: subcutaneous bolus injection.

Figure 18B:
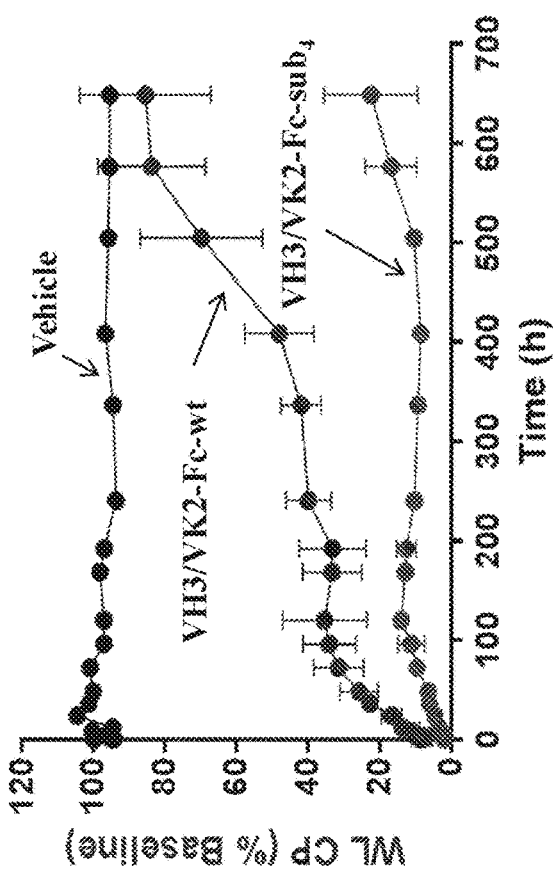
FIGS. 18A-18B are graphical representations illustrating the pharmacokinetic (FIG. 18A) and pharmacodynamic (FIG. 181B) profiles for an anti-aC1s antibody variant (VH3/VK2 having a wild-type IgG4 Fc) and VH3/VK2-Fc-sub$_4$ (having a heavy chain sequence comprising SEQ ID NO: 28). A negative "vehicle" control is also shown in FIG. 18B.
Figure 18A:
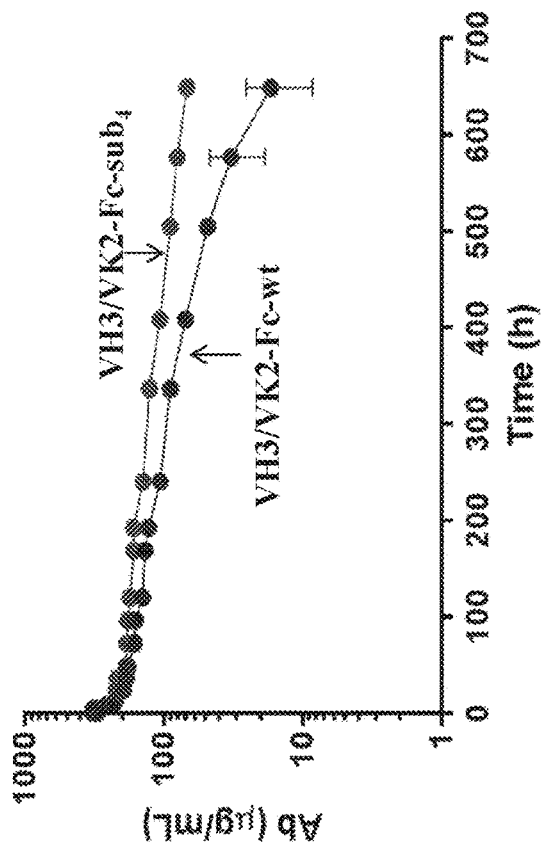

It was hypothesized that if FcRn binding is involved in the recycling of VH3/VK2 (VH3/VK2-Fc-sub$_4$ without enhanced FcRn binding), then VH3/VK2-Fc-sub$_4$ should have a longer half-life and therefore a prolonged pharmacodynamic effect compared to VH3/VK2. Cynomolgus monkeys were administered a single intravenous dose of 10 mg/kg of VH3/VK2 or VH3/VK2-Fc-sub$_4$, and blood was drawn periodically. Through 650 hours post-administration, animals administered VH3/VK2-Fc-sub$_4$ had consistently higher levels of the antibody in their blood than animals administered VH3/VK2 (FIG. 18A). In addition, VH3/VK2-Fc-sub$_4$ had a prolonged pharmacodynamic effect than VH3/VK2. A single dose of 10 mg/kg of VH3/VK2-Fc-sub$_4$ inhibited complement pathway activity by more than 70% through 650 hours, whereas the same dose of VH3/VK2 showed a gradual decrease in inhibition, beginning almost immediately, and nearly reaching the level of the vehicle control by 650 hours post administration (FIG. 18B). These Clinical Observations Clinical observations will be performed once daily, beginning on the second day of acclimation for each animal in the AM, prior to room cleaning. A mortality check will be conducted twice daily to assess general animal health and wellness.

Additional clinical observations can be performed, as necessary. If clinical observations for an animal demonstrate declining animal condition, a veterinary evaluation will be performed and the Study Director notified.

Blood will be collected from a peripheral vein of restrained, conscious animals. For the first 24 hours post dose, blood will not be collected from the vein (or limb) that was used for IV dose administration. Blood will be collected via a single draw and then divided appropriately.

In the event of an unscheduled necropsy, venous blood samples will be collected from conscious moribund animals prior to anesthesia, if possible.

Blood samples will be collected at the following timepoints and stored on wet ice prior to processing:

Groups 1 and 3: Days 1 (15 min, 30 min, 1 hr, 2 hrs, and 4 hrs posdose), 2 (24 hrs postdose), 5, 8 (predose, 30 min, 1 hr, 2 hrs, and 4 hrs postdose), 9, 10, 11, 12, 13, 14, 15 (predose), 18, 22 (predose), 25, 29 (predose), 32, 36 (predose), 39, 43 (predose), 46, 50, 53, and 57;

Group 2: Days 1 (15 min, 30 min, 1 hr, 2 hrs, and 4 hrs postdose), 2 (24 hrs postdose), 3 (48 hrs postdose), 5 (96 hrs postdose), 8 (168 hrs postdose), 15, 22, 25, 29, 32, 36, 39, 43, 46, 50, 53, and 57; and Group 4: Days 1 (30 min, 1 hr, 2 hrs, and 4 hrs postdose), 2 (24 hrs postdose), 3, 4, 5, 6, 11, 15, 18, 22, 25, 29 (predose, 30 min, 1 hr, 2 hrs, and 4 hrs postdose), 30, 31, 32, 33, 34, 39, 43, 46, 50, 53, and 57.

While the present disclosure has been described with reference to the specific embodiments thereof, it should be understood by those skilled in the art that various changes can be made and equivalents can be substituted without departing from the true spirit and scope of the disclosure. In addition, many modifications can be made to adapt a particular situation, material, composition of matter, process, process step or steps, to the objective, spirit and scope of the present disclosure. All such modifications are intended to be within the scope of the claims appended hereto.

What is claimed is:

1. A method of inhibiting a complement pathway in a subject having chronic inflammatory demyelinating polyneuropathy (CIDP), comprising administering to the subject a pharmaceutically effective amount of an antibody that specifically binds activated C1s and comprises:
   a light chain variable (VL) region comprising the amino acid sequence of SEQ ID NO: 22;
   a light chain constant region;
   a heavy chain variable (VH) region comprising the amino acid sequence of SEQ ID NO: 14; and
   a heavy chain IgG4 constant region comprising a proline (pro), a glutamic acid (glu), a leucine (leu), and a serine (ser) substitution at amino acid residues 108, 115, 308, and 314, respectively, relative to the IgG4 constant region sequence of SEQ ID NO: 52.

2. The method of claim 1, wherein the heavy chain of the antibody comprises SEQ ID NO: 29.

3. The method of claim 1, wherein the light chain of the antibody comprises SEQ ID NO: 30.

4. The method of claim 1, wherein the heavy chain of the antibody comprises SEQ ID NO: 29 and the light chain of the antibody comprises SEQ ID NO: 30.

5. The method of claim 1, wherein the antibody is a bispecific antibody or a multispecific antibody.

6. The method of claim 1, wherein the antibody comprises two light chains and two heavy chains, and wherein (i) each light chain comprises a light chain variable (VL) region comprising the amino acid sequence of SEQ ID NO: 22, and a light chain constant region; and (ii) each heavy chain comprises a heavy chain variable (VH) region comprising the amino acid sequence of SEQ ID NO: 14, and a heavy chain IgG4 constant region comprising a proline (pro), a glutamic acid (glu), a leucine (leu), and a serine (ser) substitution at amino acid residues 108, 115, 308, and 314, respectively, relative to the IgG4 constant region sequence of SEQ ID NO: 52.

7. The method of claim 1, wherein the antibody comprises two heavy chains comprising the amino acid sequence of SEQ ID NO: 29 and two light chains comprising the amino acid sequence of SEQ ID NO: 30.

8. A method of treating chronic inflammatory demyelinating polyneuropathy (CIDP) in a subject in need thereof, comprising administering to the subject a pharmaceutically effective amount of an antibody that specifically binds activated C1s and comprises:
   a light chain variable (VL) region comprising the amino acid sequence of SEQ ID NO: 22;
   a light chain constant region;
   a heavy chain variable (VH) region comprising the amino acid sequence of SEQ ID NO: 14; and
   a heavy chain IgG4 constant region comprising a proline (pro), a glutamic acid (glu), a leucine (leu), and a serine (ser) substitution at amino acid residues 108, 115, 308, and 314, respectively, relative to the IgG4 constant region sequence of SEQ ID NO: 52.

9. The method of claim 8, wherein the heavy chain of the antibody comprises SEQ ID NO: 29.

10. The method of claim 8, wherein the light chain of the antibody comprises SEQ ID NO: 30.

11. The method of claim 8, wherein the heavy chain of the antibody comprises SEQ ID NO: 29 and the light chain comprises SEQ ID NO: 30.

12. The method of claim 8, wherein the antibody is a bispecific antibody or a multispecific antibody.

13. The method of claim 8, wherein the antibody comprises two light chains and two heavy chains, and wherein (i) each light chain comprises a light chain variable (VL) region comprising the amino acid sequence of SEQ ID NO:22, and a light chain constant region; and (ii) each heavy chain comprises a heavy chain variable (VH) region comprising the amino acid sequence of SEQ ID NO: 14, and a heavy chain IgG4 constant region comprising a proline (pro), a glutamic acid (glu), a leucine (leu), and a serine (ser) substitution at amino acid residues 108, 115, 308, and 314, respectively, relative to the IgG4 constant region sequence of SEQ ID NO: 52.

14. The method of claim 8, wherein the antibody comprises two heavy chains comprising the amino acid sequence of SEQ ID NO: 29 and two light chains comprising the amino sequence of SEQ ID NO: 30.

15. The method of claim 1, wherein the heavy chain IgG4 constant region comprises the sequence of SEQ ID NO: 28.

16. The method of claim 8, wherein the heavy chain IgG4 constant region comprises the sequence of SEQ ID NO: 28.

* * * * *

```
                            SEQUENCE LISTING

Sequence total quantity: 54
SEQ ID NO: 1            moltype = AA  length = 15
FEATURE                 Location/Qualifiers
REGION                  1..15
                        note = VL CDR1
source                  1..15
                        mol_type = protein
                        organism = synthetic construct
SEQUENCE: 1
KASQSVDYDG DSYMN                                                          15

SEQ ID NO: 2            moltype = AA  length = 7
FEATURE                 Location/Qualifiers
REGION                  1..7
                        note = VL CDR2
source                  1..7
                        mol_type = protein
                        organism = synthetic construct
SEQUENCE: 2
DASNLES                                                                    7

SEQ ID NO: 3            moltype = AA  length = 9
FEATURE                 Location/Qualifiers
REGION                  1..9
                        note = VL CDR3
source                  1..9
                        mol_type = protein
                        organism = synthetic construct
SEQUENCE: 3
QQSNEDPWT                                                                  9

SEQ ID NO: 4            moltype = AA  length = 5
FEATURE                 Location/Qualifiers
REGION                  1..5
                        note = VH CDR1
source                  1..5
                        mol_type = protein
                        organism = synthetic construct
SEQUENCE: 4
DDYIH                                                                      5

SEQ ID NO: 5            moltype = AA  length = 17
FEATURE                 Location/Qualifiers
REGION                  1..17
                        note = VH CDR2
source                  1..17
                        mol_type = protein
                        organism = synthetic construct
SEQUENCE: 5
RIDPADGHTK YAPKFQV                                                        17

SEQ ID NO: 6            moltype = AA  length = 10
FEATURE                 Location/Qualifiers
REGION                  1..10
                        note = VH CDR3
source                  1..10
                        mol_type = protein
                        organism = synthetic construct
SEQUENCE: 6
YGYGREVFDY                                                                10

SEQ ID NO: 7            moltype = AA  length = 111
```

```
FEATURE                 Location/Qualifiers
REGION                  1..111
                        note = Parental Murine anti-C1s VL Variable Light
source                  1..111
                        mol_type = protein
                        organism = synthetic construct
SEQUENCE: 7
DIVLTQSPAS LAVSLGQRAT ISCKASQSVD YDGDSYMNWY QQKTGQPPKI LIYDASNLES    60
GIPARFSGSG SGTDFTLNIH PVEEEDAAIY YCQQSNEDPW TFGGGTKLEI K            111

SEQ ID NO: 8            moltype = AA  length = 119
FEATURE                 Location/Qualifiers
REGION                  1..119
                        note = VH CDR of an anti-C1s antibody
source                  1..119
                        mol_type = protein
                        organism = synthetic construct
SEQUENCE: 8
EVQLQQSGAE LVRPGASVKL SCTASGFNIK DDYIHWVKQR PEQGLEWIGR IDPADGHTKY    60
APKFQVKATI TADTSSNTAY LQLSSLTSED TAVYYCARYG YGREVFDYWG QGTTLTVSS    119

SEQ ID NO: 9            moltype = AA  length = 673
FEATURE                 Location/Qualifiers
REGION                  1..673
                        note = Human C1s
source                  1..673
                        mol_type = protein
                        organism = synthetic construct
SEQUENCE: 9
EPTMYGEILS PNYPQAYPSE VEKSWDIEVP EGYGIHLYFT HLDIELSENC AYDSVQIISG    60
DTEEGRLCGQ RSSNNPHSPI VEEFQVPYNK LQVIFKSDFS NEERFTGFAA YYVATDINEC   120
TDFVDVPCSH FCNNFIGGYF CSCPPEYFLH DDMKNCGVNC SGDVFTALIG EIASPNYPKP   180
YPENSRCEYQ IRLEKGFQVV VTLRREDFDV EAADSAGNCL DSLVFVAGDR QFGPYCGHGF   240
PGPLNIETKS NALDIIFQTD LTGQKKGWKL RYHGDPMPCP KEDTPNSVWE PAKAKYVFRD   300
VVQITCLDGF EVVEGRVGAT SFYSTCQSNG KWSNSKLKCQ PVDCGIPESI ENGKVEDPES   360
TLFGSVIRYT CEEPYYYMEN GGGGEYHCAG NGSWVNEVLG PELPKCVPVC GVPREPFEEK   420
QRIIGGSDAD IKNFPWQVFF DNPWAGGALI NEYWVLTAAH VVEGNREPTM YVGSTSVQTS   480
RLAKSKMLTP EHVFIHPGWK LLEVPEGRTN FDNDIALVRL KDPVKMGPTV SPICLPGTSS   540
DYNLMDGDLG LISGWGRTEK RDRAVRLKAA RLPVAPLRKC KEVKVEKPTA DAEAYVFTPN   600
MICAGGEKGM DSCKGDSGGA FAVQDPNDKT KFYAAGLVSW GPQCGTYGLY TRVKNYVDWI   660
MKTMQENSTP RED                                                     673

SEQ ID NO: 10           moltype = AA  length = 119
FEATURE                 Location/Qualifiers
REGION                  1..119
                        note = VH1 Variant
source                  1..119
                        mol_type = protein
                        organism = synthetic construct
SEQUENCE: 10
EVQLVQSGAE LKKPGASVKL SCTASGFNIK DDYIHWVKQA PGQGLEWIGR IDPADGHTKY    60
APKFQVKATI TADTSTNTAY LQLSSLTSED TAVYYCARYG YGREVFDYWG QGTTVTVSS   119

SEQ ID NO: 11           moltype = DNA  length = 357
FEATURE                 Location/Qualifiers
misc_feature            1..357
                        note = VH variant 1
source                  1..357
                        mol_type = other DNA
                        organism = synthetic construct
SEQUENCE: 11
gaggttcagc tggtgcagtc tggggctgag cttaagaagc caggggcctc agtcaagttg    60
tcctgcacag cttctggctt taacattaaa gacgactata cactgggt gaagcaggcc    120
cctggacagg gcctggagtg gattggaagg attgatcctg cggatggtca tactaaatat   180
gccccgaagt tccaagtcaa ggccactata actgcagaca catccaccaa cacagcctac   240
ctgcagctca gcagcctgac atctgaggac actgccgtct attactgtgc tagatatggt   300
tacgggaggg aggtctttga ctactggggc caaggcacca ctgtcacagt ctcctca      357

SEQ ID NO: 12           moltype = AA  length = 119
FEATURE                 Location/Qualifiers
REGION                  1..119
                        note = VH2 variant
source                  1..119
                        mol_type = protein
                        organism = synthetic construct
SEQUENCE: 12
EVQLVQSGAE VKKPGASVKL SCTASGFNIK DDYIHWVKQA PGQGLEWIGR IDPADGHTKY    60
APKFQVKATI TADTSTNTAY LELSSLRSED TAVYYCARYG YGREVFDYWG QGTTVTVSS   119
```

| SEQ ID NO: 13 | moltype = DNA  length = 357 |
| --- | --- |
| FEATURE | Location/Qualifiers |
| misc_feature | 1..357 |
| | note = VH variant 2 |
| source | 1..357 |
| | mol_type = other DNA |
| | organism = synthetic construct |

SEQUENCE: 13

```
gaggttcagc tggtgcagtc tggggctgag gtgaagaagc caggggcctc agtcaagttg   60
tcctgcacag cttctggctt taacattaaa gacgactata tacactgggt gaagcaggcc  120
cctggacagg gcctggagtg gattggaagg attgatcctg cggatggtca tactaaatat  180
gccccgaagt tccaagtcaa ggccactata actgcagaca catccaccaa cacagcctac  240
ctggagctca gcagcctgag atctgaggac actgccgtct attactgtgc tagatatggt  300
tacgggaggg aggtctttga ctactggggc caaggcacca ctgtcacagt ctcctca     357
```

| SEQ ID NO: 14 | moltype = AA  length = 119 |
| --- | --- |
| FEATURE | Location/Qualifiers |
| REGION | 1..119 |
| | note = VH3 variant |
| source | 1..119 |
| | mol_type = protein |
| | organism = synthetic construct |

SEQUENCE: 14

```
QVQLVQSGAE VKKPGASVKL SCTASGFNIK DDYIHWVRQA PGQGLEWIGR IDPADGHTKY   60
APKFQVKVTI TADTSTSTAY LELSSLRSED TAVYYCARYG YGREVFDYWG QGTTVTVSS  119
```

| SEQ ID NO: 15 | moltype = DNA  length = 357 |
| --- | --- |
| FEATURE | Location/Qualifiers |
| misc_feature | 1..357 |
| | note = VH variant 3 |
| source | 1..357 |
| | mol_type = other DNA |
| | organism = synthetic construct |

SEQUENCE: 15

```
caggttcagc tggtgcagtc tggggctgag gtgaagaagc caggggcctc agtcaagttg   60
tcctgcacag cttctggctt taacattaaa gacgactata tacactgggt gaagcaggcc  120
cctggacagg gcctggagtg gattggaagg attgatcctg cggatggtca tactaaatat  180
gccccgaagt tccaagtcaa agtcactata actgcagaca catccaccag cacagcctac  240
ctggagctca gcagcctgag atctgaggac actgccgtct attactgtgc tagatatggt  300
tacgggaggg aggtctttga ctactggggc caaggcacca ctgtcacagt ctcctca     357
```

| SEQ ID NO: 16 | moltype = AA  length = 119 |
| --- | --- |
| FEATURE | Location/Qualifiers |
| REGION | 1..119 |
| | note = VH4 variant |
| source | 1..119 |
| | mol_type = protein |
| | organism = synthetic construct |

SEQUENCE: 16

```
QVQLVQSGAE VKKPGASVKV SCTASGFNIK DDYIHWVRQA PGQGLEWIGR IDPADGHTKY   60
APKFQVKVTI TADTSTSTAY MELSSLRSED TAVYYCARYG YGREVFDYWG QGTTVTVSS  119
```

| SEQ ID NO: 17 | moltype = DNA  length = 357 |
| --- | --- |
| FEATURE | Location/Qualifiers |
| misc_feature | 1..357 |
| | note = VH variant 4 |
| source | 1..357 |
| | mol_type = other DNA |
| | organism = synthetic construct |

SEQUENCE: 17

```
caggttcagc tggtgcagtc tggggctgag gtgaagaagc caggggcctc agtcaaggtc   60
tcctgcacag cttctggctt taacattaaa gacgactata tacactgggt gcgccaggcc  120
cctggacagg gcctggagtg gattggaagg attgatcctg cggatggtca tactaaatat  180
gccccgaagt tccaagtcaa agtcactata actgcagaca catccaccag cacagcctac  240
atggagctca gcagcctgag atctgaggac actgccgtct attactgtgc tagatatggt  300
tacgggaggg aggtctttga ctactggggc caaggcacca ctgtcacagt ctcctca     357
```

| SEQ ID NO: 18 | moltype = AA  length = 119 |
| --- | --- |
| FEATURE | Location/Qualifiers |
| REGION | 1..119 |
| | note = VH5 variant |
| source | 1..119 |
| | mol_type = protein |
| | organism = synthetic construct |

SEQUENCE: 18

```
QVQLVQSGAE VKKPGASVKV SCAASGFNIK DDYIHWVRQA PGQGLEWIGR IDPADGHTKY   60
APKFQVKVTI TADTSTSTAY MELSSLRSED TAVYYCARYG YGREVFDYWG QGTTVTVSS  119
```

| SEQ ID NO: 19 | moltype = DNA  length = 357 |
| --- | --- |

| FEATURE | Location/Qualifiers |
|---|---|
| misc_feature | 1..357 |
| | note = VH variant 5 |
| source | 1..357 |
| | mol_type = other DNA |
| | organism = synthetic construct |

SEQUENCE: 19
```
caggttcagc tggtgcagtc tggggctgag gtgaagaagc caggggcctc agtcaaggtc    60
tcctgcgcag cttctggctt taacattaaa gacgactata tacactgggt gcgccaggtc   120
cctggacagg gcctggagtg gattggaagg attgatcctg cggatggtca tactaaatat   180
gccccgaagt tccaagtcaa agtcactata actgcagaca catccaccag cacagcctac   240
atggagctca gcagcctgag atctgaggac actgccgtct attactgtgc tagatatggt   300
tacgggaggg aggtctttga ctactggggc caaggcacca ctgtcacagt ctcctca      357
```

| SEQ ID NO: 20 | moltype = AA  length = 111 |
|---|---|
| FEATURE | Location/Qualifiers |
| REGION | 1..111 |
| | note = Vkappa1 variant Variable Light |
| source | 1..111 |
| | mol_type = protein |
| | organism = synthetic construct |

SEQUENCE: 20
```
DIVLTQSPDS LAVSLGERAT ISCKASQSVD YDGDSYMNWY QQKTGQPPKI LIYDASNLES    60
GIPARFSGSG SGTDFTLTIS SLEEEDFAIY YCQQSNEDPW TFGGGTKVEI K            111
```

| SEQ ID NO: 21 | moltype = DNA  length = 333 |
|---|---|
| FEATURE | Location/Qualifiers |
| misc_feature | 1..333 |
| | note = Vkappa variant 1 |
| source | 1..333 |
| | mol_type = other DNA |
| | organism = synthetic construct |

SEQUENCE: 21
```
gacattgtgc tgacccaatc tccagactct ttggctgtgt ctctcgggga gagggccacc    60
atctcctgca aggccagcca aagtgttgat tatgatgtgt atagttatat gaactggtac   120
caacaaaaaa caggacagcc acccaaaatc ctcatttatg atgcatccaa tttggaatct   180
ggcatcccag ccaggtttag tggcagtggg tctgggacag acttcaccct caccatcagc   240
agcctggagg aggaggattt tgcaatctat tactgtcagc aaagtaatga agacccgtgg   300
acgttcggtg gaggcaccaa ggtggaaatc aaa                                333
```

| SEQ ID NO: 22 | moltype = AA  length = 111 |
|---|---|
| FEATURE | Location/Qualifiers |
| REGION | 1..111 |
| | note = Vkappa2 variant Variable Light |
| source | 1..111 |
| | mol_type = protein |
| | organism = synthetic construct |

SEQUENCE: 22
```
DIVLTQSPDS LAVSLGERAT ISCKASQSVD YDGDSYMNWY QQKPGQPPKI LIYDASNLES    60
GIPARFSGSG SGTDFTLTIS SLEPEDFAIY YCQQSNEDPW TFGGGTKVEI K            111
```

| SEQ ID NO: 23 | moltype = DNA  length = 333 |
|---|---|
| FEATURE | Location/Qualifiers |
| misc_feature | 1..333 |
| | note = Vkappa variant 2 |
| source | 1..333 |
| | mol_type = other DNA |
| | organism = synthetic construct |

SEQUENCE: 23
```
gacattgtgc tgacccaatc tccagactct ttggctgtgt ctctcgggga gagggccacc    60
atctcctgca aggccagcca aagtgttgat tatgatggtg atagttatat gaactggtac   120
caacaaaaac caggacagcc acccaaaatc ctcatttatg atgcatccaa tttggaatct   180
ggcatcccag ccaggtttag tggcagtggg tctgggacag acttcaccct caccatcagc   240
agcctggagc ctgaggattt tgcaatctat tactgtcagc aaagtaatga agacccgtgg   300
acgttcggtg gaggcaccaa ggtggaaatc aaa                                333
```

| SEQ ID NO: 24 | moltype = AA  length = 111 |
|---|---|
| FEATURE | Location/Qualifiers |
| REGION | 1..111 |
| | note = Vkappa5 variant Variable Light |
| source | 1..111 |
| | mol_type = protein |
| | organism = synthetic construct |

SEQUENCE: 24
```
DIVLTQSPDS LAVSLGERAT ISCKASQSVD YDGDSYMNWY QQKPGQPPKL LIYDASNLES    60
GIPARFSGSG SGTDFTLTIS SLEPEDFAVY YCQQSNEDPW TFGGGTKVEI K            111
```

| SEQ ID NO: 25 | moltype = DNA  length = 333 |
|---|---|
| FEATURE | Location/Qualifiers |

```
misc_feature            1..333
                        note = Vkappa variant 5
source                  1..333
                        mol_type = other DNA
                        organism = synthetic construct
SEQUENCE: 25
gacattgtgc tgacccaatc tccagactct ttggctgtgt ctctcgggga gagggccacc    60
atctcctgca aggccagcca aagtgttgat tatgatggtg atagttatat gaactggtac   120
caacaaaaac caggacagcc acccaaactc ctcatttatg atgcatccaa tttggaatct   180
ggcatcccag ccaggtttag tggcagtggg tctgggacag acttcaccct caccatcagc   240
agcctggagc ctgaggattt tgcagtctat tactgtcagc aaagtaatga gacccgtgg    300
acgttcggtg aggcaccaa ggtggaaatc aaa                                 333

SEQ ID NO: 26           moltype = AA  length = 119
FEATURE                 Location/Qualifiers
REGION                  1..119
                        note = VH region of anti-C1s antibody
VARIANT                 1
                        note = may be Gln or Glu
VARIANT                 5
                        note = may be Val or Gln
VARIANT                 11
                        note = may be Val or Leu
VARIANT                 20
                        note = may be Leu or Val
VARIANT                 23
                        note = may be Thr or Ala
VARIANT                 38
                        note = may be Lys or Arg
VARIANT                 68
                        note = may be Val or Ala
VARIANT                 77
                        note = may be Ser or Asn
VARIANT                 81
                        note = may be Leu or Met
VARIANT                 82
                        note = may be Glu or Gln
VARIANT                 87
                        note = may be Arg or Thr
source                  1..119
                        mol_type = protein
                        organism = synthetic construct
SEQUENCE: 26
XVQLXQSGAE XKKPGASVKX SCXASGFNIK DDYIHWVXQA PGQGLEWIGR IDPADGHTKY    60
APKFQVKXTI TADTSTXTAY XXLSSLXSED TAVYYCARYG YGREVFDYWG QGTTVTVSS    119

SEQ ID NO: 27           moltype = AA  length = 111
FEATURE                 Location/Qualifiers
REGION                  1..111
                        note = VL region of anti-C1s antibody
VARIANT                 44
                        note = may be Thr or Pro
VARIANT                 50
                        note = may be Ile or Leu
VARIANT                 84
                        note = may be Glu or Pro
VARIANT                 89
                        note = may be Ile or Val
source                  1..111
                        mol_type = protein
                        organism = synthetic construct
SEQUENCE: 27
DIVLTQSPDS LAVSLGERAT ISCKASQSVD YDGDSYMNWY QQKXGQPPKX LIYDASNLES    60
GIPARFSGSG SGTDFTLTIS SLEXEDFAXY YCQQSNEDPW TFGGGTKVEI K            111

SEQ ID NO: 28           moltype = AA  length = 327
FEATURE                 Location/Qualifiers
REGION                  1..327
                        note = Human IgG4 Constant Region (Fc) Variant 2
source                  1..327
                        mol_type = protein
                        organism = synthetic construct
SEQUENCE: 28
ASTKGPSVFP LAPCSRSTSE STAALGCLVK DYFPEPVTVS WNSGALTSGV HTFPAVLQSS    60
GLYSLSSVVT VPSSSLGTKT YTCNVDHKPS NTKVDKRVES KYGPPCPPCP APEFEGGPSV   120
FLFPPKPKDT LMISRTPEVT CVVVDVSQED PEVQFNWYVD GVEVHNAKTK PREEQFNSTY   180
RVVSVLTVLH QDWLNGKEYK CKVSNKGLPS SIEKTISKAK GQPREPQVYT LPPSQEEMTK   240
NQVSLTCLVK GFYPSDIAVE WESNGQPENN YKTTPPVLDS DGSFFLYSRL TVDKSRWQEG   300
NVFSCSVLHE ALHSHYTQKS LSLSLGK                                       327
```

```
SEQ ID NO: 29            moltype = AA  length = 446
FEATURE                  Location/Qualifiers
REGION                   1..446
                         note = VH3 Mature Heavy Chain
source                   1..446
                         mol_type = protein
                         organism = synthetic construct
SEQUENCE: 29
QVQLVQSGAE VKKPGASVKL SCTASGFNIK DDYIHWVKQA PGQGLEWIGR IDPADGHTKY    60
APKFQVKVTI TADTSTSTAY LELSSLRSED TAVYYCARYG YGREVFDYWG QTTVTVSSA    120
STKGPSVFPL APCSRSTSES TAALGCLVKD YFPEPVTVSW NSGALTSGVH TFPAVLQSSG   180
LYSLSSVVTV PSSSLGTKTY TCNVDHKPSN TKVDKRVESK YGPPCPPCPA PEFEGGPSVF   240
LFPPKPKDTL MISRTPEVTC VVVDVSQEDP EVQFNWYVDG VEVHNAKTKP REEQFNSTYR   300
VVSVLTVLHQ DWLNGKEYKC KVSNKGLPSS IEKTISKAKG QPREPQVYTL PPSQEEMTKN   360
QVSLTCLVKG FYPSDIAVEW ESNGQPENNY KTTPPVLDSD GSFFLYSRLT VDKSRWQEGN   420
VFSCSVLHEA LHSHYTQKSL SLSLGK                                       446

SEQ ID NO: 30            moltype = AA  length = 218
FEATURE                  Location/Qualifiers
REGION                   1..218
                         note = Vkappa2 variant Mature Light Chain
source                   1..218
                         mol_type = protein
                         organism = synthetic construct
SEQUENCE: 30
DIVLTQSPDS LAVSLGERAT ISCKASQSVD YDGDSYMNWY QQKPGQPPKI LIYDASNLES    60
GIPARFSGSG SGTDFTLTIS SLEPEDFAIY YCQQSNEDPW TFGGGTKVEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 31            moltype = AA  length = 465
FEATURE                  Location/Qualifiers
REGION                   1..465
                         note = synthetic amino acid sequence
source                   1..465
                         mol_type = protein
                         organism = synthetic construct
SEQUENCE: 31
MGWSLILLFL VAVATRVHSQ VQLVQSGAEV KKPGASVKLS CTASGFNIKD DYIHWVKQAP    60
GQGLEWIGRI DPADGHTKYA PKFQVKVTIT ADTSTSTAYL ELSSLRSEDT AVYYCARYGY   120
GREVFDYWGQ GTTVTVSSAS TKGPSVFPLA PCSRSTSEST AALGCLVKDY FPEPVTVSWN   180
SGALTSGVHT FPAVLQSSGL YSLSSVVTVP SSSLGTKTYT CNVDHKPSNT KVDKRVESKY   240
GPPCPPCPAP EFEGGPSVFL FPPKPKDTLM ISRTPEVTCV VVDVSQEDPE VQFNWYVDGV   300
EVHNAKTKPR EEQFNSTYRV VSVLTVLHQD WLNGKEYKCK VSNKGLPSSI EKTISKAKGQ   360
PREPQVYTLP PSQEEMTKNQ VSLTCLVKGF YPSDIAVEWE SNGQPENNYK TTPPVLDSDG   420
SFFLYSRLTV DKSRWQEGNV FSCSVLHEAL HSHYTQKSLS LSLGK                  465

SEQ ID NO: 32            moltype = AA  length = 238
FEATURE                  Location/Qualifiers
REGION                   1..238
                         note = synthetic amino acid sequence
source                   1..238
                         mol_type = protein
                         organism = synthetic construct
SEQUENCE: 32
MRVPAQLLGL LLLWLPGARC DIVLTQSPDS LAVSLGERAT ISCKASQSVD YDGDSYMNWY    60
QQKPGQPPKI LIYDASNLES GIPARFSGSG SGTDFTLTIS SLEPEDFAIY YCQQSNEDPW   120
TFGGGTKVEI KRTVAAPSVF IFPPSDEQLK SGTASVVCLL NNFYPREAKV QWKVDNALQS   180
GNSQESVTEQ DSKDSTYSLS STLTLSKADY EKHKVYACEV THQGLSSPVT KSFNRGEC     238

SEQ ID NO: 33            moltype = AA  length = 11
FEATURE                  Location/Qualifiers
REGION                   1..11
                         note = VL CDR1 (CDR-L1) of anti-C1s antibody
source                   1..11
                         mol_type = protein
                         organism = synthetic construct
SEQUENCE: 33
SQSVDYDGDS Y                                                        11

SEQ ID NO: 34            moltype =   length =
SEQUENCE: 34
000

SEQ ID NO: 35            moltype = AA  length = 6
FEATURE                  Location/Qualifiers
REGION                   1..6
                         note = VL CDR3 (CDR-L3) of anti-C1s antibody
```

```
source                      1..6
                            mol_type = protein
                            organism = synthetic construct
SEQUENCE: 35
SNEDPW                                                                    6

SEQ ID NO: 36               moltype = AA  length = 7
FEATURE                     Location/Qualifiers
REGION                      1..7
                            note = VH CDR1 (CDR-H1) of anti-C1s antibody
source                      1..7
                            mol_type = protein
                            organism = synthetic construct
SEQUENCE: 36
GFNIKDD                                                                   7

SEQ ID NO: 37               moltype =    length =
SEQUENCE: 37
000

SEQ ID NO: 38               moltype = AA  length = 8
FEATURE                     Location/Qualifiers
REGION                      1..8
                            note = VH CDR3 (CDR-H3) of anti-C1s antibody
source                      1..8
                            mol_type = protein
                            organism = synthetic construct
SEQUENCE: 38
GYGREVFD                                                                  8

SEQ ID NO: 39               moltype = AA  length = 7
FEATURE                     Location/Qualifiers
REGION                      1..7
                            note = VL CDR1 (CDR-L1) of anti-C1s antibody
source                      1..7
                            mol_type = protein
                            organism = synthetic construct
SEQUENCE: 39
DSYMNWY                                                                   7

SEQ ID NO: 40               moltype = AA  length = 10
FEATURE                     Location/Qualifiers
REGION                      1..10
                            note = VL CDR2 (CDR-L2) of anti-C1s antibody
source                      1..10
                            mol_type = protein
                            organism = synthetic construct
SEQUENCE: 40
ILIYDASNLE                                                               10

SEQ ID NO: 41               moltype = AA  length = 8
FEATURE                     Location/Qualifiers
REGION                      1..8
                            note = VL CDR3 (CDR-L3) of anti-C1s antibody
source                      1..8
                            mol_type = protein
                            organism = synthetic construct
SEQUENCE: 41
QQSNEDPW                                                                  8

SEQ ID NO: 42               moltype = AA  length = 6
FEATURE                     Location/Qualifiers
REGION                      1..6
                            note = VH CDR1 (CDR-H1) of anti-C1s antibody
source                      1..6
                            mol_type = protein
                            organism = synthetic construct
SEQUENCE: 42
KDDYIH                                                                    6

SEQ ID NO: 43               moltype = AA  length = 13
FEATURE                     Location/Qualifiers
REGION                      1..13
                            note = VH CDR2 (CDR-H2) of anti-C1s antibody
source                      1..13
                            mol_type = protein
                            organism = synthetic construct
SEQUENCE: 43
WIGRIDPADG HTK                                                           13
```

```
SEQ ID NO: 44            moltype = AA  length = 11
FEATURE                  Location/Qualifiers
REGION                   1..11
                         note = VH CDR3 (CDR-H3) of anti-C1s antibody
source                   1..11
                         mol_type = protein
                         organism = synthetic construct
SEQUENCE: 44
ARYGYGREVF D                                                                     11

SEQ ID NO: 45            moltype = AA  length = 107
FEATURE                  Location/Qualifiers
REGION                   1..107
                         note = TNT020 VH3/VK2-Fc-sub4
source                   1..107
                         mol_type = protein
                         organism = synthetic construct
SEQUENCE: 45
RTVAAPSVFI FPPSDEQLKS GTASVVCLLN NFYPREAKVQ WKVDNALQSG NSQESVTEQD                60
SKDSTYSLSS TLTLSKADYE KHKVYACEVT HQGLSSPVTK SFNRGEC                             107

SEQ ID NO: 46            moltype = AA  length = 446
FEATURE                  Location/Qualifiers
REGION                   1..446
                         note = VH1 Mature Heavy Chain
source                   1..446
                         mol_type = protein
                         organism = synthetic construct
SEQUENCE: 46
EVQLVQSGAE LKKPGASVKL SCTASGFNIK DDYIHWVKQA PGQGLEWIGR IDPADGHTKY                60
APKFQVKATI TADTSTNTAY LQLSSLTSED TAVYYCARYG YGREVFDYWG QGTTVTVSSA               120
STKGPSVFPL APCSRSTSES TAALGCLVKD YFPEPVTVSW NSGALTSGVH TFPAVLQSSG               180
LYSLSSVVTV PSSSLGTKTY TCNVDHKPSN TKVDKRVESK YGPPCPPCPA PEFEGGPSVF               240
LFPPKPKDTL MISRTPEVTC VVVDVSQEDP EVQFNWYVDG VEVHNAKTKP REEQFNSTYR               300
VVSVLTVLHQ DWLNGKEYKC KVSNKGLPSS IEKTISKAKG QPREPQVYTL PPSQEEMTKN               360
QVSLTCLVKG FYPSDIAVEW ESNGQPENNY KTTPPVLDSD GSFFLYSRLT VDKSRWQEGN               420
VFSCSVLHEA LHSHYTQKSL SLSLGK                                                   446

SEQ ID NO: 47            moltype = AA  length = 446
FEATURE                  Location/Qualifiers
REGION                   1..446
                         note = VH2 Mature Heavy Chain
source                   1..446
                         mol_type = protein
                         organism = synthetic construct
SEQUENCE: 47
EVQLVQSGAE VKKPGASVKL SCTASGFNIK DDYIHWVKQA PGQGLEWIGR IDPADGHTKY                60
APKFQVKATI TADTSTNTAY LELSSLRSED TAVYYCARYG YGREVFDYWG QGTTVTVSSA               120
STKGPSVFPL APCSRSTSES TAALGCLVKD YFPEPVTVSW NSGALTSGVH TFPAVLQSSG               180
LYSLSSVVTV PSSSLGTKTY TCNVDHKPSN TKVDKRVESK YGPPCPPCPA PEFEGGPSVF               240
LFPPKPKDTL MISRTPEVTC VVVDVSQEDP EVQFNWYVDG VEVHNAKTKP REEQFNSTYR               300
VVSVLTVLHQ DWLNGKEYKC KVSNKGLPSS IEKTISKAKG QPREPQVYTL PPSQEEMTKN               360
QVSLTCLVKG FYPSDIAVEW ESNGQPENNY KTTPPVLDSD GSFFLYSRLT VDKSRWQEGN               420
VFSCSVLHEA LHSHYTQKSL SLSLGK                                                   446

SEQ ID NO: 48            moltype = AA  length = 446
FEATURE                  Location/Qualifiers
REGION                   1..446
                         note = VH4 Mature Heavy Chain
source                   1..446
                         mol_type = protein
                         organism = synthetic construct
SEQUENCE: 48
QVQLVQSGAE VKKPGASVKV SCTASGFNIK DDYIHWVRQA PGQGLEWIGR IDPADGHTKY                60
APKFQVKVTI TADTSTSTAY MELSSLRSED TAVYYCARYG YGREVFDYWG QGTTVTVSSA               120
STKGPSVFPL APCSRSTSES TAALGCLVKD YFPEPVTVSW NSGALTSGVH TFPAVLQSSG               180
LYSLSSVVTV PSSSLGTKTY TCNVDHKPSN TKVDKRVESK YGPPCPPCPA PEFEGGPSVF               240
LFPPKPKDTL MISRTPEVTC VVVDVSQEDP EVQFNWYVDG VEVHNAKTKP REEQFNSTYR               300
VVSVLTVLHQ DWLNGKEYKC KVSNKGLPSS IEKTISKAKG QPREPQVYTL PPSQEEMTKN               360
QVSLTCLVKG FYPSDIAVEW ESNGQPENNY KTTPPVLDSD GSFFLYSRLT VDKSRWQEGN               420
VFSCSVLHEA LHSHYTQKSL SLSLGK                                                   446

SEQ ID NO: 49            moltype = AA  length = 446
FEATURE                  Location/Qualifiers
REGION                   1..446
                         note = VH5 Mature Heavy Chain
source                   1..446
                         mol_type = protein
```

```
                        organism = synthetic construct
SEQUENCE: 49
QVQLVQSGAE VKKPGASVKV SCAASGFNIK DDYIHWVRQA PGQGLEWIGR IDPADGHTKY     60
APKFQVKVTI TADTSTSTAY MELSSLRSED TAVYYCARYG YGREVFDYWG QGTTVTVSSA    120
STKGPSVFPL APCSRSTSES TAALGCLVKD YFPEPVTVSW NSGALTSGVH TFPAVLQSSG    180
LYSLSSVVTV PSSSLGTKTY TCNVDHKPSN TKVDKRVESK YGPPCPPCPA PEFEGGPSVF    240
LFPPKPKDTL MISRTPEVTC VVVDVSQEDP EVQFNWYVDG VEVHNAKTKP REEQFNSTYR    300
VVSVLTVLHQ DWLNGKEYKC KVSNKGLPSS IEKTISKAKG QPREPQVYTL PPSQEEMTKN    360
QVSLTCLVKG FYPSDIAVEW ESNGQPENNY KTTPPVLDSD GSFFLYSRLT VDKSRWQEGN    420
VFSCSVLHEA LHSHYTQKSL SLSLGK                                         446

SEQ ID NO: 50            moltype = AA   length = 218
FEATURE                  Location/Qualifiers
REGION                   1..218
                         note = Vkappa1 variant Mature Light Chain
source                   1..218
                         mol_type = protein
                         organism = synthetic construct
SEQUENCE: 50
DIVLTQSPDS LAVSLGERAT ISCKASQSVD YDGDSYMNWY QQKTGQPPKI LIYDASNLES     60
GIPARFSGSG SGTDFTLTIS SLEEEDFAIY YCQQSNEDPW TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 51            moltype = AA   length = 218
FEATURE                  Location/Qualifiers
REGION                   1..218
                         note = Vkappa5 variant Mature Light Chain
source                   1..218
                         mol_type = protein
                         organism = synthetic construct
SEQUENCE: 51
DIVLTQSPDS LAVSLGERAT ISCKASQSVD YDGDSYMNWY QQKPGQPPKL LIYDASNLES     60
GIPARFSGSG SGTDFTLTIS SLEPEDFAVY YCQQSNEDPW TFGGGTKVEI KRTVAAPSVF    120
IFPPSDEQLK SGTASVVCLL NNFYPREAKV QWKVDNALQS GNSQESVTEQ DSKDSTYSLS    180
STLTLSKADY EKHKVYACEV THQGLSSPVT KSFNRGEC                            218

SEQ ID NO: 52            moltype = AA   length = 327
FEATURE                  Location/Qualifiers
REGION                   1..327
                         note = Human IgG4 Constant Region (Fc)
source                   1..327
                         mol_type = protein
                         organism = synthetic construct
SEQUENCE: 52
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPSCP APEFLGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 53            moltype = AA   length = 327
FEATURE                  Location/Qualifiers
REGION                   1..327
                         note = Human IgG4 Constant Region (Fc) Variant 1
source                   1..327
                         mol_type = protein
                         organism = synthetic construct
SEQUENCE: 53
ASTKGPSVFP LAPCSRSTSE STAALGCLVK DYFPEPVTVS WNSGALTSGV HTFPAVLQSS     60
GLYSLSSVVT VPSSSLGTKT YTCNVDHKPS NTKVDKRVES KYGPPCPPCP APEFEGGPSV    120
FLFPPKPKDT LMISRTPEVT CVVVDVSQED PEVQFNWYVD GVEVHNAKTK PREEQFNSTY    180
RVVSVLTVLH QDWLNGKEYK CKVSNKGLPS SIEKTISKAK GQPREPQVYT LPPSQEEMTK    240
NQVSLTCLVK GFYPSDIAVE WESNGQPENN YKTTPPVLDS DGSFFLYSRL TVDKSRWQEG    300
NVFSCSVMHE ALHNHYTQKS LSLSLGK                                        327

SEQ ID NO: 54            moltype = AA   length = 218
FEATURE                  Location/Qualifiers
REGION                   1..218
                         note = Parental Murine anti-C1s VL Mature Light Chain
source                   1..218
                         mol_type = protein
                         organism = synthetic construct
```

```
SEQUENCE: 54
DIVLTQSPAS LAVSLGQRAT ISCKASQSVD YDGDSYMNWY QQKTGQPPKI LIYDASNLES  60
GIPARFSGSG SGTDFTLNIH PVEEEDAAIY YCQQSNEDPW TFGGGTKLEI KRTVAAPSVF 120
IFPPSDEQLK SGTASVVCLL NNFYPREAKV QWKVDNALQS GNSQESVTEQ DSKDSTYSLS 180
STLTLSKADY EKHKVYACEV THQGLSSPVT KSFNRGEC                        218
```